US008354508B2

(12) United States Patent
Diedrich et al.

(10) Patent No.: US 8,354,508 B2
(45) Date of Patent: Jan. 15, 2013

(54) PRO115 ANTIBODY COMPOSITIONS AND METHODS OF USE

(75) Inventors: Gundo Diedrich, South San Francisco, CA (US); Paul Levi Miller, South San Francisco, CA (US); Jackie Papkoff, San Francisco, CA (US); Astrid Strelow, Redwood City, CA (US)

(73) Assignee: Diadexus, Inc., South San Francisco, CA (US)

( * ) Notice: Subject to any disclaimer, the term of this patent is extended or adjusted under 35 U.S.C. 154(b) by 633 days.

(21) Appl. No.: 12/374,292

(22) PCT Filed: Jul. 20, 2007

(86) PCT No.: PCT/US2007/073948
§ 371 (c)(1),
(2), (4) Date: Feb. 5, 2010

(87) PCT Pub. No.: WO2008/127347
PCT Pub. Date: Oct. 23, 2008

(65) Prior Publication Data
US 2010/0150907 A1 Jun. 17, 2010

Related U.S. Application Data

(60) Provisional application No. 60/832,531, filed on Jul. 21, 2006.

(51) Int. Cl.
*C07K 16/00* (2006.01)
*C12P 21/08* (2006.01)
*C12N 5/07* (2010.01)
*C12N 5/16* (2006.01)

(52) U.S. Cl. .............. 530/388.1; 530/387.3; 530/387.7; 435/326

(58) Field of Classification Search ................... None
See application file for complete search history.

(56) References Cited

U.S. PATENT DOCUMENTS

| 6,350,448 | B1 | 2/2002 | Bandman et al. | |
|---|---|---|---|---|
| 2002/0119531 | A1* | 8/2002 | Bandman et al. | 435/70.21 |
| 2004/0018203 | A1* | 1/2004 | Pastan et al. | 424/178.1 |
| 2005/0239122 | A1 | 10/2005 | Afar et al. | |

OTHER PUBLICATIONS

Fundamental Immunology 242 (William E. Paul, M.D. ed., 3d ed. 1993).*
Greenspan et al., Nature Biotechnology 7: 936-937, 1999.*
International Search Report and Written Opinion, PCT/US2007/073948, Sep. 18, 2008, 6 Pages.
Afar, D., et al., Catalytic Cleavage of the Androgen-regulated TMPRSS2 Protease Results in its Secretion by Prostate Cancer Epithelia, Cancer Research, Feb. 15, 2001, pp. 1686-1692, vol. 61.

* cited by examiner

*Primary Examiner* — Hong Sang
(74) *Attorney, Agent, or Firm* — Licata & Tyrrell P.C.; Keith R. McCollum

(57) ABSTRACT

The invention provides isolated anti-Pro115 antibodies that bind to Pro115. The invention also encompasses compositions comprising an anti-Pro115 antibody and a carrier. These compositions can be provided in an article of manufacture or a kit. Another aspect of the invention is an isolated nucleic acid encoding an anti-Pro115 antibody, as well as an expression vector comprising the isolated nucleic acid. Also provided are cells that produce the anti-Pro115 antibodies. The invention encompasses a method of producing the anti-Pro115 antibodies. Other aspects of the invention are a method of killing an Pro115-expressing cancer cell, comprising contacting the cancer cell with an anti-Pro115 antibody and a method of alleviating or treating an Pro115-expressing cancer in a mammal, comprising administering a therapeutically effective amount of the anti-Pro115 antibody to the mammal.

18 Claims, 5 Drawing Sheets

Figure 1

```
hPro115   ------------------------------------------------------------
mPro115   ------------------------------------------------------------
TMPRSS1   ------------------------------------------------------------
TMPRSS3   ------------------------------------------------------------
TMPRSS4   ------------------------------------------------------------
TMPRSS5   ------------------------------------------------------------
TMPRSS6   ------------------------------------------------------------
TMPRSS7   ------------------------------------------------------------
TMPRSS9   MEPTVADVHLVPRTTKEVPALDAACCRAASIGVVATSLVVLTLGVLLAFLSTQGFHVDHT  60
TMPRSS10  ----------------------------------------------MKQSPALAPEERCR  14
TMPRSS13  ------------------------------------------------------------
TMPRSS12  ------------------------------------------------------------ hPro115   ------------------------------------------------------------
mPro115   ------------------------------------------------------------
TMPRSS1   ------------------------------------------------------------
TMPRSS3   ------------------------------------------------------------
TMPRSS4   ------------------------------------------------------------
TMPRSS5   ------------------------------------------------------------
TMPRSS6   ------------------------------------------------------------
TMPRSS7   ------------------------------------------------------------
TMPRSS9   AELRGIRWTSSLRRETSDYHRTLTPTLEALLHFLLRPLQTLSLGLEEELLQRGIRARLRE  120
TMPRSS10  RAGSPKPVLRADDNNMGNGCSQKLATANLLRFLLLVLIPCICALVLLLVILLSYVGTLQK  74
TMPRSS13  ------------------------------------------------------------
TMPRSS12  ------------------------------------------------------------ hPro115   ------------------------------------------------------------
mPro115   ------------------------------------------------------------
TMPRSS1   ------------------------------------------------------------
TMPRSS3   ------------------------------------------------------------
TMPRSS4   ------------------------------------------------------------
TMPRSS5   ------------------------------------------------------------
TMPRSS6   ------------------------------------------------------------
TMPRSS7   ------------------------------------------------------------
TMPRSS9   HGISLAAYGTIVSAELTGRHKGPLAERDFKSGRCPGNSFSCGNSQCVTKVNPECDDQEDC  180
TMPRSS10  VYFKSNGSEPLVTDGEIQGSDVILTNTIYNQSTVVSTAHPDQHVPAWTTDASLPGDQSHR  134
TMPRSS13  ------------------------------------------------------------
TMPRSS12  ------------------------------------------------------------ hPro115   ------------------------------------------------------------
mPro115   ------------------------------------------------------------
TMPRSS1   ------------------------------------------------------------
TMPRSS3   ------------------------------------------------------------
TMPRSS4   ------------------------------------------------------------
TMPRSS5   ------------------------------------------------------------
TMPRSS6   ----------------------------------------------------MLLLFHSK  8
TMPRSS7   ------------------------------------------------------------
TMPRSS9   SDGSDEAHCECGLQPAWRMAGRIVGGMEASPGEFPWQASLRENKEHFCGAAIINARWLVS  240
TMPRSS10  NTSACMNITHSQCQMLPYHATLTPLLSVVRNMEMEKFLKFFTYLHRLSCYQHIMLFGCTL  194
TMPRSS13  ------------------------------------------------------------
TMPRSS12  ------------------------------------------------------------
```

Figure 1 Continued

```
hPro115   ------------------------------------------------------------
mPro115   ------------------------------------------------------------
TMPRSS1   ------------------------------------------------------------
TMPRSS3   ------------------------------------------------------------
TMPRSS4   ------------------------------------------------------------
TMPRSS5   ------------------------------------------------------------
TMPRSS6   RMPVAEAPQVAGGQGDGGDGEEAEPEGMFKACEDSKRKARGYLRLVPLFVLLALLVLASA  68
TMPRSS7   ------------------------------------------------------------
TMPRSS9   AAHCFNEFQDPTKWVAYVGATYLSGSEASTVRAQVVQIVKHPLYNADTADFDVAVLELTS  300
TMPRSS10  AFPECIIDGDDSHGLLPCRSFCEAAKEGCESVLGMVNYSWPDFLRCSQFRNQTESSNVSR  254
TMPRSS13  ------------------------------------------------------------
TMPRSS12  ------------------------------------------------------------ hPro115   ------------------------------------------------------------
mPro115   ------------------------------------------------------------
TMPRSS1   ------------------------------------------------------------
TMPRSS3   ------------------------------------------------------------
TMPRSS4   ------------------------------------------------------------
TMPRSS5   ------------------------------------------------------------
TMPRSS6   GVLLWYFLGYKAEVMVSQVYSGSLRVLNRHFSQDLTRRESSAFRSETAKAQKMLKELITS  128
TMPRSS7   ------------------------------------------------------------
TMPRSS9   PLPFGRHIQPVCLPAATHIFPPSKKCLISGWGYLKEDFLVKPEVLQKATVELLDQALCAS  360
TMPRSS10  ICFSPQQENGKQLLCGRGENFLCASGICIPGKLQCNGYNDCDDWSDEAHCNCSENLFHCH  314
TMPRSS13  ------------------------------------------------------------
TMPRSS12  ------------------------------------------------------------ hPro115   ------------------------------------------------------------
mPro115   ------------------------------------------------------------
TMPRSS1   ------------------------------------------------------------
TMPRSS3   ------------------------------------------------------------
TMPRSS4   ------------------------------------------------------------
TMPRSS5   ------------------------------------------------------------
TMPRSS6   TRLGTYYNSSSVYSFGEGPLTCFFWFILQIPEHRRLMLSPEVVQALLVEELLSTVNSSAA  188
TMPRSS7   ------------------------------------------------------------
TMPRSS9   LYGHSLTDRMVCAGYLDGKVDSCQGDSGGPLVCEEPSGRFFLAGIVSWGIGCAEARRPGV  420
TMPRSS10  TGKCLNYSLVCDGYDDCGDLSDEQNCDCNPTTEHRCGDGRCIAMEWVCDGDHDCVDKSDE  374
TMPRSS13  ------------------------------------------------------------
TMPRSS12  ------------------------------------------------------------ hPro115   ------------------------------------------------------------
mPro115   ------------------------------------------------------------
TMPRSS1   ------------------------------------------------------------
TMPRSS3   ------------------------------------------------------------
TMPRSS4   ------------------------------------------------------------
TMPRSS5   ------------------------------------------------------------
TMPRSS6   VPYRAEYEVDPEGLVILEASVKDIAALNSTLGCYRYSYVGQGQVLRLKGPDHLASSCLWH  248
TMPRSS7   ------------------------------------------------MCHFK         5
TMPRSS9   YARVTRLRDWILEATTKASMPLAPTMAPAPAAPSTAWPTSPESPVVSTPTKSMQALSTVP  480
TMPRSS10  VNCSCHSQGLVECRNGQCIPSTFQCDGDEDCKDGSDEENCSVIQTSCQEGDQRCLYNPCL  434
TMPRSS13  ---------------------------------------MERDSHGNASPARTP       15
TMPRSS12  ------------------------------------------------------------
```

Figure 1 Continued

```
hPro115   --------------------------------MALNSGSPPAIGPYYENHGYQPENPYPAQ  29
mPro115   --------------------------------MALNSGSPPGIGPCYENHGYQSEHICPPR  29
TMPRSS1   -----------------------------------MAQKEGGRTVPCCSRPKVAALTAG---  24
TMPRSS3   ---------------------------------MGENDPPAVEAPFSFRSLFGLDDLKIS  27
TMPRSS4   ----------------------------------------MLQDPDSDQPLNSLDVKPLR  20
TMPRSS5   --------------------------------MSLMLDDQPPMEAQYAEEGP-GPGIFRAE  28
TMPRSS6   LQGPKDLMLKLRLEWTLAECR----DRLAMYDVAGPLEKRLITSVYGCSRQEPVVEVLAS  304
TMPRSS7   LVAIVGYLIRLSIKSIQIEADNCVTDSLTIYDSLLPIRSSILYRICEPTR--TLMSFVST   63
TMPRSS9   LDWVTVPKLQECGARPAMEKPTRVVGGFGAASGEVPWQVSLKEGSRHFCGATVVGDRWLL  540
TMPRSS10  DSCGGSSLCDPNNSLNNCSQCEPITLELCMNLPYNSTSYPNYFGHRTQKEASISWESSLF  494
TMPRSS13  SAGASPAQASPAGTPPGRASPAQASPAQASPAGTPPGRASPAQASPAGTPPGRASPGRAS   75
TMPRSS12  ------------------------------------------------------------ hPro115   PTVVPTVYEVHPAQYYPSPVPQYAPRVLTQASNPVVCTQPKSP--SGTVCTSKTKKALCI   87
mPro115   PPVAPNGYNLYPAQYYPSPVPQYAPRITTQASTSVIHTHPKS---SGALCTSKSKKSLCL   86
TMPRSS1   ------------------------------------------------------------
TMPRSS3   P-VAPDADAVAAQILSLLPLKFFP------------------------------------   50
TMPRSS4   KPRIPMETFRKVGIPIIIAL----------------------------------------   40
TMPRSS5   PGDQQHPISQAVCWRSMRRG------------------------------------CA    50
TMPRSS6   GAIMAVVWKKGLHSYYDPFVLSVQPVVFQACEVNLTLDNRLDSQGVLSTPYFPSYYSPQT  364
TMPRSS7   NNLMLVTFKSPHIRRLSGIRAYFEVIPEQKCENTVLVKDITGFEGKISSPYYPSYYPPKC  123
TMPRSS9   SAAHCFNHTKVEQVRAHLGTASLLGLGGSPVKIGLRRVVLHPLYNPGILDFDLAVLELAS  600
TMPRSS10  PALVQTNCYKYLMFFSCTILVPKCDVNTGEHIPPCRALCEHSKERCESVLGIVGLQWPED  554
TMPRSS13  PAQASPAQASPAQASPARASPALASLSRSSSGRSSSARSASVTTSPTRVYLVRATPVGAV  135
TMPRSS12  ------------------------------------------------------------

|--peptide 1--|     |--peptide 3--|      |-
                         |--peptide 2--|       |--peptide 4
hPro115   TLTLGTFLVGAALAAGLLWKFMGSKCSNSGIECDSSGTCINPSNWCDGVSHCPGGEDENR  147
mPro115   ALALGTVLTGAAVAAVLLWRFWDSNCSTSEMECGSSGTCISSSLWCDGVAHCPNGEDENR  146
TMPRSS1   -----TLLLLTAIG------------------AASWAIVAVLLRSDQEPLYPVQVS---   57
TMPRSS3   IIVIGIIALILALAIGLGIHFD---CSG-KYRCRSSFKCIELIARCDGVSDCKDGEDEYR  106
TMPRSS4   -LSLASIIIVVVLIKVILDKYY--------FLCGQPLHFIPRKQLCDGELDCPLGEDEEH   91
TMPRSS5   VLGALGLLAGAGVGSWLLVLYLCPAASQPISGTLQDEEITLSCSEASAEEALLPALPKTV  110
TMPRSS6   HCSWHLTVPSLDYGLALWFDAYALRRQKYDLPCTQGQWTIQNRRLCGLRILQPYAERIPV  424
TMPRSS7   KCTWKFQTSLSTLGIALKFYNYSITKKSMKG-CEHGWWEINEHMYCGSYMDH---QTIFR  179
TMPRSS9   PLAFNKYIQPVCLPLAIQKFPVGRKCMISGWGNTQEGNATKPELLQKASVGIIDQKTCSV  660
TMPRSS10  TDCSQFPEENSDNQTCLMPDEYVEECSPSHFKCRSGQ-CVLASRRCDGQADCDDDSDEEN  613
TMPRSS13  PIRSSPARSAPATRATRESPVQFWQGHTGIRYKEQRESCPKHAVRCDGVVDCKLKSDELG  195
TMPRSS12  ------------------------------------------------------------

----------------------------------peptide 5--|       |-----
                --|                                   |--peptide 6--|
hPro115   CVR----------------------------------LYGPNFILQMYSSQRKSWHPV  171
mPro115   CVR----------------------------------LYGQSFILQVYSSQRKAWYPV  170
TMPRSS1   ----------------------------------------SADARLMVFDKTEGTWRLL   76
TMPRSS3   CVR----------------------------------VGGQNAVLQVFTAA--SWKTM  128
TMPRSS4   CVKS---------------------------FPEGPAVAVRLSKDRSTLQVLDSATGNWFSA  126
TMPRSS5   SFR----------------------------------INSEDFLLEAQVRDQPRWLLV  134
TMPRSS6   VATA---------------------------------GITINFTSQISLTGPGVRVHYGLYNQSDPCP  459
TMPRSS7   VPSP---------------------------------LVHIQLQCSSRLSDKPLLAEYGSYNISQPCP  214
TMPRSS9   LYNFSLTDRMICAG---------FLEGKVDSCQGDSGGPLACEEAPGVFYLAGIVSWGIG  711
TMPRSS10  CGCKERDLWECPSNKQCLKHTVICDGFPDCPDYMDEKNCSFCQDDELECANHACVSRDLW  673
TMPRSS13  CVR----------------------------------FDWDKSLLKIYSGSSHQWLPI  219
TMPRSS12  ---------------------------------------------MRLGLLSVALLFV   13
```

Figure 1 Continued

```
                   ------------------------------------peptide 7--|       |--peptide 9
                                                                   |--peptide 8--|
hPro115    CQ----------------------------------------DDWNENYGRAACRDMGYK 191
mPro115    CQ----------------------------------------DDWSESYGRAACKDMGYK 190
TMPRSS1    CS----------------------------------------SRSNARVAGLSCEEMGFL  96
TMPRSS3    CS----------------------------------------DDWKGHYANVACAQLGFP 148
TMPRSS4    CF----------------------------------------DNFTEALAETACRQMGYS 146
TMPRSS5    CH----------------------------------------EGWSPALGLQICWSLGHL 154
TMPRSS6    GEFLCSVNGLCVP---ACDGV---------------------KDCPNGLDERNCVCRATF 495
TMPRSS7    VGSFRCSSGLCVPQAQRCDGV---------------------NDCFDESDELFCVS-PQP 252
TMPRSS9    CAQVKKPGVYTRITRLKG-----------------WILEIMSSQPLPMSPPSTTRMLAT 753
TMPRSS10   CDGEADCSDSSDEWDCVTLSINVNSSSFLMVHRAATEHHVCADGWQEILSQLACKQMGLG 733
TMPRSS13   CS----------------------------------------SNWNDSYSEKTCRQLGFE 239
TMPRSS12   GSS---------------------------------------HLYSDHYSPSGRHRLGPS  34 peptide 9--|        |-------------------peptide 11-|      |--peptide 13
                  |--peptide 10-|       |-------------------peptide 12-|
hPro115    NNFYSSQGIVDDSGSTSFMKLNTSAGN-----------------VDIYKKLYHSDACSS 233
mPro115    NNFYSSQGIPDQSGATSFMKLNVSSGN-----------------VDLYKKLYHSDSCSS 232
TMPRSS1    RALTHSELDVRTAGANGTSGFFCVDEGRLP--------------HTQRLLEVISVCDCPR 142
TMPRSS3    -SYVSSDNLRVSSLEGQFREEFVSIDHLLPDD-----------KVTALHHSVYVREGCAS 196
TMPRSS4    SKPTFRAVEIGPDQDLDVVEITENSQE----------------------LRMRNSSGPCLS 185
TMPRSS5    RLTHHKGVNLTDIKLNSSQEFAQLSPRLG---------------GFLEEAWQPRNNCTS 198
TMPRSS6    QCKEDSTCISLPKVCDGQPDCLNGSDEEQCQEGVPCGTFTFQCEDRSCVKKPNPQCDGRP 555
TMPRSS7    ACNTSSFRQHGPLICDGFRDCENGRDEQNCTQSIPCNNRTFKCGNDICFRKQNAKCDGTV 312
TMPRSS9    TSPRTTAGLTVPGATPSRPTPGAASRVTGQPAN---------STLSAVSTTARGQTPFPD 804
TMPRSS10   EPSVTKLIQEQEKEPRWLTLHSNWESLNG---------------TTLHELLVNGQSCES 777
TMPRSS13   SAHRTTEVAHRDFANSFSILRYN-----------------------STIQESLHRSHCPS 276
TMPRSS12   PEPAASSQQAEAVRKRLRR---------------------------RREGGAHAKDCGT  66 peptide 13-|       |--peptide 15-|     |------peptide 17-|       |-
               |----peptide 14-|      |--peptide 16-|       |------peptide 18
hPro115    KAVVSLRC---IACGVNLNSSRQSRIVGGESALPGAWPWQVSLHVQN----VHVCGGSIIT 287
mPro115    RMVVSLRC--IECGVRS-VKRQSRIVGGLNASPGDWPWQVSLHVQG----VHVCGGSIIT 285
TMPRSS1    GRFLAAIC--QDCGRRK--LPVDRIVGGRDTSLGRWPWQVSLRYDG----AHLCGSLLS 194
TMPRSS3    GHVVTLQC--TACGHRR--GYSSRIVGGNMSLLSQWPWQASLQFQG----YHLCGGSVIT 248
TMPRSS4    GSLVSLHC--LACGKSL---KTPRVVGGEEASVDSWPWQVSIQYDK----QHVCGGSILD 236
TMPRSS5    GQVVSLRC--SECGARP---LASRIVGGQSVAPGRWPWQASVALGF----RHTCGGSVLA 249
TMPRSS6    DCRDGSDE--EHCDCG-LQGPSSRIVGGAVSSEGEWPWQASLQVRG----RHICGGALIA 608
TMPRSS7    DCPDGSDE--EGCTCSRSSSALHRIIGGTDTLEGGWPWQVSLHFVG----SAYCGASVIS 366
TMPRSS9    APEATTHTQLPDCGLAP--AALTRIVGGSAAGRGEWPWQVSLWLRRR---EHRCGAVLVA 859
TMPRSS10   RSKISLLCTKQDCGRRPAARMNKRILGGRTSRPGRWPWQCSLQSEPS---GHICGCVLIA 834
TMPRSS13   QRYISLQC--SHCGLRA---MTGRIVGGALASDSKWPWQVSLHFGT----THICGGTLID 327
TMPRSS12   APLKDVLQ-----------GSRIIGGTEAQGAWPWVVSLQIKYGRVLVHVCGGTLVR 113
                                 *::**   .  ***  *:         **  ::

-peptide 19-|        |--peptide 21-|        |-------peptide 23-|
       --|     |---peptide 20-|        |--peptide 22-|         |--peptide 24
hPro115    PEWIVTAAHCVEKP-LNNPWHWTAFAGILRQSFMFYGAGYQVEKVIS-----HPNYDSKT 341
mPro115    PEWIVTAAHCVEEP-LSSPRYWTAFAGILRQSLMFYGSRHQVEKVIS-----HPNYDSKT 339
TMPRSS1    GDWVLTAAHCFPER-NRVLSRWRVFAGAVAQASPHGLQLGVQAVVYHGGYLPFRDPNSEE 253
TMPRSS3    PLWIITAAHCVYD--LYLPKSWTIQVGLVSL-LDNPAPSHLVEKIVY-----HSKYKPKR 300
TMPRSS4    PHWVLTAAHCFRK--HTDVFNWKVRAGSDKLGSFPSLAVAKIIIIEF-----NPMYP--- 286
TMPRSS5    PRWVVTAAHCMHSFRLARLSSWRVHAGLVSHSAVRPHQGALVERIIP-----HPLYSAQN 304
TMPRSS6    DRWVITAAHCFQEDSMASTVLWTVFLGKVWQNSRWPGEVSFKVSRLL----LHPYHEEDS 664
TMPRSS7    REWLLSAAHCFHGNRLSDPTPWTAHLGMYVQGN---AKFVSPVRRIV----VHEYYNSQT 419
TMPRSS9    ERWLLSAAHCFDVY--GDPKQWAAFLGTPFLSGAEGQLERVARIYKH------PFYNLYT 911
TMPRSS10   KKWVLTVAHCFEGR--ENAAVWKVVLGINNLDHPSVFMQTRFVKTIIL----HPRYSRAV 888
TMPRSS13   AQWVLTAAHCFFVTREKVLEGWKVYAGTSNLHQLPEAASIAEIIINS-------NYTDEE 380
TMPRSS12   ERWVLTAAHCTKDA--SDPLMWTAVIGTNNIHGRYPHTKKIKIKAIII----HPNFILES 167
            *::::.***              *    *
```

Figure 1 Continued

```
              |----peptide 25-|      |---peptide 27-|      |--peptide 29
     peptide 24-|          |--peptide 26-|      |----peptide 28-|      |-
hPro115   KNNDIALMKLQ--KPLTFNDLVKPVCLPNPGMMLQPE-QLCWISGWGATEE-KGKTSEVL 397
mPro115   KNNDIALMKLQ--TPLAFNDLVKPVCLPNPGMMLDLD-QECWISGWGATYE-KGKTSDVL 395
TMPRSS1   NSNDIALVHLS--SPLPLTEYIQPVCLPAAGQALVDG-KICTVTGWGNTQY-YGQQAGVL 309
TMPRSS3   LGNDIALMKLA--GPLTFNEMIQPVCLPNSEENFPDG-KVCWTSGWGATEDGAGDASPVL 357
TMPRSS4   KDNDIALMKLQ--FPLTFSGTVRPICLPFFDEELTPA-TPLWIIGWGFTKQNGGKMSDIL 343
TMPRSS5   HDYDVALLRLQ--TALNFSDTVGAVCLPAKEQHFPKG-SRCWVSGWGHTHPSHTYSSDML 361
TMPRSS6   HDYDVALLQL---DHPVVRSAAVRPVCLPARSHFFEPG-LHCWIGWGALREG-GPISNAL 720
TMPRSS7   FDYDIALLQLSIAWPETLKQLIQPICIPPTGQRVRSG-EKCWVTGWGRRHEADNKGSLVL 478
TMPRSS9   LDYDVALLELAG--PVRRSRLVRPICLPEPAPRPPDG-TRCVITGWGSVRE-GGSMARQL 967
TMPRSS10  VDYDISIVELS--EDISETGYVRPVCLPNPEQWLEPD-TYCYITGWGHMGN---KMPFKL 942
TMPRSS13  DDYDIALMRLS--KPLTLSAHIHPACLPMHGQTFSLN-ETCWITGFGKTRETDDKTSPFL 437
TMPRSS12  YVNDIALFHLK--KAVRYNDYIQPICLPFDVFQILDGNTKCFISGWGRTKE-EGNATNIL 224
              *::::..*       .  :  . *:*            *:*           .  *

--|       |--peptide 31-|     |--peptide 33-|     |--peptide 35
           -peptide 30-|       |--peptide 32-|     |--peptide 34-|
hPro115   NAAKVLLIETQRCNSRYVYDNLITPAMICAGFLQGNVDSCQGDSGGPLVTSKNN----IW 453
mPro115   NAAMVPLIEPSKCNSKYIYNNLITPAMICAGFLQGSVDSCQGDSGGPLVTLKNG----IW 451
TMPRSS1   QEARVPITSNDVCNGADFYGNQIKPKMFCAGYLPEGGIDACQGDSGGPFVCEDSISRTPRW 369
TMPRSS3   NHAAVPLISNKICNHRDVYGGIISPSMLCAGYLTGGVDSCQGDSGGPLVCQERR----LW 413
TMPRSS4   LQASVQVIDSTRCNADDAYQGEVTEKMMCAGIPEGGVDTCQGDSGGPLMYQSD-----QW 398
TMPRSS5   QDTVVPLFSTQLCNSSCVYSGALTPRMLCAGYLDGRADACQGDSGGPLVCPDGD----TW 417
TMPRSS6   QKVDVQLIPQDLC--SEVYRYQVTPRMLCAGYRKGKKDACQGDSGGPLVCKALS---GRW 775
TMPRSS7   QQAEVELIDQTLC--VSTYG-IITSRMLCAGIMSGKRDACKGDSGGPLSCRRKSD--GKW 533
TMPRSS9   QKAAVRLLSEQTCR--RFYPVQISSRMLCAGFPQGGVDSCSGDAGGPLACREPSG---RW 1022
TMPRSS10  QEGEVRIISLEHCQ-SYFDMKTITTRMICAGYESGTVDSCMGDSGGPLVCEKPGG---RW 998
TMPRSS13  REVQVNLIDFKKCNDYLVYDSYLTPRMMCAGDLHGGRDSCQGDSGGPLVCFQNN----RW 493
TMPRSS12  QDAEVHYISREMCNSERSYGGIIPNTSFCAGDEDGAFDTCRGDSGGPLMCYLPEYK--RF 282
              *   :    *         :   :***    *  *:*  **:***:       :

peptide 35-|      |---peptide 37-|      |--peptide 39-|
            |--peptide 36-|       |--peptide 38-|
hPro115   WLIGDTSWGSGCAKAYR-PGVYGNVMVFTDWIYRQMRADG-------------------- 492
mPro115   WLIGDTSWGSGCAKALR-PGVYGNVTVFTDWIYQQMRANS-------------------- 490
TMPRSS1   RLCGIVSWGTGCALAQK-PGVYTKVSDFREWIFQAIKTHSEASGMVTQL----------- 417
TMPRSS3   KLVGATSFGIGCAEVNK-PGVYTRVTSFLDWIHEQMERDLKT------------------ 454
TMPRSS4   HVVGIVSWGYGCGGPST-PGVYTKVSAYLNWIYNVWKAEL-------------------- 437
TMPRSS5   RLVGVVSWGRACAEPNH-PGVYAKVAEFLDWIHDTAQDSLL------------------- 457
TMPRSS6   FLAGLVSWGLGCGRPNY-FGVYTRITGVISWIQQVVT----------------------- 811
TMPRSS7   ILTGIVSWGHGSGRPNF-PGVYTRVSNFVPWIHKYVPSLL-------------------- 572
TMPRSS9   VLTGVTSWGYGCGRPHF-PGVYTRVAAVRGWIGQHIQE---------------------- 1059
TMPRSS10  TLFGLTSWGSVCFSKVLGPGVYSNVSYFVEWIKRQIYIQTFLLN--------------- 1042
TMPRSS13  YLAGVTSWGTGCGQRNK-PGVYTKVTEVLPWIYSKMESEVRFRKS-------------- 537
TMPRSS12  FVMGITSYGHGCGRRGF-PGVYIGPSFYQKWLTEHFFHASTQGILTINILRGQILIALCF 341
            :  * .*:*  .     ***         *:

hPro115   -------
mPro115   -------
TMPRSS1   -------
TMPRSS3   -------
TMPRSS4   -------
TMPRSS5   -------
TMPRSS6   -------
TMPRSS7   -------
TMPRSS9   -------
TMPRSS10  -------
TMPRSS13  -------
TMPRSS12  VILLATT 348
```

PRO115 ANTIBODY COMPOSITIONS AND METHODS OF USE

This application is the National Stage of International Application No. PCT/US2007/073948, published in English under PCT Article 21(2), filed Jul. 20, 2007, which claims priority to U.S. Patent Application No. 60/832,531, filed on Jul. 21, 2006, which is incorporated by reference in its entirety.

FIELD OF THE INVENTION

The present invention relates to anti-Pro115 antibody compositions and methods of killing Pro115-expressing prostate, colon, lung or pancreas cancer cells.

BACKGROUND OF THE INVENTION

Prostate Cancer

Prostate cancer is the most prevalent cancer in men and is the second leading cause of death from cancer among males in the United States. *AJCC Cancer Staging Handbook* 203 (Irvin D. Fleming et al. eds., 5$^{th}$ ed. 1998); Walter J. Burdette, *Cancer: Etiology, Diagnosis, and Treatment* 147 (1998). The American Cancer Society estimated there will be 234,460 new cases of prostate cancer and 27,350 deaths in 2005. Additionally, the rate of prostate cancer deaths in the United States for 1997-2001 was 31.5 per 100,000 men, second only to lung and bronchus cancer. American Cancer Society website: cancer with the extension .org of the world wide web. Cancer of the prostate typically occurs in older males, with a median age of 74 years for clinical diagnosis. Burdette, supra at 147. A man's risk of being diagnosed with invasive prostate cancer in his lifetime is one in six. Platz et al., supra at 21.

Although our understanding of the etiology of prostate cancer is incomplete, the results of extensive research in this area point to a combination of age, genetic and environmental/dietary factors. Platz et al., supra at 19; Burdette, supra at 147; Steven K. Clinton, *Diet and Nutrition in Prostate Cancer Prevention and Therapy, in Prostate Cancer: a Multidisciplinary Guide* 246-269 (Philip W. Kantoff et al. eds. 1997). Broadly speaking, genetic risk factors predisposing one to prostate cancer include race and a family history of the disease. Platz et al., supra at 19, 28-29, 32-34. Aside from these generalities, a deeper understanding of the genetic basis of prostate cancer has remained elusive. Considerable research has been directed to studying the link between prostate cancer, androgens, and androgen regulation, as androgens play a crucial role in prostate growth and differentiation. Meena Augustus et al., *Molecular Genetics and Markers of Progression, in Management of Prostate Cancer* 59 (Eric A Klein ed. 2000). While a number of studies have concluded that prostate tumor development is linked to elevated levels of circulating androgen (e.g., testosterone and dihydrotestosterone), the genetic determinants of these levels remain unknown. Platz et al., supra at 29-30.

Several studies have explored a possible link between prostate cancer and the androgen receptor (AR) gene, the gene product of which mediates the molecular and cellular effects of testosterone and dihydrotestosterone in tissues responsive to androgens. Id. at 30. Differences in the number of certain trinucleotide repeats in exon 1, the region involved in trans-activational control, have been of particular interest. Augustus et al., supra at 60. For example, these studies have revealed that as the number of CAG repeats decreases the transactivation ability of the gene product increases, as does the risk of prostate cancer. Platz et al., supra at 30-31. Other research has focused on the α-reductase Type 2 gene, the gene which codes for the enzyme that converts testosterone into dihydrotestosterone. Id. at 30. Dihydrotestosterone has greater affinity for the AR than testosterone, resulting in increased transactivation of genes responsive to androgens. Id. While studies have reported differences among the races in the length of a TA dinucleotide repeat in the 3' untranslated region, no link has been established between the length of that repeat and prostate cancer. Id. Interestingly, while ras gene mutations are implicated in numerous other cancers, such mutations appear not to play a significant role in prostate cancer, at least among Caucasian males. Augustus, supra at 52.

Environmental/dietary risk factors which may increase the risk of prostate cancer include intake of saturated fat and calcium. Platz et al., supra at 19, 25-26. Conversely, intake of selenium, vitamin E and tomato products (which contain the carotenoid lycopene) apparently decrease that risk. Id. at 19, 26-28 The impact of physical activity, cigarette smoking, and alcohol consumption on prostate cancer is unclear. Platz et al., supra at 23-25.

Periodic screening for prostate cancer is most effectively performed by digital rectal examination (DRE) of the prostate, in conjunction with determination of the serum level of prostate-specific antigen (PSA). Burdette, supra at 148. While the merits of such screening are the subject of considerable debate, Jerome P. Richie & Irving D. Kaplan, *Screening for Prostate Cancer: The Horns of a Dilemma, in Prostate Cancer: A Multidisciplinary Guide* 1-10 (Philip W. Kantoff et al. eds. 1997), the American Cancer Society and American Urological Association recommend that both of these tests be performed annually on men 50 years or older with a life expectancy of at least 10 years, and younger men at high risk for prostate cancer. Ian M. Thompson & John Foley, *Screening for Prostate Cancer, in Management of Prostate Cancer* 71 (Eric A Klein ed. 2000). If necessary, these screening methods may be followed by additional tests, including biopsy, ultrasonic imaging, computerized tomography, and magnetic resonance imaging. Christopher A. Haas & Martin I. Resnick, *Trends in Diagnosis, Biopsy, and Imaging, in Management of Prostate Cancer* 89-98 (Eric A Klein ed. 2000); Burdette, supra at 148.

Once the diagnosis of prostate cancer has been made, treatment decisions for the individual are typically linked to the stage of prostate cancer present in that individual, as well as his age and overall health. Burdette, supra at 151. One preferred classification system for staging prostate cancer was developed by the American Urological Association (AUA). Id. at 148. The AUA classification system divides prostate tumors into four broad stages, A to D, which are in turn accompanied by a number of smaller substages. Burdette, supra at 152-153; Anthony V. D'Amico et al., *The Staging of Prostate Cancer, in Prostate Cancer: A Multidisciplinary Guide* 41 (Philip W. Kantoff et al. eds. 1997).

Stage A prostate cancer refers to the presence of microscopic cancer within the prostate gland. D'Amico, supra at 41. This stage is comprised of two substages: A1, which involves less than four well-differentiated cancer foci within the prostate, and A2, which involves greater than three well-differentiated cancer foci or alternatively, moderately to poorly differentiated foci within the prostate. Burdette, supra at 152; D'Amico, supra at 41. Treatment for stage A1 preferentially involves following PSA levels and periodic DRE. Burdette, supra at 151. Should PSA levels rise, preferred treatments include radical prostatectomy in patients 70 years of age and younger, external beam radiotherapy for patients between 70 and 80 years of age, and hormone therapy for those over 80 years of age. Id.

Stage B prostate cancer is characterized by the presence of a palpable lump within the prostate. Burdette, supra at 152-53; D'Amico, supra at 41. This stage is comprised of three substages: B1, in which the lump is less than 2 cm and is contained in one lobe of the prostate; B2, in which the lump is greater than 2 cm yet is still contained within one lobe; and B3, in which the lump has spread to both lobes. Burdette, supra, at 152-53. For stages B1 and B2, the treatment again involves radical prostatectomy in patients 70 years of age and younger, external beam radiotherapy for patients between 70 and 80 years of age, and hormone therapy for those over 80 years of age. Id. at 151. In stage B3, radical prostatectomy is employed if the cancer is well-differentiated and PSA levels are below 15 ng/mL; otherwise, external beam radiation is the chosen treatment option. Id.

Stage C prostate cancer involves a substantial cancer mass accompanied by extraprostatic extension. Burdette, supra at 153; D'Amico, supra at 41. Like stage A prostate cancer, Stage C is comprised of two substages: substage C1, in which the tumor is relatively minimal, with minor prostatic extension, and substage C2, in which the tumor is large and bulky, with major prostatic extension. Id. The treatment of choice for both substages is external beam radiation. Burdette, supra at 151.

The fourth and final stage of prostate cancer, Stage D, describes the extent to which the cancer has metastasized. Burdette, supra at 153; D'Amico, supra at 41. This stage is comprised of four substages: (1) D0, in which acid phosphatase levels are persistently high, (2) D1, in which only the pelvic lymph nodes have been invaded, (3) D2, in which the lymph nodes above the aortic bifurcation have been invaded, with or without distant metastasis, and (4) D3, in which the metastasis progresses despite intense hormonal therapy. Id. Treatment at this stage may involve hormonal therapy, chemotherapy, and removal of one or both testes. Burdette, supra at 151.

Despite the need for accurate staging of prostate cancer, current staging methodology is limited. The wide variety of biological behavior displayed by neoplasms of the prostate has resulted in considerable difficulty in predicting and assessing the course of prostate cancer. Augustus et al., supra at 47. Indeed, despite the fact that most prostate cancer patients have carcinomas that are of intermediate grade and stage, prognosis for these types of carcinomas is highly variable. Andrew A Renshaw & Christopher L. Corless, *Prognostic Features in the Pathology of Prostate Cancer, in Prostate Cancer: A Multidisciplinary Guide* 26 (Philip W. Kantoff et al. eds. 1997). Techniques such as transrectal ultrasound, abdominal and pelvic computerized tomography, and MRI have not been particularly useful in predicting local tumor extension. D'Amico, supra at 53 (editors' comment). While the use of serum PSA in combination with the Gleason score is currently the most effective method of staging prostate cancer, id., PSA is of limited predictive value, Augustus et al., supra at 47; Renshaw et al., supra at 26, and the Gleason score is prone to variability and error, King, C. R. & Long, J. P., *Int'l. J. Cancer* 90(6): 326-30 (2000). As such, the current focus of prostate cancer research has been to obtain biomarkers to help better assess the progression of the disease. Augustus et al., supra at 47; Renshaw et al., supra at 26; Pettaway, C. A., *Tech. Urol.* 4(1): 35-42 (1998).

Accordingly, there is a great need for more sensitive and accurate methods for predicting whether a person is likely to develop prostate cancer, for diagnosing prostate cancer, for monitoring the progression of the disease, for staging the prostate cancer, for determining whether the prostate cancer has metastasized and for imaging the prostate cancer. There is also a need for better treatment of prostate cancer.

Colon Cancer

Colorectal cancer is the second most common cause of cancer death in the United States and the third most prevalent cancer in both men and women. M. L. Davila & A. D. Davila, *Screening for Colon and Rectal Cancer, in Colon and Rectal Cancer* 47 (Peter S. Edelstein ed., 2000). Colorectal cancer is categorized as a digestive system cancer by the American Cancer Society (ACS) which also includes cancers of the esophagus, stomach, small intestine, anus, anal canal, anorectum, liver & intrahepatic bile duct, gallbladder & other biliary, pancreas, and other digestive organs. The ACS estimates that there will be about 263,060 new cases of digestive system cancers in 2006 in the United States alone. Digestive system cancers will cause an estimated 136,180 deaths combined in the United States in 2006. Specifically, The ACS estimates that there will be about 104,950 new cases of colon cancer, 40,340 new cases of rectal cancer and 5,420 new cases of small intestine cancer in the 2005 in the United States alone. Colon, rectal and small intestine cancers will cause an estimated 57,360 deaths combined in the United States in 2005. ACS Website: cancer with the extension .org of the world wide web. Nearly all cases of colorectal cancer arise from adenomatous polyps, some of which mature into large polyps, undergo abnormal growth and development, and ultimately progress into cancer. Davila at 55-56. This progression would appear to take at least 10 years in most patients, rendering it a readily treatable form of cancer if diagnosed early, when the cancer is localized. Davila at 56; Walter J. Burdette, *Cancer: Etiology, Diagnosis, and Treatment* 125 (1998).

Although our understanding of the etiology of colon cancer is undergoing continual refinement, extensive research in this area points to a combination of factors, including age, hereditary and nonhereditary conditions, and environmental/dietary factors. Age is a key risk factor in the development of colorectal cancer, Davila at 48, with men and women over 40 years of age become increasingly susceptible to that cancer, Burdette at 126. Incidence rates increase considerably in each subsequent decade of life. Davila at 48. A number of hereditary and nonhereditary conditions have also been linked to a heightened risk of developing colorectal cancer, including familial adenomatous polyposis (FAP), hereditary nonpolyposis colorectal cancer (Lynch syndrome or HNPCC), a personal and/or family history of colorectal cancer or adenomatous polyps, inflammatory bowel disease, diabetes mellitus, and obesity. Id. at 47; Henry T. Lynch & Jane F. Lynch, *Hereditary Nonpolyposis Colorectal Cancer (Lynch Syndromes), in Colon and Rectal Cancer* 67-68 (Peter S. Edelstein ed., 2000).

Environmental/dietary factors associated with an increased risk of colorectal cancer include a high fat diet, intake of high dietary red meat, and sedentary lifestyle. Davila at 47; Reddy, B. S., *Prev. Med.* 16(4): 460-7 (1987). Conversely, environmental/dietary factors associated with a reduced risk of colorectal cancer include a diet high in fiber, folic acid, calcium, and hormone-replacement therapy in post-menopausal women. Davila at 50-55. The effect of antioxidants in reducing the risk of colon cancer is unclear. Davila at 53.

Because colon cancer is highly treatable when detected at an early, localized stage, screening should be a part of routine care for all adults starting at age 50, especially those with first-degree relatives with colorectal cancer. One major advantage of colorectal cancer screening over its counterparts in other types of cancer is its ability to not only detect precancerous lesions, but to remove them as well. Davila at 56. The key colorectal cancer screening tests in use today are fecal occult blood test, sigmoidoscopy, colonoscopy, double-contrast barium enema, and the carcinoembryonic antigen (CEA) test. Burdette at 125; Davila at 56.

The fecal occult blood test (FOBT) screens for colorectal cancer by detecting the amount of blood in the stool, the premise being that neoplastic tissue, particularly malignant tissue, bleeds more than typical mucosa, with the amount of bleeding increasing with polyp size and cancer stage. Davila at 56-57. While effective at detecting early stage tumors, FOBT is unable to detect adenomatous polyps (premalignant lesions), and, depending on the contents of the fecal sample, is subject to rendering false positives. Davila at 56-59. Sigmoidoscopy and colonoscopy, by contrast, allow direct visualization of the bowel, and enable one to detect, biopsy, and remove adenomatous polyps. Davila at 59-60, 61. Despite the advantages of these procedures, there are accompanying downsides: sigmoidoscopy, by definition, is limited to the sigmoid colon and below, colonoscopy is a relatively expensive procedure, and both share the risk of possible bowel perforation and hemorrhaging. Davila at 59-60. Double-contrast barium enema (DCBE) enables detection of lesions better than FOBT, and almost as well a colonoscopy, but it may be limited in evaluating the winding rectosigmoid region. Davila at 60. The CEA blood test, which involves screening the blood for carcinoembryonic antigen, shares the downside of FOBT, in that it is of limited utility in detecting colorectal cancer at an early stage. Burdette at 125.

Once colon cancer has been diagnosed, treatment decisions are typically made in reference to the stage of cancer progression. A number of techniques are employed to stage the cancer (some of which are also used to screen for colon cancer), including pathologic examination of resected colon, sigmoidoscopy, colonoscopy, and various imaging techniques. *AJCC Cancer Staging Handbook* 84 (Irvin D. Fleming et al. eds., 5$^{th}$ ed. 1998); Montgomery, R. C. and Ridge, J. A., *Semin. Surg. Oncol.* 15(3): 143-150 (1998). Moreover, chest films, liver functionality tests, and liver scans are employed to determine the extent of metastasis. Fleming at 84. While computerized tomography and magnetic resonance imaging are useful in staging colorectal cancer in its later stages, both have unacceptably low staging accuracy for identifying early stages of the disease, due to the difficulty that both methods have in (1) revealing the depth of bowel wall tumor infiltration and (2) diagnosing malignant adenopathy. Thoeni, R. F., *Radiol. Clin. N. Am.* 35(2): 457-85 (1997). Rather, techniques such as transrectal ultrasound (TRUS) are preferred in this context, although this technique is inaccurate with respect to detecting small lymph nodes that may contain metastases. David Blumberg & Frank G. Opelka, *Neoadjuvant and Adjuvant Therapy for Adenocarcinoma of the Rectum, in Colon and Rectal Cancer* 316 (Peter S. Edelstein ed., 2000). Several classification systems have been devised to stage the extent of colorectal cancer, including the Dukes' system and the more detailed International Union against Cancer-American Joint Committee on Cancer TNM staging system, which is considered by many in the field to be a more useful staging system. Burdette at 126-27. The TNM system, which is used for either clinical or pathological staging, is divided into four stages, each of which evaluates the extent of cancer growth with respect to primary tumor (T), regional lymph nodes (N), and distant metastasis (M). Fleming at 84-85. The system focuses on the extent of tumor invasion into the intestinal wall, invasion of adjacent structures, the number of regional lymph nodes that have been affected, and whether distant metastasis has occurred. Fleming at 81.

Stage 0 is characterized by in situ carcinoma (Tis), in which the cancer cells are located inside the glandular basement membrane (intraepithelial) or lamina propria (intramucosal). In this stage, the cancer has not spread to the regional lymph nodes (N0), and there is no distant metastasis (M0). In stage I, there is still no spread of the cancer to the regional lymph nodes and no distant metastasis, but the tumor has invaded the submucosa (T1) or has progressed further to invade the muscularis propria (T2). Stage II also involves no spread of the cancer to the regional lymph nodes and no distant metastasis, but the tumor has invaded the subserosa, or the nonperitonealized pericolic or perirectal tissues (T3), or has progressed to invade other organs or structures, and/or has perforated the visceral peritoneum (T4). Stage III is characterized by any of the T substages, no distant metastasis, and either metastasis in 1 to 3 regional lymph nodes (N1) or metastasis in four or more regional lymph nodes (N2). Lastly, stage IV involves any of the T or N substages, as well as distant metastasis. Fleming at 84-85; Burdette at 127.

Currently, pathological staging of colon cancer is preferable over clinical staging as pathological staging provides a more accurate prognosis. Pathological staging typically involves examination of the resected colon section, along with surgical examination of the abdominal cavity. Fleming at 84. Clinical staging would be a preferred method of staging were it at least as accurate as pathological staging, as it does not depend on the invasive procedures of its counterpart.

Turning to the treatment of colorectal cancer, surgical resection results in a cure for roughly 50% of patients. Irradiation is used both preoperatively and postoperatively in treating colorectal cancer. Chemotherapeutic agents, particularly 5-fluorouracil, are also powerful weapons in treating colorectal cancer. Other agents include irinotecan and floxuridine, cisplatin, levamisole, methotrexate, interferon-α, and leucovorin. Burdette at 125, 132-33. Nonetheless, thirty to forty percent of patients will develop a recurrence of colon cancer following surgical resection, which in many patients is the ultimate cause of death. Wayne De Vos, *Follow-up After Treatment of Colon Cancer, Colon and Rectal Cancer* 225 (Peter S. Edelstein ed., 2000). Accordingly, colon cancer patients must be closely monitored to determine response to therapy and to detect persistent or recurrent disease and metastasis.

The next few paragraphs describe the some of molecular bases of colon cancer. In the case of FAP, the tumor suppressor gene APC (adenomatous polyposis coli), chromosomally located at 5q21, has been either inactivated or deleted by mutation. Alberts et al., *Molecular Biology of the Cell* 1288 (3d ed. 1994). The APC protein plays a role in a number of functions, including cell adhesion, apoptosis, and repression of the c-myc oncogene. N. R. Hall & R. D. Madoff, *Genetics and the Polyp-Cancer Sequence, Colon and Rectal Cancer* 8 (Peter S. Edelstein, ed., 2000). Of those patients with colorectal cancer who have normal APC genes, over 65% have such mutations in the cancer cells but not in other tissues. Alberts et al., supra at 1288. In the case of HPNCC, patients manifest abnormalities in the tumor suppressor gene HNPCC, but only about 15% of tumors contain the mutated gene. Id. A host of other genes have also been implicated in colorectal cancer, including the K-ras, N-ras, H-ras and c-myc oncogenes, and the tumor suppressor genes DCC (deleted in colon carcinoma) and p53. Hall & Madoff, supra at 8-9; Alberts et al., supra at 1288.

Abnormalities in Wg/Wnt signal transduction pathway are also associated with the development of colorectal carcinoma. Taipale, J. and Beachy, P. A. *Nature* 411: 349-354 (2001). Wnt1 is a secreted protein gene originally identified within mouse mammary cancers by its insertion into the mouse mammary tumor virus (MMTV) gene. The protein is homologous to the wingless (Wg) gene product of Drosophila, in which it functions as an important factor for the determination of dorsal-ventral segmentation and regulates the formation of fly imaginal discs. Wg/Wnt pathway controls cell proliferation, death and differentiation. Taipal (2001). There are at least 13 members in the Wnt family. These proteins have been found expressed mainly in the central nervous system (CNS) of vertebrates as well as other tissues such as mammary and intestine. The Wnt proteins are the ligands for a family of seven transmembrane domain receptors related to the Frizzled gene product in Drosophila. Binding Wnt to Frizzled stimulates the activity of the downstream target, Disheveled, which in turn inactivates the glycogen synthetase kinase 3β (GSK3β). Taipal (2001). Usually active GSK3β will form a complex with the adenomatous polyposis coli (APC) protein and phosphorylate another complex member, β-catenin. Once phosphorylated, β-catenin is directed to degradation through the ubiquitin pathway. When GSK3β or APC activity is down regulated, β-catenin is accumulated in the cytoplasm and binds to the T-cell factor or lymphocyte excitation factor (Tcf/Lef) family of transcriptional factors. Binding of β-catenin to Tcf releases the transcriptional repression and induces gene transcription. Among the genes regulated by β-catenin are a transcriptional repressor Engrailed, a transforming growth factor-β (TGF-β) family member Decapentaplegic, and the cytokine Hedgehog in Drosophila. β-Catenin also involves in regulating cell adhesion by binding to α-catenin and E-cadherin. On the other hand, binding of β-catenin to these proteins controls the cytoplasmic β-catenin level and its complexing with TCF. Taipal (2001). Growth factor stimulation and activation of c-src or v-src also regulate β-catenin level by phosphorylation of α-catenin and its related protein, $p120^{cas}$. When phosphorylated, these proteins decrease their binding to E-cadherin and β-catenin resulting in the accumulation of cytoplasmic β-catenin. Reynolds, A. B. et al. Mol. Cell Biol. 14: 8333-8342 (1994). In colon cancer, c-src enzymatic activity has been shown increased to the level of v-src. Alternation of components in the Wg/Wnt pathway promotes colorectal carcinoma development. The best known modifications are to the APC gene. Nicola S et al. Hum. Mol. Genet 10:721-733 (2001). This germline mutation causes the appearance of hundreds to thousands of adenomatous polyps in the large bowel. It is the gene defect that accounts for the autosomally dominantly inherited FAP and related syndromes. The molecular alternations that occur in this pathway largely involve deletions of alleles of tumor-suppressor genes, such as APC, p53 and Deleted in Colorectal Cancer (DCC), combined with mutational activation of proto-oncogenes, especially c-Ki-ras. Aoki, T. et al. Human Mutat. 3: 342-346 (1994). All of these lead to genomic instability in colorectal cancers.

Another source of genomic instability in colorectal cancer is the defect of DNA mismatch repair (MMR) genes. Human homologues of the bacterial mutHLS complex (hMSH2, hMLHI, hPMS1, hPMS2 and hMSH6), which is involved in the DNA mismatch repair in bacteria, have been shown to cause the HNPCC (about 70-90% HNPCC) when mutated. Modrich, P. and Lahue, R. Ann Rev. Biochem. 65: 101-133 (1996); and Peltomaki, P. Hum. Mol. Genet 10: 735-740 (2001). The inactivation of these proteins leads to the accumulation of mutations and causes genetic instability that represents errors in the accurate replication of the repetitive mono-, di-, tri- and tetra-nucleotide repeats, which are scattered throughout the genome (microsatellite regions). Jass, J. R. et al. J. Gastroenterol Hepatol 17: 17-26 (2002). Like in the classic FAP, mutational activation of c-Ki-ras is also required for the promotion of MSI in the alternative HNPCC. Mutations in other proteins such as the tumor suppressor protein phosphatase PTEN (Zhou, X. P. et al. Hum. Mol. Genet 11: 445-450 (2002)), BAX (Buttler, L. M. Aus. N. Z. J. Surg. 69: 88-94 (1999)), Caspase-5 (Planck, M. Cancer Genet Cytogenet. 134: 46-54 (2002)), TGFβ-RII (Fallik, D. et al. Gastroenterol Clin Biol. 24: 917-22 (2000)) and IGFII-R (Giovannucci E. J. Nutr. 131: 3109S-20S (2001)) have also been found in some colorectal tumors possibly as the cause of MMR defect.

Some tyrosine kinases have been shown up-regulated in colorectal tumor tissues or cell lines like HT29. Skoudy, A. et al. Biochem J. 317 (Pt 1): 279-84 (1996). Focal adhesion kinase (FAK) and its up-stream kinase c-src and c-yes in colonic epithelia cells may play an important role in the promotion of colorectal cancers through the extracellular matrix (ECM) and integrin-mediated signaling pathways. Jessup, J. M. et al., The molecular biology of colorectal carcinoma, in: The Molecular Basis of Human Cancer, 251-268 (Coleman W. B. and Tsongalis G. J. Eds. 2002). The formation of c-src/FAK complexes may coordinately deregulate VEGF expression and apoptosis inhibition. Recent evidences suggest that a specific signal-transduction pathway for cell survival that implicates integrin engagement leads to FAK activation and thus activates PI-3 kinase and akt. In turn, akt phosphorylates BAD and blocks apoptosis in epithelial cells. The activation of c-src in colon cancer may induce VEGF expression through the hypoxia pathway. Other genes that may be implicated in colorectal cancer include Cox enzymes (Ota, S. et al. Aliment Pharmacol. Ther. 16 (Suppl 2): 102-106 (2002)), estrogen (al-Azzawi, F. and Wahab, M. Climacteric 5: 3-14 (2002)), peroxisome proliferator-activated receptor-γ (PPAR-γ) (Gelman, L. et al. Cell Mol. Life Sci. 55: 932-943 (1999)), IGF-I (Giovannucci (2001)), thymine DNA glycosylase (TDG) (Hardeland, U. et al. Prog. Nucleic Acid Res. Mol. Biol. 68: 235-253 (2001)) and EGF (Mendelsohn, J. Endocrine-Related Cancer 8: 3-9 (2001)).

Gene deletion and mutation are not the only causes for development of colorectal cancers. Epigenetic silencing by DNA methylation also accounts for the lost of function of colorectal cancer suppressor genes. A strong association between MSI and CpG island methylation has been well characterized in sporadic colorectal cancers with high MSI but not in those of hereditary origin. In one experiment, DNA methylation of MLH1, CDKN2A, MGMT, THBS1, RARB, APC, and p14ARF genes has been shown in 80%, 55%, 23%, 23%, 58%, 35%, and 50% of 40 sporadic colorectal cancers with high MSI respectively. Yamamoto, H. et al. Genes Chromosomes Cancer 33: 322-325 (2002); and Kim, K. M. et al. Oncogene. 12; 21(35): 5441-9 (2002). Carcinogen metabolism enzymes such as GST, NAT, CYP and MTHFR are also associated with an increased or decreased colorectal cancer risk. Pistorius, S. et al. Kongressbd Dtsch Ges Chir Kongr 118: 820-824 (2001); and Potter, J. D. J. Natl. Cancer Inst. 91: 916-932 (1999).

From the foregoing, it is clear that procedures used for detecting, diagnosing, monitoring, staging, prognosticating, and preventing the recurrence of colorectal cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop colorectal cancer, for diagnosing colorectal cancer, for monitoring the progression of the disease, for staging the colorectal cancer, for determining whether the colorectal cancer has metastasized, and for imaging the colorectal cancer. Following accurate diagnosis, there is also a need for less invasive and more effective treatment of colorectal cancer.

In addition to prostate and digestive tract cancers, there is great need for improved methods and compounds for the detection, diagnosis, prognosis, imaging, determination of metastases and metastatic potential, monitoring, staging and treatment of lung, liver, pancreatic, bone and esophagus cancers.

Angiogenesis in Cancer

Growth and metastasis of solid tumors are also dependent on angiogenesis. Folkman, J., 1986, *Cancer Research*, 46, 467-473; Folkman, J., 1989, *Journal of the National Cancer Institute*, 82, 4-6. It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone. Weidner, N., et al., 1991, *The New England Journal of Medicine*, 324(1), 1-8.

Angiogenesis, defined as the growth or sprouting of new blood vessels from existing vessels, is a complex process that primarily occurs during embryonic development. The process is distinct from vasculogenesis, in that the new endothelial cells lining the vessel arise from proliferation of existing cells, rather than differentiating from stem cells. The process is invasive and dependent upon proteolysis of the extracellular matrix (ECM), migration of new endothelial cells, and synthesis of new matrix components. Angiogenesis occurs during embryogenic development of the circulatory system; however, in adult humans, angiogenesis only occurs as a response to a pathological condition (except during the reproductive cycle in women).

Under normal physiological conditions in adults, angiogenesis takes place only in very restricted situations such as hair growth and wounding healing. Auerbach, W. and Auerbach, R., 1994, *Pharmacol Ther.* 63(3):265-3 11; Ribatti et al., 1991, *Haematologica* 76(4):3 11-20; Risau, 1997, *Nature* 386(6626):67 1-4. Angiogenesis progresses by a stimulus which results in the formation of a migrating column of endothelial cells. Proteolytic activity is focused at the advancing tip of this "vascular sprout", which breaks down the ECM sufficiently to permit the column of cells to infiltrate and migrate. Behind the advancing front, the endothelial cells differentiate and begin to adhere to each other, thus forming a new basement membrane. The cells then cease proliferation and finally define a lumen for the new arteriole or capillary.

Unregulated angiogenesis has gradually been recognized to be responsible for a wide range of disorders, including, but not limited to, cancer, cardiovascular disease, rheumatoid arthritis, psoriasis and diabetic retinopathy. Folkman, 1995, *Nat Med* 1(1):27-31; Isner, 1999, *Circulation* 99(13): 1653-5; Koch, 1998, *Arthritis Rheum* 41(6):951-62; Walsh, 1999, *Rheumatology* (Oxford) 38(2):103-12; Ware and Simons, 1997, *Nat Med* 3(2): 158-64.

Of particular interest is the observation that angiogenesis is required by solid tumors for their growth and metastases. Folkman, 1986 supra; Folkman 1990, *J Natl. Cancer Inst.*, 82(1) 4-6; Folkman, 1992, *Semin Cancer Biol* 3(2):65-71; Zetter, 1998, *Annu Rev Med* 49:407-24. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. The precise mechanisms that control the angiogenic switch is not well understood, but it is believed that neovascularization of tumor mass results from the net balance of a multitude of angiogenesis stimulators and inhibitors Folkman, 1995, supra.

One of the most potent angiogenesis inhibitors is endostatin identified by O'Reilly and Folkman. O'Reilly et al., 1997, *Cell* 88(2):277-85; O'Reilly et al., 1994, *Cell* 79(2):3 15-28. Its discovery was based on the phenomenon that certain primary tumors can inhibit the growth of distant metastases. O'Reilly and Folkman hypothesized that a primary tumor initiates angiogenesis by generating angiogenic stimulators in excess of inhibitors. However, angiogenic inhibitors, by virtue of their longer half life in the circulation, reach the site of a secondary tumor in excess of the stimulators. The net result is the growth of primary tumor and inhibition of secondary tumor. Endostatin is one of a growing list of such angiogenesis inhibitors produced by primary tumors. It is a proteolytic fragment of a larger protein: endostatin is a 20 kDa fragment of collagen XVIII (amino acid H1132-K1315 in murine collagen XVIII). Endostatin has been shown to specifically inhibit endothelial cell proliferation in vitro and block angiogenesis in vivo. More importantly, administration of endostatin to tumor-bearing mice leads to significant tumor regression, and no toxicity or drug resistance has been observed even after multiple treatment cycles. Boehm et al., 1997, Nature 390(6658):404-407. The fact that endostatin targets genetically stable endothelial cells and inhibits a variety of solid tumors makes it a very attractive candidate for anticancer therapy. Fidler and Ellis, 1994, Cell 79(2):185-8; Gastl et al., 1997, Oncology 54(3):177-84; Hinsbergh et al., 1999, Ann Oncol 10 Suppl 4:60-3. In addition, angiogenesis inhibitors have been shown to be more effective when combined with radiation and chemotherapeutic agents. Klement, 2000, J. Clin Invest, 105(8) R15-24. Browder, 2000, Cancer Res. 6-(7) 1878-86, Arap et al., 1998, Science 279(5349): 377-80; Mauceri et al., 1998, Nature 394(6690):287-91.

As discussed above, each of the methods for diagnosing and staging prostate, colon, lung or pancreas cancer is limited by the technology employed. Accordingly, there is need for sensitive molecular and cellular markers for the detection of prostate, colon, lung or pancreas cancer. There is a need for molecular markers for the accurate staging, including clinical and pathological staging, of prostate, colon, lung or pancreas cancers to optimize treatment methods. In addition, there is a need for sensitive molecular and cellular markers to monitor the progress of cancer treatments, including markers that can detect recurrence of prostate, colon, lung or pancreas cancers following remission.

The present invention provides alternative methods of treating prostate, colon, lung or pancreas cancer that overcome the limitations of conventional therapeutic methods as well as offer additional advantages that will be apparent from the detailed description below.

SUMMARY OF THE INVENTION

This invention is directed to an isolated Pro115 antibody that binds to Pro115 on a mammalian cell. The invention is further directed to an isolated Pro115 antibody that internalizes upon binding to Pro115 on a mammalian cell. The antibody may be a monoclonal antibody. Alternatively, the antibody is an antibody fragment or a chimeric or a humanized antibody. The monoclonal antibody may be produced by a hybridoma selected from the group of hybridomas deposited under American Type Culture Collection on 19 May 2006 comprising Pro115.B7.1 and Pro115.B34.1.

The antibody may compete for binding to the same epitope as the epitope bound by the monoclonal antibody produced by a hybridoma selected from the group of hybridomas deposited under the American Type Culture Collection on 19 May 2006 comprising Pro115.B7.1 and Pro115.B34.1.

The invention is also directed to conjugated antibodies. They may be conjugated to a growth inhibitory agent or a cytotoxic agent. The cytotoxic agent may be selected from the group consisting of toxins, antibiotics, radioactive isotopes and nucleolytic enzymes and toxins. Examples of toxins include, but are not limited to, maytansin, maytansinoids, saporin, gelonin, ricin or calicheamicin.

The mammalian cell may be a cancer cell. Preferably, the anti-Pro115 monoclonal antibody that inhibits the growth of Pro115-expressing cancer cells.

The antibody may be produced in bacteria. Alternatively, the antibody may be a humanized form of an anti-Pro115 antibody produced by a hybridoma selected from the group of hybridomas deposited with the ATCC on 19 May 2006 comprising Pro115.B7.1 and Pro115.B34.1.

Preferably, the cancer is selected from the group consisting of prostate, colon, lung and pancreas cancer. The invention is also directed to a method of producing the antibodies comprising culturing an appropriate cell and recovering the antibody from the cell culture.

The invention is also directed to compositions comprising the antibodies and a carrier. The antibody may be conjugated to a cytotoxic agent. The cytotoxic agent may be a radioactive isotope or other chemotherapeutic agent.

The invention is also directed to a method of killing an Pro115-expressing cancer cell, comprising contacting the cancer cell with the antibodies of this invention, thereby killing the cancer cell. The cancer cell may be selected from the group consisting of prostate, colon, lung and pancreas cancer cell.

The prostate, colon, lung or pancreas may be metastatic cancer. The invention is also directed to a method of alleviating an Pro115-expressing cancer in a mammal, comprising administering a therapeutically effective amount of the antibodies to the mammal.

In addition, the invention is directed to an article of manufacture comprising a container and a composition contained therein, wherein the composition comprises an antibody as described herein. The article of manufacture may also comprise an additional component, e.g., a package insert indicating that the composition can be used to treat prostate, colon, lung or pancreas cancer.

BRIEF DESCRIPTION OF THE FIGURES

FIG. 1 shows an alignment between human Pro 115 (SEQ ID NO: 66), mouse Pro115 (SEQ ID NO:67) other human members of the TMPRSS family including TMPRSS1 (SEQ ID NO:68), TMPRSS3 (SEQ ID NO:69), TMPRSS4 (SEQ ID NO:70), TMPRSS5 (SEQ ID NO:71), TMPRSS6 (SEQ ID NO:72), TMPRSS7 (SEQ ID NO:73), TMPRSS9 (SEQ ID NO:74), TMPRSS10 (SEQ ID NO:75), TMPRSS13 (SEQ ID NO:76) and TMPRSS12 (SEQ ID NO:77).

DETAILED DESCRIPTION OF THE INVENTION

Definitions and General Techniques

Human "Pro115" as used herein, refers to a serine protease protein of 492 amino acids that is expressed on the cell surface, whose nucleotide and amino acid sequences are disclosed wholly or in part in e.g., U.S. Pat. No. 6,043,033, U.S. Pat. No. 6,350,448 and US publication 20020119531 as HUPAP; U.S. Pat. No. 7,037,667 as 20P1F12/TMPRSS2 gene (also designated as 20P1F12-GTC1); WO 00/12758 A1 as sequence giβ2507612|gb|U75329.1|HSU75329 Human serine protease mRNA, complete CDS; U.S. Pat. No. 6,902,892 as Pro115; and WO 00/00605 A1 as TMPRSS2; the disclosures of which are hereby expressly incorporated by reference. Amino acids 106-492 of Pro115 are expressed on the cell surface. Additionally, Pro115 is shed from the cell surface and is present in intercellular matrix and bodily fluids. Amino acids 106-492, or 225-492 (autocleaved protease domain) of Pro115 are present in intercellular matrix and bodily fluids. Pro115 as used herein includes allelic variants and conservative substitution mutants of the protein which have Pro115 biological activity. Specifically, Pro115 includes SNP variants described herein.

Pro115 is related to the family of transmembrane serine proteases and is identified in the RefSeq database as accessions NM_005656 and NP_005647 (accessible at ncbi with the extension .nlm.nih.gov of the world wide web) and titled "Homo sapiens transmembrane protease, serine 2 (TMPRSS2)". Other synonyms for Pro115 include: PRSS10 and human epitheliasin. The refseq database includes the following summary of Pro115:

This gene encodes a protein that belongs to the serine protease family. The encoded protein contains a type II transmembrane domain, a receptor class A domain, a scavenger receptor cysteine-rich domain and a protease domain. Serine proteases are known to be involved in many physiological and pathological processes. This gene was demonstrated to be up-regulated by androgenic hormones in prostate cancer cells and down-regulated in androgen-independent prostate cancer tissue. The protease domain of this protein is thought to be cleaved and secreted into cell media after autocleavage. The biological function of this gene is unknown.

Several publications have described the identification, characterization, association with carcinomas, and clinical development of Pro115 as a molecular target for cancer therapy, diagnosis and vaccination including the following which are hereby incorporated by reference in their entirety.

Tu JJ, et al. Gene fusions between TMPRSS2 and ETS family genes in prostate cancer: frequency and transcript variant analysis by RT-PCR and FISH on paraffin-embedded tissues. Mod Pathol. 2007 Jul 13; [Epub ahead of print]

Yoshimoto M et al. Microdeletion and concurrent translocation associated with a complex TMPRSS2: ERG prostate cancer gene fusion.
Genes Chromosomes Cancer. 2007 Sep; 46(9): 861-3.

Moore-Scott BA, et al. Identification of molecular markers that are expressed in discrete anterior-posterior domains of the endoderm from the gastrula stage to mid-gestation.
Dev Dyn. 2007 Jul; 236(7): 1997-2003.
Perner S, et al. TMPRSS2-ERG fusion prostate cancer: an early molecular event associated with invasion.
Am J Surg Pathol. 2007 Jun; 31(6): 882-8.
Mostaghel EA, et al. Intraprostatic androgens and androgen-regulated gene expression persist after testosterone suppression: therapeutic implications for castration-resistant prostate cancer.
Cancer Res. 2007 May 15; 67(10): 5033-41.
Cai C, et al. ETV1 Is a Novel Androgen Receptor-Regulated Gene That Mediates Prostate Cancer Cell Invasion.
Mol Endocrinol. 2007 May 15; [Epub ahead of print]
Schroder FH. Re: Recurrent fusion of TMPRSS2 and ETS transcription factor genes in prostate cancer.
Eur Urol. 2007 May; 51(5): 1443-4.
Billis A. Morphological features of TMPRSS2: ERG fusion prostate cancer.
Int Braz J Urol. 2007 Mar-Apr; 33(2): 282-3.
Billis A. Are there morphologic correlates of prostate cancer associated with TMPRSS2-ERG molecular abnormalities?
Int Braz J Urol. 2007 Mar-Apr; 33(2): 281-2.
Saramaki O, Visakorpi T. Chromosomal aberrations in prostate cancer.
Front Biosci. 2007 May 1; 12: 3287-301.
Perner S, et al. [TMPRSS2-ETS gene fusion in prostate cancer.]
Urologe A. 2007 Jul; 46(7): 754-760.
Teixeira MR. Recurrent fusion oncogenes in carcinomas.
Crit Rev Oncog. 2006 Dec; 12(3-4): 257-71. Review.
Nelson WG. Prostate cancer prevention.
Curr Opin Urol. 2007 May; 17(3): 157-67. Review.
Mertz KD, et al. Molecular characterization of TMPRSS2-ERG gene fusion in the NCI-H660 prostate cancer cell line: a new perspective for an old model.
Neoplasia. 2007 Mar; 9(3): 200-6.
Winnes M, et al. Molecular genetic analyses of the TMPRSS2-ERG and TMPRSS2-ETV1 gene fusions in 50 cases of prostate cancer.
Oncol Rep. 2007 May; 17(5): 1033-6.
Mosquera JM, et al. Morphological features of TMPRSS2-ERG gene fusion prostate cancer.
J Pathol. 2007 May; 212(1): 91-101.
Yoo NJ, et al. Absence of fusion of TMPRSS2 and ETS transcription factor genes in gastric and colorectal carcinomas.
APMIS. 2007 Mar; 115(3): 252-3.
Mehra R, et al. Comprehensive assessment of TMPRSS2 and ETS family gene aberrations in clinically localized prostate cancer.
Mod Pathol. 2007 May; 20(5): 538-44. Epub 2007 Mar 2.
Lapointe J, et al. A variant TMPRSS2 isoform and ERG fusion product in prostate cancer with implications for molecular diagnosis.
Mod Pathol. 2007 Apr; 20(4): 467-73. Epub 2007 Mar 2.
Rajput AB, et al. Frequency of the TMPRSS2: ERG gene fusion is increased in moderate to poorly differentiated prostate cancers.
J Clin Pathol. 2007 Jan 26; [Epub ahead of print]
Demichelis F, et al. TMPRSS2: ERG gene fusion associated with lethal prostate cancer in a watchful waiting cohort.
Oncogene. 2007 Jul 5; 26(31): 4596-9. Epub 2007 Jan 22.
Macaluso M, Giordano A. TMPRSS2: ERG gene fusion a new genetic marker for prostate cancer progression.
Cancer Biol Ther. 2007 Jan; 6(1): 46-7.
Nami RK, et al. Expression of TMPRSS2: ERG gene fusion in prostate cancer cells is an important prognostic factor for cancer progression.
Cancer Biol Ther. 2007 Jan; 6(1): 40-5.
Hermans KG, et al. TMPRSS2: ERG fusion by translocation or interstitial deletion is highly relevant in androgen-dependent prostate cancer, but is bypassed in late-stage androgen receptor-negative prostate cancer.
Cancer Res. 2006 Nov 15; 66(22): 10658-63.
Iljin K, et al. TMPRSS2 fusions with oncogenic ETS factors in prostate cancer involve unbalanced genomic rearrangements and are associated with HDAC1 and epigenetic reprogramming.
Cancer Res. 2006 Nov 1; 66(21): 10242-6.
Laxman B, et al. Noninvasive detection of TMPRSS2: ERG fusion transcripts in the urine of men with prostate cancer.
Neoplasia. 2006 Oct; 8(10): 885-8.
Clark J, et al. Diversity of TMPRSS2-ERG fusion transcripts in the human prostate.
Oncogene. 2007 Apr 19; 26(18): 2667-73. Epub 2006 Oct 16.
Cerveira N, et al. TMPRSS2-ERG gene fusion causing ERG overexpression precedes chromosome copy number changes in prostate carcinomas and paired HGPIN lesions.
Neoplasia. 2006 Oct; 8(10): 826-32.
Kantoff P. Prevention, complementary therapies, and new scientific developments in the field of prostate cancer.
Rev Urol. 2006; 8 Suppl 2: S9-S14.
Rubin MA, Chinnaiyan AM. Bioinformatics approach leads to the discovery of the TMPRSS2: ETS gene fusion in prostate cancer.
Lab Invest. 2006 Nov; 86(11): 1099-102. Epub 2006 Sep 18.
Jia L, et al. Locus-wide chromatin remodeling and enhanced androgen receptor-mediated transcription in recurrent prostate tumor cells.

Mol Cell Biol. 2006 Oct; 26(19): 7331-41.
Bottcher E, et al. Proteolytic activation of influenza viruses by serine proteases TMPRSS2 and HAT from human airway epithelium.
J Virol. 2006 Oct; 80(19): 9896-8.
Wang J, et al. Expression of Variant TMPRSS2/ERG Fusion Messenger RNAs Is Associated with Aggressive Prostate Cancer.
Cancer Res. 2006 Sep 1; 66(17): 8347-51.
Perner S, et al. TMPRSS2: ERG Fusion-Associated Deletions Provide Insight into the Heterogeneity of Prostate Cancer.
Cancer Res. 2006 Sep 1; 66(17): 8337-41.
Liu W, et al. Comprehensive assessment of DNA copy number alterations in human prostate cancers using Affymetrix 100K SNP mapping array.
Genes Chromosomes Cancer. 2006 Nov; 45(11): 1018-32.
Yoshimoto M, Jos et al. Three-Color FISH Analysis of TMPRSS2/ERG Fusions in Prostate Cancer Indicates That Genomic Microdeletion of Chromosome 21 Is Associated with Rearrangement.
Neoplasia. 2006 Jun; 8(6): 465-9.
Tomlins SA, et al. TMPRSS2: ETV4 gene fusions define a third molecular subtype of prostate cancer.
Cancer Res. 2006 Apr 1; 66(7): 3396-400.
Soller MJ, et al. Confirmation of the high frequency of the TMPRSS2/ERG fusion gene in prostate cancer.
Genes Chromosomes Cancer. 2006 Jul; 45(7): 717-9.
Ahlers CM, Figg WD. ETS-TMPRSS2 fusion gene products in prostate cancer.
Cancer Biol Ther. 2006 Mar; 5(3): 254-5. Epub 2006 Mar 13.
Kim TS, et al. Phenotypic analysis of mice lacking the Tmprss2-encoded protease.
Mol Cell Biol. 2006 Feb; 26(3): 965-75.
Chen Y, et al. Elevated expression and potential roles of human Sp5, a member of Sp transcription factor family, in human cancers.
Biochem Biophys Res Commun. 2006 Feb 17; 340(3): 758-66. Epub 2005 Dec 20.
Tomlins SA, et al. Recurrent fusion of TMPRSS2 and ETS transcription factor genes in prostate cancer.
Science. 2005 Oct 28; 310(5748): 644-8.
Schalken JA, et al. Molecular prostate cancer pathology: current issues and achievements.
Scand J Urol Nephrol Suppl. 2005 May; (216): 82-93.
O'Leary DA, et al. Tissue-specific overexpression of the HSA21 gene GABPalpha: implications for DS.
Biochim Biophys Acta. 2004 Dec 24; 1739(1): 81-7.
Wilson S, et al. The membrane-anchored serine protease, TMPRSS2, activates PAR-2 in prostate cancer cells.
Biochem J. 2005 Jun 15; 388(Pt 3): 967-72.
Hessels D, et al. Applicability of biomarkers in the early diagnosis of prostate cancer.
Expert Rev Mol Diagn. 2004 Jul; 4(4): 513-26.
Lubieniecka JM, et al. Met160Val polymorphism in the TRMPSS2 gene and risk of prostate cancer in a population-based case-control study.
Prostate. 2004 Jun 1; 59(4): 357-9.
Hartel A, et al. Characterisation of gene expression patterns in 22RV1 cells for determination of environmental androgenic/antiandrogenic compounds.
J Steroid Biochem Mol Biol. 2003 Feb; 84(2-3): 231-8.
Wu Q. Type II transmembrane serine proteases.
Curr Top Dev Biol. 2003; 54: 167-206.
Aimes RT, et al. Endothelial cell serine proteases expressed during vascular morphogenesis and angiogenesis.
Thromb Haemost. 2003 Mar; 89(3): 561-72.
Yun Kim S, et al. Detection of site-specific proteolysis in secretory pathways.
Biochem Biophys Res Commun. 2002 Aug 16; 296(2): 419-24.
Donaldson SH, et al. Regulation of the epithelial sodium channel by serine proteases in human airways.
J Biol Chem. 2002 Mar 8; 277(10): 8338-45. Epub 2001 Dec 26.
Vaarala MH, et al. The TMPRSS2 gene encoding transmembrane serine protease is overexpressed in a majority of prostate cancer patients: detection of mutated TMPRSS2 form in a case of aggressive disease.
Int J Cancer. 2001 Dec 1; 94(5): 705-10.
Yamaguchi N, et al. Spinesin/TMPRSS5, a novel transmembrane serine protease, cloned from human spinal cord.
J Biol Chem. 2002 Mar 1; 277(9): 6806-12. Epub 2001 Dec 12.
Davisson MT, et al. Evolutionary breakpoints on human chromosome 21.
Genomics. 2001 Nov; 78(1-2): 99-106.
Teng DH, et al. Mutation analyses of 268 candidate genes in human tumor cell lines.
Genomics. 2001 Jun 15; 74(3): 352-64.
Pletcher MT, et al. Use of comparative physical and sequence mapping to annotate mouse chromosome 16 and human chromosome 21.
Genomics. 2001 May 15; 74(1): 45-54.
Jacquinet E, et al. Cloning and characterization of the cDNA and gene for human epitheliasin.
Eur J Biochem. 2001 May; 268(9): 2687-99.
Afar DE, et al. Catalytic cleavage of the androgen-regulated TMPRSS2 protease results in its secretion by prostate and prostate cancer epithelia.
Cancer Res. 2001 Feb 15; 61(4): 1686-92.
Vaarala MH, et al. Expression of transmembrane serine protease TMPRSS2 in mouse and human tissues.

J Pathol. 2001 Jan; 193(1): 134-40.
Jacquinet E, et al. Cloning, genomic organization, chromosomal assignment and expression of a novel mosaic serine proteinase: epitheliasin.
FEBS Lett. 2000 Feb 18; 468(1): 93-100.
Lin B, et al. Prostate-localized and androgen-regulated expression of the membrane-bound serine protease TMPRSS2.
Cancer Res. 1999 Sep 1; 59(17): 4180-4.
Hildmann T, et al. A contiguous 3-Mb sequence-ready map in the S3-MX region on 21q22.2 based on high-throughput nonisotopic library screenings.
Genome Res. 1999 Apr; 9(4): 360-72.
Paoloni-Giacobino A, et al. Cloning of the TMPRSS2 gene, which encodes a novel serine protease with transmembrane, LDLRA, and SRCR domains and maps to 21q22.3.
Genomics. 1997 Sep 15; 44(3): 309-20. Erratum in: Genomics 2001 Sep; 77(1-2): 114.

As described in the publications above, Pro115 is membrane protease that is differentially expressed in prostate, colon and other cancers versus normal tissues. Pro115 biological activity includes protease activity, protease-activated receptor 2 (PAR-2) activation, sodium channel regulation, fusion protein production, regulation or promotion of carcinogenesis, tumorigenesis, cell differentiation, migration, vascular morphogenesis or angiogenesis.

Expression of Pro115, and the increased protease activity, has protective effects for cells (e.g. cancer cells) and confers a survival benefit. Autocleavage and secretion of the active protease domain into the surrounding matrix of a tumor promotes growth, migration and metastases of Pro115 expressing tumors. Inhibition of Pro115 activity prevents tumor growth and spread.

It has also been shown that due to mutations and genomic rearrangements Pro115 is mutated or part of fusion genes in prostate cancer.

Recently, several publications have described gene fusions between TMPRSS2 (Pro115) and transcription factors of the ETS family, commonly ERG and ETV1. These gene fusions are due to genomic rearrangement or intronic deletion and have been described as markers of cancer prognosis, progression, differentiation, invasion and morphology. Pro115 fusion proteins produced by these gene fusions are alternative embodiments of Pro115. Specifically, any fusion protein containing a portion of the Pro115 protein (e.g. TMPRSS2-ERG, TMPRSS2-ETV1) is encompassed by the herein description of Pro115 and antibodies thereto.

Taken together, the differential expression in cancer, protease activity, and role in cellular processes make Pro115 a promising target for diagnosis and immunotherapy of prostate and other tumor types. Anti-Pro115 antibodies are useful in diagnostic or therapeutic applications alone or in combination with molecules against other TMPRSS family members, serine proteases and growth factors and their receptors (e.g. VEGF, EGFR).

The antibodies of the instant invention, those described previously and herein, specifically bind Pro115 and have demonstrated characteristics which make them ideal therapeutic candidates for modulating Pro115 functions including protease activity, protease-activated receptor 2 (PAR-2) activation, sodium channel regulation, fusion protein production, regulation or promotion of carcinogenesis, tumorigenesis, cell differentiation, migration, vascular morphogenesis or angiogenesis. Furthermore, the antibodies of the instant invention are useful as therapeutic agents for those suffering from prostate, colon, lung or pancreas cancers. The antibodies may have therapeutic effect by killing Pro115 expressing cancer cells, inhibiting growth of Pro115 expressing tumors, shrinking Pro115 expressing tumors, extending survival time of individuals with Pro115 expressing tumors, reducing metastases of Pro115 expressing tumors, inducing immune response against Pro115 expressing tumors or reducing angiogenesis or vascularization of Pro115 expressing tumors.

The term "antibody" (Ab) as used herein includes monoclonal antibodies, polyclonal antibodies, multispecific antibodies (e.g. bispecific antibodies), and antibody fragments, as long as they exhibit the desired biological activity. The term "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for [L and F isotypes. Each 6 L chain has at the N-terminus, a variable domain (VL) followed by a constant domain (CL) at its other end.

The VL is aligned with the VH and the CL is aligned with the first constant domain of the heavy chain (CHl).

Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parsiow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. They γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (LI), 5056 (L2) and 89-97 (L3) in the VL, and around about 1-35 (HI), 50-65 (H2) and 95-102 (113) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (LI), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies.

The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a CL and at least heavy chain constant domains, CHI, CH2 and CH3. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, N.Y., pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993). Furthermore, effects of linker sequence alterations in engineering bispecific tandem diabodies are described in Le Gall et al., Protein Eng Des Sel. 17(4):357-66 (2004).

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of Pro115 will possess at least about 70% homology with the native sequence Pro115, preferably, at least about 80%, more preferably at least about 85%, even more preferably at least about 90% homology, and most preferably at least 95%. The amino acid sequence variants can possess substitutions, deletions, insertions and/or alterations due to allelic variation or Single Nucleotide Polymorphisms (SNPs) within the native nucleic acid sequence encoding the amino acid sequence.

Several definitions of SNPs exist. See, e.g., Brooks, 235 Gene 177-86 (1999). As used herein, the term "single nucleotide polymorphism" or "SNP" includes all single base variants, thus including nucleotide insertions and deletions in addition to single nucleotide substitutions and any resulting amino acid variants due to codon alteration. There are two types of nucleotide substitutions. A transition is the replacement of one purine by another purine or one pyrimidine by another pyrimidine. A transversion is the replacement of a purine for a pyrimidine, or vice versa.

Numerous methods exist for detecting SNPs within a nucleotide sequence. A review of many of these methods can be found in Landegren et al., 8 Genome Res. 769-76 (1998). For example, a SNP in a genomic sample can be detected by preparing a Reduced Complexity Genome (RCG) from the genomic sample, then analyzing the RCG for the presence or absence of a SNP. See, e.g., WO 00/18960. Multiple SNPs in a population of target polynucleotides in parallel can be detected using, for example, the methods of WO 00/50869. Other SNP detection methods include the methods of U.S. Pat. Nos. 6,297,018 and 6,322,980. Furthermore, SNPs can be detected by restriction fragment length polymorphism (RFLP) analysis. See, e.g., U.S. Pat. Nos. 5,324,631; 5,645, 995. RFLP analysis of SNPs, however, is limited to cases where the SNP either creates or destroys a restriction enzyme cleavage site. SNPs can also be detected by direct sequencing of the nucleotide sequence of interest. In addition, numerous assays based on hybridization have also been developed to detect SNPs and mismatch distinction by polymerases and ligases. Several web sites provide information about SNPs including Ensembl (ensembl with the extension .org of the world wide web), Sanger Institute (sanger with the extension .ac.uk/genetics/exon/ of the world wide web), National Center for Biotechnology Information (NCBI) (ncbi with the extension .nlm.nih.gov/SNP/ of the world wide web), The SNP Consortium Ltd. (snp.cshl.org). The chromosomal locations for the compositions disclosed herein are provided below. In addition, one of ordinary skill in the art could perform a search against the genome or any of the databases cited above using BLAST to find the chromosomal location or locations of SNPs. Another a preferred method to find the genomic coordinates and associated SNPs would be to use the BLAT tool (genome.ucsc.edu, Kent et al. 2001, The Human Genome Browser at UCSC, Genome Research 996-1006 or Kent 2002 BLAT, The BLAST-Like Alignment Tool Genome Research, 1-9). All web sites above were accessed Dec. 3, 2003.

Preferred amino acid sequence variants of Pro115 are described in the table below. The polynucleotides encoding the amino acids of the present invention were analyzed and single nucleotide polymorphism (SNP) attributes were identified. Specifically identified were SNPs occurring the coding region of the nucleotide, the Alleles of the SNP, the nucleotide ambiguity code for the SNP, the position in the codon of the SNP if within the Open Reading Frame (1, 2, 3 or UTR for untranslated regions), and the SNP type (synonymous or non-synonymous to the protein translation). In addition to the attributes above, the SNP rs#ID for the NCBI SNP database (dbSNP) which is accessible at ncbi with the extension .nlm-.nih.gov/SNP/ of the world wide web is referenced for each SNP. Additional single nucleotide polymorphism (SNP) information can be accessed at the databases listed above.

The table below includes the polynucleotide target, dbSNP rs#ID, Nucleic acid residue affected by the SNP (Polynucleotide) in NM_005656, SNP alleles, Nucleotide ambiguity code, Condon Position of the SNP if within the ORF (1, 2, 3 or UTR if not within ORF), and the SNP type (synonymous "syn" or non-synonymous "non-syn"), Amino acid residue affected by the SNP (AA Residue) in NP_005647, and the Alternate amino acid residue.

| | dbSNP rs# ID | Nucleic Acid Residue | Alleles | Ambiguity Code | Codon Pos | SNP type | Amino Acid Residue | Alternate Amino Acid |
|---|---|---|---|---|---|---|---|---|
| Pro115 | 28532009 | 162 | G/A | R | 2 | Non-syn | 12 | G/E |
| Pro115 | 3787950 | 352 | A/G | R | 3 | Syn | 75 | T/T |
| Pro115 | 12329760 | 605 | G/A | R | 1 | Non-syn | 160 | M/V |
| Pro115 | 17854725 | 895 | T/C | Y | 3 | Syn | 256 | I/I |
| Pro115 | 2298659 | 904 | C/T | Y | 3 | Syn | 259 | G/G |
| Pro115 | 2298658 | 919 | G/A | R | 3 | Syn | 264 | P/P |
| Pro115 | 1056602 | 1474 | G/C | S | 3 | Non-syn | 449 | K/N |

Variants of Pro115 as described above or in the literature and antibodies which bind to these variants are part of the invention described herein.

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

"Homology" is defined as the percentage of residues in the amino acid sequence variant that are identical after aligning the sequences and introducing gaps, if necessary, to achieve the maximum percent homology. Methods and computer programs for the alignment are well known in the art. Sequence similarity may be measured by any common sequence analysis algorithm, such as GAP or BESTFIT or other variation Smith-Waterman alignment. See, T. F. Smith and M. S. Waterman, J. Mol. Biol. 147:195-197 (1981) and W. R. Pearson, Genomics 11:635-650 (1991).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

As used herein, an anti-Pro115 antibody that "internalizes" is one that is taken up by (i.e., enters) the cell upon binding to Pro115 on a mammalian cell (i.e. cell surface Pro115). The internalizing antibody will of course include antibody fragments, human or humanized antibody and antibody conjugate. For therapeutic applications, internalization in vivo is contemplated. The number of antibody molecules internalized will be sufficient or adequate to kill an Pro115-expressing cell, especially an Pro115-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

Whether an anti-Pro115 antibody internalizes upon binding Pro115 on a mammalian cell can be determined by various assays including those described in the experimental examples below. For example, to test internalization in vivo, the test antibody is labeled and introduced into an animal known to have Pro115 expressed on the surface of certain cells. The antibody can be radiolabeled or labeled with fluorescent or gold particles, for instance. Animals suitable for this assay include a mammal such as a NCR nude mouse that contains a human Pro115-expressing tumor transplant or xenograft, or a mouse into which cells transfected with human Pro115 have been introduced, or a transgenic mouse expressing the human Pro115 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising Pro115-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the Pro115-expressing cell in vivo, the faster the desired killing or growth inhibitory effect on the target Pro115-expressing cell can be achieved, e.g., by a cytotoxic immunoconjugate. Preferably, the kinetics of internalization of the anti-Pro115 antibodies are such that they favor rapid killing of the Pro115-expressing target cell. Therefore, it is desirable that the anti-Pro115 antibody exhibit a rapid rate of internalization preferably, within 24 hours from administration of the antibody in vivo, more preferably within about 12 hours, even more preferably within about 30 minutes to 1 hour, and most preferably, within about 30 minutes. The present invention provides antibodies that internalize as fast as about 15 minutes from the time of introducing the anti-Pro115 antibody in vivo. The antibody will preferably be internalized into the cell within a few hours upon binding to Pro115 on the cell surface, preferably within 1 hour, even more preferably within 15-30 minutes.

To determine if a test antibody can compete for binding to the same epitope as the epitope bound by the anti-Pro115 antibodies of the present invention including the antibodies produced by the hybridomas deposited with the ATCC, a cross-blocking assay e.g., a competitive ELISA assay can be performed. In an exemplary competitive ELISA assay, Pro115-coated wells of a microtiter plate, or Pro115-coated sepharose beads, are pre-incubated with or without candidate competing antibody and then a biotin-labeled anti-Pro115 antibody of the invention is added. The amount of labeled anti-Pro115 antibody bound to the Pro115 antigen in the wells or on the beads is measured using avidin-peroxidase conjugate and appropriate substrate.

Alternatively, the anti-Pro115 antibody can be labeled, e.g., with a radioactive or fluorescent label or some other detectable and measurable label. The amount of labeled anti-Pro115 antibody that binds to the antigen will have an inverse correlation to the ability of the candidate competing antibody (test antibody) to compete for binding to the same epitope on the antigen, i.e., the greater the affinity of the test antibody for the same epitope, the less labeled anti-Pro115 antibody will be bound to the antigen-coated wells. A candidate competing antibody is considered an antibody that binds substantially to the same epitope or that competes for binding to the same epitope as an anti-Pro115 antibody of the invention if the candidate competing antibody can block binding of the anti-Pro115 antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

An antibody having a "biological characteristic" of a designated antibody, such as any of the monoclonal antibodies Pro115.A1, Pro115.A2, Pro115.A3, Pro115.A4, Pro115.A5, Pro115.A6, Pro115.A7, Pro115.A8, Pro115.A9, Pro115.A10, Pro115.A11, Pro115.A12, Pro115.A13, Pro115.A14, Pro115.A15, Pro115.A16, Pro115.A17, Pro115.A18, Pro115.A19, Pro115.A20, Pro115A21, Pro115.A22, Pro115.A23, Pro115.A24, Pro115.A25, Pro115.A101.1, Pro115.A102.1, Pro115.A103.1, Pro115.A104.1, Pro115.A106.1, Pro115.A107.1, Pro115.A108.1, Pro115.B1, Pro115.B2, Pro115.B3, Pro115.B4, Pro115.B5, Pro115.B6, Pro115.B7, Pro115.B8, Pro115.B9, Pro115.B10, Pro115.B11, Pro115.B12, Pro115.B13, Pro115.B14, Pro115.B15, Pro115.B16, Pro115.B17, Pro115.B18, Pro115.B19, Pro 115.B20, Pro115.B21, Pro115.B22, Pro115.B23, Pro115.B24, Pro115.B25, Pro115.B26, Pro115.B27, Pro115.B28, Pro115.B29, Pro115.B30, Pro115.B31, Pro115.B32, Pro115.B33, Pro115.B34, Pro115.B35, Pro115.B36, Pro115.B37, Pro115.B38, Pro115.B39, Pro115.B40, Pro115.B41, Pro115.B42, Pro115.B43, Pro115.B44, Pro115.B45, Pro115.B46, Pro115.B47, Pro115.B48, Pro115.B49, Pro115.B50, Pro115.B51, Pro115.B52, Pro115.B53, Pro115.B54, Pro115.B55, Pro115.B56, Pro115.B57, Pro115.B58, Pro115.B59, Pro115.B60, Pro115.B61, Pro115.B62, Pro115.B63, Pro115.B64, Pro115.B65, Pro115.B66, Pro115.B67, Pro115.B68, Pro115.B69, Pro115.D1, Pro 115.D2, Pro 115.D3, Pro115.D4, Pro115.D5, Pro115.D6, Pro115.D7, Pro115.D8, Pro115.D9, Pro115.D10, Pro115.D11, Pro115.D12, Pro115.D13, Pro115.F2 and Pro115.F3, is one which possesses one or more of the biological characteristics of that antibody which distinguish it from other antibodies that bind to the same antigen, Pro115.A1, Pro115.A2, Pro115.A3, Pro115.A4, Pro115.A5, Pro115.A6, Pro115.A7, Pro115.A8, Pro115.A9, Pro115.A10, Pro115.A11, Pro115.A12, Pro115.A13, Pro115.A14, Pro115.A15, Pro115.A16, Pro115.A17, Pro115.A18, Pro115.A19, Pro115.A20, Pro115.A21, Pro115.A22, Pro115.A23, Pro115.A24, Pro115.A25, Pro115.A101.1, Pro115.A102.1, Pro115.A103.1, Pro115.A104.1, Pro115.A106.1, Pro115.A107.1, Pro115.A108.1, Pro115.B1, Pro115.B2, Pro115.B3, Pro115.B4, Pro115.B5, Pro115.B6, Pro115.B7, Pro115.B8, Pro115.B9, Pro115.B10, Pro115.B11, Pro115.B12, Pro115.B13, Pro115.B14, Pro115.B15, Pro115.B16, Pro115.B17, Pro115.B18, Pro115.B19, Pro115.B20, Pro115.B21, Pro115.B22, Pro115.B23, Pro115.B24, Pro115.B25, Pro115.B26, Pro115.B27, Pro115.B28, Pro115.B29, Pro115.B30, Pro115.B31, Pro115.B32, Pro115.B33, Pro115.B34, Pro115.B35, Pro115.B36, Pro115.B37, Pro115.B38, Pro115.B39, Pro115.B40, Pro115.B41, Pro115.B42, Pro115.B43, Pro115.B44, Pro115.B45, Pro115.B46, Pro115.B47, Pro115.B48, Pro115.B49, Pro115.B50, Pro115.B51, Pro115.B52, Pro115.B53, Pro115.B54, Pro115.B55, Pro115.B56, Pro115.B57, Pro115.B58, Pro115.B59, Pro115.B60, Pro115.B61, Pro115.B62, Pro115.B63, Pro115.B64, Pro115.B65, Pro115.B66, Pro115.B67, Pro115.B68, Pro115.B69, Pro115.D1, Pro115.D2, Pro115.D3, Pro115.D4, Pro115.D5, Pro115.D6, Pro115.D7, Pro115.D8, Pro115.D9, Pro115.D10, Pro115.D11, Pro115.D12, Pro115.D13, Pro115.F2 and Pro115.F3 will bind the same epitope as that bound by Pro115.A1, Pro 115.A2, Pro115.A3, Pro115.A4, Pro115.A5, Pro115.A6, Pro115.A7, Pro115.A8, Pro115.A9, Pro115.A10, Pro115.A11, Pro115.A12, Pro115.A13, Pro115.A14, Pro115.A15, Pro115.A16, Pro115.A17, Pro115.A18, Pro115.A19, Pro115.A20, Pro115.A21, Pro115.A22, Pro115.A23, Pro115.A24, Pro115.A25, Pro115.A101.1, Pro115.A102.1, Pro115.A103.1, Pro115.A104.1, Pro115.A106.1, Pro115.A107.1, Pro115.A108.1, Pro115.B1, Pro115.B2, Pro115.B3, Pro115.B4, Pro115.B5, Pro115.B6, Pro115.B7, Pro115.B8, Pro115.B9, Pro115.B10, Pro115.B11, Pro115.B12, Pro115.B13, Pro115.B14, Pro115.B15, Pro115.B16, Pro115.B17, Pro115.B18, Pro115.B19, Pro115.B20, Pro115.B21, Pro115.B22, Pro115.B23, Pro115.B24, Pro115.B25, Pro115.B26, Pro115.B27, Pro115.B28, Pro115.B29, Pro115.B30, Pro115.B31, Pro115.B32, Pro115.B33, Pro115.B34, Pro115.B35, Pro115.B36, Pro115.B37, Pro115.B38, Pro115.B39, Pro115.B40, Pro115.B41, Pro115.B42, Pro115.B43, Pro115.B44, Pro115.B45, Pro115.B46, Pro115.B47, Pro115.B48, Pro115.B49, Pro115.B50, Pro115.B51, Pro115.B52, Pro115.B53, Pro115.B54, Pro115.B55, Pro115.B56, Pro115.B57, Pro115.B58, Pro115.B59, Pro115.B60, Pro115.B61, Pro115.B62, Pro115.B63, Pro115.B64, Pro115.B65, Pro115.B66, Pro115.B67, Pro115.B68, Pro115.B69, Pro115.D1, Pro115.D2, Pro115.D3, Pro115.D4, Pro115.D5, Pro115.D6, Pro115.D7, Pro115.D8, Pro115.D9, Pro115.D10, Pro115.D11, Pro115.D12, Pro115.D13, Pro115.F2 and Pro115.F3 (e.g. which competes for binding or blocks binding of monoclonal antibody Pro115.A1, Pro115.A2, Pro115.A3, Pro115.A4, Pro115.A5, Pro115.A6, Pro115.A7, Pro115.A8, Pro115.A9, Pro115.A10, Pro115.A11, Pro115.A12, Pro115.A13, Pro115.A14, Pro115.A15, Pro115.A16, Pro115.A17, Pro115.A18, Pro115.A19, Pro115.A20, Pro115.A21, Pro115.A22, Pro115.A23, Pro115.A24, Pro115.A25, Pro115.A101.1, Pro115.A102.1, Pro115.A103.1, Pro115.A104.1, Pro115.A106.1, Pro115.A107.1, Pro115.A108.1, Pro115.B1, Pro115.B2, Pro115. B3, Pro115.B4, Pro115.B5, Pro115.B6, Pro115.B7, Pro115.B8, Pro115.B9, Pro115.B10, Pro115.B11, Pro115.B12, Pro115.B13, Pro115.B14, Pro115.B15, Pro115.B16, Pro115.B17, Pro115.B18, Pro115.B19, Pro115.B20, Pro115.B21, Pro115.B22, Pro115.B23, Pro115.B24, Pro115.B25, Pro115.B26, Pro115.B27, Pro115.B28, Pro115.B29, Pro115.B30, Pro115.B31, Pro115.B32, Pro115.B33, Pro115.B34, Pro115.B35, Pro115.B36, Pro115.B37, Pro115.B38, Pro115.B39, Pro115.B40, Pro115.B41, Pro115.B42, Pro115.B43, Pro115.B44, Pro115.B45, Pro115.B46, Pro115.B47, Pro115.B48, Pro115.B49, Pro115.B50, Pro115.B51, Pro115.B52, Pro115.B53, Pro115.B54, Pro115.B55, Pro115.B56, Pro115.B57, Pro115.B58, Pro115.B59, Pro115.B60, Pro115.B61, Pro115.B62, Pro115.B63, Pro115.B64, Pro115.B65, Pro115.B66, Pro115.B67, Pro115.B68, Pro115.B69, Pro115.D1, Pro115.D2, Pro115.D3, Pro115.D4, Pro115.D5, Pro115.D6, Pro115.D7, Pro115.D8, Pro115.D9, Pro115.D10, Pro115.D11, Pro115.D12, Pro115.D13, Pro115.F2 and Pro115.F3), be able to target an Pro115-expressing tumor in vivo and may internalize upon binding to Pro115 on a mammalian cell in vivo. Likewise, an antibody with the biological characteristic of the Pro115.A1, Pro115.A2, Pro115.A3, Pro115.A4, Pro115.A5, Pro115.A6, Pro115.A7, Pro115.A8, Pro115.A9, Pro115.A10, Pro115.A11, Pro115.A12, Pro115.A13, Pro115.A14, Pro115.A15, Pro115.A16, Pro115.A17, Pro115.A18, Pro115.A19, Pro115.A20, Pro115.A21, Pro115.A22, Pro115.A23, Pro115.A24, Pro115.A25, Pro115.A101.1, Pro115.A102.1, Pro115.A103.1, Pro115.A104.1, Pro115.A106.1, Pro115.A107.1, Pro115.A108.1, Pro115.B1, Pro115.B2, Pro115.B3, Pro115.B4, Pro115.B5, Pro115.B6, Pro115.B7, Pro115.B8, Pro115.B9, Pro115.B10, Pro115.B11, Pro115.B12, Pro115.B13, Pro115.B14, Pro115.B15, Pro115.B16, Pro115.B17, Pro115.B18, Pro115.B19, Pro115.B20, Pro115.B21, Pro115.B22, Pro115.B23, Pro115.B24, Pro115.B25, Pro115.B26, Pro115.B27, Pro115.B28, Pro115.B29, Pro115.B30, Pro115.B31, Pro115.B32, Pro115.B33, Pro115.B34, Pro115.B35, Pro115.B36, Pro115.B37, Pro115.B38, Pro115.B39, Pro115.B40, Pro115.B41, Pro115.B42, Pro115.B43, Pro115.B44, Pro115.B45, Pro115.B46, Pro115.B47, Pro115.B48, Pro115.B49, Pro115.B50, Pro115.B51, Pro115.B52, Pro115.B53, Pro115.B54, Pro115.B55, Pro115.B56, Pro115.B57, Pro115.B58, Pro115.B59, Pro115.B60, Pro115.B61, Pro115.B62, Pro115.B63, Pro115.B64, Pro115.B65, Pro115.B66, Pro115.B67, Pro115.B68, Pro115.B69, Pro115.D1, Pro115.D2, Pro115.D3, Pro 115.D4, Pro115.D5, Pro115.D6, Pro115.D7, Pro115.D8, Pro115.D9, Pro115.D10, Pro115.D11, Pro115.D12, Pro115.D13, Pro115.F2 and Pro115.F3 antibody will have the same epitope binding, targeting, internalizing, tumor growth inhibitory and cytotoxic properties of the antibody.

The term "antagonist" antibody is used in the broadest sense, and includes an antibody that partially or fully blocks, inhibits, or neutralizes a biological activity of a native Pro115 protein disclosed herein. Methods for identifying antagonists of an Pro115 polypeptide may comprise contacting an Pro115 polypeptide or a cell expressing Pro115 on the cell surface, with a candidate antagonist antibody and measuring a detectable change in one or more biological activities normally associated with the Pro115 polypeptide.

The term 'agonistic" antibody is used in the broadest sense, and includes an antibody the partially or fully promotes, activates, or increases biological activity of Pro115. Additionally, an agonistic antibody may mimic an Pro115 binding partner (e.g. receptor or ligand) wherein binding of the Pro115 antibody has substantially the same effect on biologic activity of Pro115 as binding of the binding partner. Methods for identifying agonists of an Pro115 polypeptide may comprise contacting an Pro115 polypeptide or a cell expressing Pro115 on the cell surface, with a candidate agonistic antibody and measuring a detectable change in one or more biological activities normally associated with the Pro115 polypeptide.

An "antibody that inhibits the growth of tumor cells expressing Pro115" or a "growth inhibitory" antibody is one which binds to and results in measurable growth inhibition of cancer cells expressing or overexpressing Pro115. Preferred growth inhibitory anti-Pro115 antibodies inhibit growth of Pro115-expressing tumor cells (e.g., prostate, colon, lung or pancreas cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 pg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-Pro115 antibody at about 1 pg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses Pro115. Preferably the cell is a tumor cell, e.g. an ovarian, colon, prostate, or lung cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cells in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); complement dependent cytotoxicity (CDC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126.330-41 (1995). Other FcRs, including those to be identified in the future, are encompassed by the term "FcR" herein. The term also includes the neonatal receptor, FcRn, which is responsible for the transfer, of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996) may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

A "Pro115-expressing cell" is a cell which expresses endogenous or transfected Pro115 on the cell surface. A "Pro115-expressing cancer" is a cancer comprising cells that have Pro115 protein present on the cell surface. A "Pro115-expressing cancer" produces sufficient levels of Pro115 on the surface of cells thereof, such that an anti-Pro115 antibody can bind thereto and have a therapeutic effect with respect to the cancer. A cancer which "overexpresses" Pro115 is one which has higher levels of Pro115 at the cell surface thereof, compared to a noncancerous cell of the same tissue type. Such overexpression may be caused by gene amplification or by increased transcription or translation. Pro115 overexpression may be determined in a diagnostic or prognostic assay by evaluating increased levels of the Pro115 protein present on the surface of a cell (e.g. via an immunohistochemistry assay; FACS analysis). Alternatively, or additionally, one may measure levels of Pro115-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). One may also study Pro115 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. A Pro115-expressing cancer includes prostate, colon, lung or pancreas cancer.

A "mammal" for purposes of treating a cancer or alleviating the symptoms of cancer, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an Pro115-expressing cancer if, after receiving a therapeutic amount of an anti-Pro115 antibody according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-Pro115 antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR).

The term "therapeutically effective amount" refers to an amount of an antibody or a drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed.

Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially a Pro 115-expressing cancer cell, either in vitro or in vivo. Thus, the growth inhibitory agent may be one which significantly reduces the percentage of Pro115-expressing cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest GI also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "epitope tagged" used herein refers to a chimeric polypeptide comprising an anti-Pro115 antibody polypeptide fused to a "tag polypeptide". The tag polypeptide has enough residues to provide an epitope against which an antibody can be made, yet is short enough such that it does not interfere with activity of the Ig polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid molecule" is a nucleic acid molecule, e.g., an RNA, DNA, or a mixed polymer, which is substantially separated from other genome DNA sequences as well as proteins or complexes such as ribosomes and polymerases, which naturally accompany a native sequence. The term embraces a nucleic acid molecule which has been removed from its naturally occurring environment, and includes recombinant or cloned DNA isolates and chemically synthesized analogues or analogues biologically synthesized by heterologous systems. A substantially pure nucleic acid molecule includes isolated forms of the nucleic acid molecule.

"Vector" includes shuttle and expression vectors and includes, e.g., a plasmid, cosmid, or phagemid. Typically, a plasmid construct will also include an origin of replication (e.g., the ColEl origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in prokaryotic, e.g., bacterial, or eukaryotic cells. Suitable vectors are disclosed below.

The cell that produces an anti-Pro115 antibody of the invention will include the parent hybridoma cell e.g., the hybridomas that are deposited with the ATCC, as well as bacterial and eukaryotic host cells into which nucleic acid encoding the antibodies have been introduced. Suitable host cells are disclosed below.

RNA interference refers to the process of sequence-specific post transcriptional gene silencing in animals mediated by short interfering RNAs (siRNA) (Fire et al., 1998, Nature, 391, 806). The corresponding process in plants is commonly referred to as post transcriptional gene silencing or RNA silencing and is also referred to as quelling in fungi. The process of post transcriptional gene silencing is thought to be an evolutionarily conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double stranded RNAs (dsRNA) derived from viral infection or the random integration of transposon elements into a host genome via a cellular response that specifically destroys homologous single stranded RNA or viral genomic RNA. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409, 363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

Short interfering RNA mediated RNAi has been studied in a variety of systems. Fire et al., 1998, Nature, 391, 806, were the first to observe RNAi in *C. Elegans*. Wianny and Goetz, 1999, Nature Cell Biol., 2, 70, describe RNAi mediated by dsRNA in mouse embryos. Hammond et al., 2000, Nature, 404, 293, describe RNAi in *Drosophila* cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, EMBO J., 20, 6877) has revealed certain requirements for siRNA length, structure, chemical composition, and sequence that are essential to mediate efficient RNAi activity. These studies have shown that 21 nucleotide siRNA duplexes are most active when containing two nucleotide 3'-overhangs. Furthermore, complete substitution of one or both siRNA strands with 2'-deoxy(2'-H) or 2'-O-methyl nucleotides abolishes RNAi activity, whereas substitution of the 3'-terminal siRNA overhang nucleotides with deoxynucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309).

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, EMBO J., 20, 6877). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 both suggest that siRNA "may include modifications to either the phosphate-sugar back bone or the nucleoside to include at least one of a nitrogen or sulfur heteroatom", however neither application teaches to what extent these modifications are tolerated in siRNA molecules nor provide any examples of such modified siRNA. Kreutzer and Limmer, Canadian Patent Application No. 2,359,180, also describe certain chemical modifications for use in dsRNA constructs in order to counteract activation of double stranded-RNA-dependent protein kinase PKR, specifically 2'-amino or 2'-O-methyl nucleotides, and nucleotides containing a 2'-O or 4'-C methylene bridge. However, Kreutzer and Limmer similarly fail to show to what extent these modifications are tolerated in siRNA molecules nor do they provide any examples of such modified siRNA.

Parrish et al., 2000, Molecular Cell, 6, 1977-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that "RNAs with two (phosphorothioate) modified bases also had substantial decreases in effectiveness as RNAi triggers (data not shown); (phosphorothioate) modification of more than two residues greatly destabilized the RNAs in vitro and we were not able to assay interference activities." Id. at 1081. The authors also tested certain modifications at the 2'-position of the nucleotide sugar in the long siRNA transcripts and observed that substituting deoxynucleotides for ribonucleotides "produced a substantial decrease in interference activity", especially in the case of Uridine to Thymidine and/or Cytidine to deoxy-Cytidine substitutions. Id. In addition, the authors tested certain base modifications, including substituting 4-thiouracil, 5-bromouracil, 5-iodouracil, 3-(aminoallyl) uracil for uracil, and inosine for guanosine in sense and antisense strands of the siRNA, and found that whereas 4-thiouracil and 5-bromouracil were all well tolerated, inosine "produced a substantial decrease in interference activity" when incorporated in either strand. Incorporation of 5-iodouracil and 3-(aminoallyl)uracil in the antisense strand resulted in substantial decrease in RNAi activity as well.

Beach et al., International PCT Publication No. WO 01/68836, describes specific methods for attenuating gene expression using endogenously derived dsRNA. Tuschl et al., International PCT Publication No. WO 01/75164, describes a *Drosophila* in vitro RNAi system and the use of specific siRNA molecules for certain functional genomic and certain therapeutic applications; although Tuschl, 2001, Chem. Biochem., 2, 239-245, doubts that RNAi can be used to cure genetic diseases or viral infection due "to the danger of activating interferon response". Li et al., International PCT Publication No. WO 00/44914, describes the use of specific dsR-NAs for use in attenuating the expression of certain target genes. Zernicka-Goetz et al., International PCT Publication No. WO 01/36646, describes certain methods for inhibiting the expression of particular genes in mammalian cells using certain dsRNA molecules. Fire et al., International PCT Publication No. WO 99/32619, describes particular methods for introducing certain dsRNA molecules into cells for use in inhibiting gene expression. Plaetinck et al., International PCT Publication No. WO 00/01846, describes certain methods for identifying specific genes responsible for conferring a particular phenotype in a cell using specific dsRNA molecules. Mello et al., International PCT Publication No. WO 01/29058, describes the identification of specific genes involved in dsRNA mediated RNAi. Deschamps Depaillette et al., International PCT Publication No. WO 99/07409, describes specific compositions consisting of particular dsRNA molecules combined with certain anti-viral agents. Driscoll et al., International PCT Publication No. WO 01/49844, describes specific DNA constructs for use in facilitating gene silencing in targeted organisms. Parrish et al., 2000, Molecular Cell, 6, 1977-1087, describes specific chemically modified siRNA constructs targeting the unc-22 gene of *C. elegans*. Tuschl et al., International PCT Publication No. WO 02/44321, describe certain synthetic siRNA constructs.

Compositions and Methods of the Invention

The invention provides anti-Pro115 antibodies. Preferably, the anti-Pro115 antibodies internalize upon binding to cell surface Pro115 on a mammalian cell. The anti-Pro115 antibodies may also destroy or lead to the destruction of tumor cells bearing Pro115.

It was not apparent that Pro115 was internalization-competent. In addition the ability of an antibody to internalize depends on several factors including the affinity, avidity, and isotype of the antibody, and the epitope that it binds. We have demonstrated herein that the cell surface Pro115 is internalization competent upon binding by the anti-Pro115 antibodies of the invention. Additionally, it was demonstrated that the anti-Pro115 antibodies of the present invention can specifically target Pro115-expressing tumor cells. These tumor targeting, internalization and growth inhibitory properties of the anti-Pro115 antibodies make these antibodies very suitable for therapeutic uses, e.g., in the treatment of various cancers including prostate, colon, lung or pancreas cancer. Internalization of the anti-Pro115 antibody is preferred, e.g., if the antibody or antibody conjugate has an intracellular site of action and if the cytotoxic agent conjugated to the antibody does not readily cross the plasma membrane (e.g., the toxin calicheamicin). Internalization is not necessary if the antibodies or the agent conjugated to the antibodies do not have intracellular sites of action, e.g., if the antibody can kill the tumor cell by ADCC or some other mechanism.

The anti-Pro115 antibodies of the invention also have various non-therapeutic applications. The anti-Pro115 antibodies of the present invention can be useful for diagnosis and staging of Pro115-expressing cancers (e.g., in radioimaging). They may be used alone or in combination with other ovarian cancer markers, including, but not limited to, CA125, HE4 and mesothelin. The antibodies are also useful for purification or immunoprecipitation of Pro115 from cells, for detection and quantitation of Pro115 in vitro, e.g. in an ELISA or a Western blot, to kill and eliminate Pro115-expressing cells from a population of mixed cells as a step in the purification of other cells. The internalizing anti-Pro115 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

The antibody may compete for binding, or binds substantially to, the same epitope bound by the antibodies of the invention. Antibodies having the biological characteristics of the present anti-Pro115 antibodies of the invention are also contemplated, e.g., an anti-Pro115 antibody which has the biological characteristics of a monoclonal antibody produced by the hybridomas deposited with the ATCC on 19 May 2006 comprising Pro115.B7.1 and Pro115.B34.1, specifically including the in vivo tumor targeting, internalization and any cell proliferation inhibition or cytotoxic characteristics. Specifically provided are anti-Pro115 antibodies that bind to an epitope present in amino acids 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310,-320, 320-330, 330-340, 340-350, 350-360, 360-370, 370-380, 380-390, 390-400, 400-410, 410-420, 420-430, 430-440, 440-450, 450-460, 460-470, 470-480, 480-490, 490-492 or 1-15, 10-25, 20-35, 30-45, 40-55, 50-65, 60-75, 70-85, 80-95, 90-105, 100-115, 110-125, 120-135, 130-145, 140-155, 150-165, 160-175, 170-185, 180-195, 190-205, 200-215, 210-225, 220-235, 230-245, 240-255, 250-265, 260-275, 270-285, 280-295, 290-305, 300-315, 310-325, 320-335, 330-345, 340-355, 350-365, 360-375, 370-385, 380-395, 390-405, 400-415, 410-425, 420-435, 430-445, 440-455, 450-465, 460-475, 470-485, 480-492 or Peptides 1-39 described in detail below of human Pro115.

Methods of producing the above antibodies are described in detail below.

The present anti-Pro115 antibodies are useful for treating a Pro115-expressing cancer or alleviating one or more symptoms of the cancer in a mammal. Such a cancer includes prostate, colon, lung or pancreas cancer, cancer of the urinary tract, lung cancer, breast cancer, colon cancer, pancreatic cancer, and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding, e.g., prostate, colon, lung or pancreas cancer metastases. The antibody is able to bind to at least a portion of the cancer cells that express Pro115 in the mammal and preferably is one that does not induce or that minimizes HAMA response. Preferably, the antibody is effective to destroy or kill Pro115-expressing tumor cells or inhibit the growth of such tumor cells, in vitro or in vivo, upon binding to Pro115 on the cell. Such an antibody includes a naked anti-Pro115 antibody (not conjugated to any agent). Naked anti-Pro115 antibodies having tumor growth inhibition properties in vivo include the antibodies described in the Experimental Examples below. Naked antibodies that have cytotoxic or cell growth inhibition properties can be further conjugated with a cytotoxic agent to render them even more potent in tumor cell destruction. Cytotoxic properties can be conferred to an anti-Pro115 antibody by, e.g., conjugating the antibody with a cytotoxic agent, to form an immunoconjugate as described below. The cytotoxic agent or a growth inhibitory agent is preferably a small molecule. Toxins such as maytansin, maytansinoids, saporin, gelonin, ricin or calicheamicin and analogs or derivatives thereof, are preferable.

The invention provides a composition comprising an anti-Pro115 antibody of the invention, and a carrier. For the purposes of treating cancer, compositions can be administered to the patient in need of such treatment, wherein the composition can comprise one or more anti-Pro115 antibodies present as an immunoconjugate or as the naked antibody. Further, the compositions can comprise these antibodies in combination with other therapeutic agents such as cytotoxic or growth inhibitory agents, including chemotherapeutic agents. The invention also provides formulations comprising an anti-Pro115 antibody of the invention, and a carrier. The formulation may be a therapeutic formulation comprising a pharmaceutically acceptable carrier.

Another aspect of the invention is isolated nucleic acids encoding the internalizing anti-Pro115 antibodies. Nucleic acids encoding both the H and L chains and especially the hypervariable region residues, chains which encode the native sequence antibody as well as variants, modifications and humanized versions of the antibody, are encompassed.

The invention also provides methods useful for treating an Pro115-expressing cancer or alleviating one or more symptoms of the cancer in a mammal, comprising administering a therapeutically effective amount of an internalizing anti-Pro115 antibody to the mammal. The antibody therapeutic compositions can be administered short term (acute) or chronic, or intermittent as directed by physician. Also provided are methods of inhibiting the growth of, and killing an Pro115 expressing cell. Finally, the invention also provides kits and articles of manufacture comprising at least one antibody of this invention, preferably at least one internalizing anti-Pro115 antibody of this invention. Kits containing anti-Pro115 antibodies find use in detecting Pro115 expression, or in therapeutic or diagnostic assays, e.g., for Pro115 cell killing assays or for purification and/or immunoprecipitation of Pro115 from cells. For example, for isolation and purification of Pro115, the kit can contain an anti-Pro115 antibody coupled to a solid support, e.g., a tissue culture plate or beads (e.g., sepharose beads). Kits can be provided which contain antibodies for detection and quantitation of Pro115 in vitro, e.g. in an ELISA or a Western blot. Such antibody useful for detection may be provided with a label such as a fluorescent or radiolabel.

Production of Anti-Pro115 Antibodies

The following describes exemplary techniques for the production of the antibodies useful in the present invention. Some of these techniques are described further in Example 1. The Pro115 antigen to be used for production of antibodies may be, e.g., the full length polypeptide or a portion thereof, including a soluble form of Pro115 lacking the membrane spanning sequence, or synthetic peptides to selected portions of the protein.

Alternatively, cells expressing Pro115 at their cell surface (e.g. CHO or NIH-3T3 cells transformed to overexpress Pro115; ovarian, pancreatic, lung, breast or other Pro115-expressing tumor cell line), or membranes prepared from such cells can be used to generate antibodies. The nucleotide and amino acid sequences of human and murine Pro115 are available as provided above. Pro115 can be produced recombinantly in and isolated from, prokaryotic cells, e.g., bacterial cells, or eukaryotic cells using standard recombinant DNA methodology. Pro115 can be expressed as a tagged (e.g., epitope tag) or other fusion protein to facilitate its isolation as well as its identification in various assays.

Antibodies or binding proteins that bind to various tags and fusion sequences are available as elaborated below. Other forms of Pro115 useful for generating antibodies will be apparent to those skilled in the art.

Tags

Various tag polypeptides and their respective antibodies are well known in the art. Examples include poly-histidine (poly-his) or poly-histidine-glycine(poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., Science, 255:192-194 (1992)1; an α-tubulin epitope peptide (Skinner et al., J. Biol. Chenz., 266:15163-15166 (1991)); and the T7 gene protein peptide tag (Lutz-Freyermuth et al., Proc. Natl. Acad. Sci. USA, 87:6393-6397 (1990)).

Polyclonal Antibodies

Polyclonal antibodies are preferably raised in animals, preferably non-human animals, by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Conjugates also can be made in recombinant cell culture as protein fusions.

Animals are immunized against the antigen, immunogenic conjugates, or derivatives by combining, e.g., 5-100 pg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a "fusion partner", e.g., a myeloma cell line using a suitable fusing agent, such as polyethylene glycol, to form a hybridoma cell (Goding, Monoclonal Antibodies. Principles and Practice, pp 103 (Academic Press, 1986)).

The hybridoma cells thus prepared are seeded and grown in a suitable culture medium which medium preferably contains one or more substances that inhibit the growth or survival of the unfused, fusion partner, e.g., the parental myeloma cells. For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp 103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxyapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed or transfected into prokaryotic or eukaryotic host cells such as, e.g., E coli cells, simian COS cells, Chinese Hamster Ovary (CHO) cells, or myeloma cells, that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Phickthun, Immunol. Revs., 130:151-188 (1992).

Further, the monoclonal antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266

(1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a non-immunoglobulin polypeptide (heterologous polypeptide). The nonimmunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is nonhuman. These non-human amino acid residues are often referred to as "import" residues, which are typically taken from an "import" variable domain. Humanization can be essentially performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen (s), is achieved. In general, the hypervariable region residues are directly and most substantially involved in influencing antigen binding.

Various forms of a humanized anti-Pro115 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; and Alternatively, phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab)2 fragments (Carter et al., Bio/Technology 10: 163-167 (1992)). According to another approach, F(ab)2 fragments can be isolated directly from recombinant host cell culture. Fab and F(ab)2 fragment with increased in vivo half-life comprising a salvage receptor binding epitope residues are described in U.S. Pat. No. 5,869,046. Other techniques for the production of antibody fragments will be apparent to the skilled practitioner. The antibody of choice may also be a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the Pro115 protein. Other such antibodies may combine an Pro115 binding site with a binding site for another protein. Alternatively, an anti-Pro115.Arm may be combined with an arm which binds to a triggering molecule on a leukocyte such as a Tcell receptor molecule (e.g. C133), or Fc receptors for IgG (FcγR), such as FcγRI (CD64), FcγRII (CD32) and FcγRIII (CD16), so as to focus and localize cellular defense mechanisms to the Pro115-expressing cell. Bispecific antibodies may also be used to localize cytotoxic agents to cells which express Pro115. These antibodies possess an Pro115-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Preferably, the bispecific antibodies in this approach are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1(X1n-VD2-(X2)n-Fc, wherein VDI is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the anti-Pro115 antibodies described herein are contemplated. For example, it may be desirable to improve the binding affinity and/or other biological properties of the antibody. Amino acid sequence variants of the anti-Pro115 antibody are prepared by introducing appropriate nucleotide changes into the anti-Pro115 antibody nucleic acid, or by peptide synthesis.

Such modifications include, for example, deletions from, and/or insertions into, and/or substitutions of, residues within the amino acid sequences of the anti-Pro115 antibody. Any combination of deletion, insertion, and substitution is made to arrive at the final construct, provided that the final construct possesses the desired characteristics. The amino acid changes also may alter post-translational processes of the anti-Pro115 antibody, such as changing the number or position of glycosylation sites.

A useful method for identification of certain residues or regions of the anti-Pro115 antibody that are preferred locations for mutagenesis is called "alanine scanning mutagenesis" as described by Cunningham and Wells in Science, 244:1081-1085 (1989). Here, a residue or group of target residues within the anti-Pro115 antibody are identified (e.g., charged residues such as arg, asp, his, lys, and glu) and replaced by a neutral or negatively charged amino acid (most preferably alanine or polyalanine) to affect the interaction of the amino acids with Pro115 antigen.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed anti-Pro115 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-Pro115 antibody with an N-terminal methionyl residue or the antibody fused to a cytotoxic polypeptide. Other insertional variants of the anti-Pro115 antibody molecule include the fusion to the N- or C-terminus of the anti-Pro115 antibody to an enzyme (e.g. for ADEPT) or a fusion to a polypeptide which increases the serum half-life of the antibody.

Another type of variant is an amino acid substitution variant. These variants have at least one amino acid residue in the anti-Pro115 antibody molecule replaced by a different residue. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in the table below, or as further described below in reference to amino acid classes, may be introduced and the products screened for a desired characteristic.

| Amino Acid Substitutions | | |
|---|---|---|
| Original | Exemplary Substitutions | Preferred Substitutions |
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; | leu |
| Leu (L) | norleucine; ile; val; met; ala; | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the anti-Pro115 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human Pro115. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-Pro115 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared nucleic acid molecule encoding a variant or a non-variant version of the anti-Pro115 antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of the antibody.

Screening for Antibodies with the Desired Properties

Techniques for generating antibodies have been described above. One may further select antibodies with certain biological characteristics, as desired.

The growth inhibitory effects of an anti-Pro115 antibody of the invention may be assessed by methods known in the art, e.g., using cells which express Pro115 either endogenously or following transfection with the Pro115 gene. For example, the tumor cell lines and Pro115-transfected cells provided in Example 1 below may be treated with an anti-Pro115 monoclonal antibody of the invention at various concentrations for a few days (e.g., 2-7) days and stained with crystal violet or MIT or analyzed by some other colorimetric assay. Another method of measuring proliferation would be by comparing $^3$H-thymidine uptake by the cells treated in the presence or absence an anti-Pro115 antibody of the invention. After antibody treatment, the cells are harvested and the amount of radioactivity incorporated into the DNA quantitated in a scintillation counter. Appropriated positive controls include treatment of a selected cell line with a growth inhibitory antibody known to inhibit growth of that cell line. Growth inhibition of tumor cells in vivo can be determined in various ways such as is described in the Experimental Examples section below. Preferably, the tumor cell is one that over-expresses Pro115. Preferably, the anti-Pro115 antibody will inhibit cell proliferation of an Pro115-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-Pro115 antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), trypan blue or 7AAD uptake may be assessed relative to a control. A PI uptake assay can be performed in the absence of complement and immune effector cells. Pro115-expressing tumor cells are incubated with medium alone or medium containing of the appropriate monoclonal antibody at e.g., about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on Pro115 bound by an antibody of interest, e.g., the Pro115 antibodies of this invention, a routine cross-blocking assay such as that describe in *Antibodies, A Laboratory Manual*, Cold Spring Harbor Laboratory, Ed Harlow and David Lane (1988), can be performed. This assay can be used to determine if a test antibody binds the same site or epitope as an anti-Pro115 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of Pro115 can be used in competition assays with the test antibodies or with a test antibody and an antibody with a characterized or known epitope.

For example, a method to screen for antibodies that bind to an epitope which is bound by an antibody this invention may comprise combining an Pro115-containing sample with a test antibody and an antibody of this invention to form a mixture, the level of Pro115 antibody bound to Pro115 in the mixture is then determined and compared to the level of Pro115 antibody bound in the mixture to a control mixture, wherein the level of Pro115 antibody binding to Pro115 in the mixture as compared to the control is indicative of the test antibody's binding to an epitope that is bound by the anti-Pro115 antibody of this invention. The level of Pro115 antibody bound to Pro115 is determined by ELISA. The control may be a positive or negative control or both. For example, the control may be a mixture of Pro115, Pro115 antibody of this invention and an antibody known to bind the epitope bound by the Pro115 antibody of this invention. The anti-Pro115 antibody labeled with a label such as those disclosed herein. The Pro115 may be bound to a solid support, e.g., a tissue culture plate or to beads, e.g., sepharose beads.

Immunoconjugates

The invention also pertains to therapy with immunoconjugates comprising an antibody conjugated to an anti-cancer agent such as a cytotoxic agent or a growth inhibitory agent.

Chemotherapeutic agents useful in the generation of such immunoconjugates have been described above. Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

Preferably, an anti-Pro115 antibody (full length or fragments) of the invention is conjugated to one or more maytansinoid molecules.

Maytansinoids are mitototic inhibitors which act by inhibiting tubulin polymerization. Maytansine was first isolated from the cast African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DMI linked to the monoclonal antibody C242 directed against human colorectal cancer. The conjugate was found to be highly cytotoxic towards cultured colon cancer cells, and showed antitumor activity in an in vivo tumor growth assay. Chari et al. Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×10 5 HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-Pro115 Antibody-Maytansinoid Conjugates (Immunoconjugates)

Anti-Pro115 antibody-maytansinoid conjugates are prepared by chemically linking an anti-Pro115 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al. Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred. Conjugates of the antibody and maytansinoid may be made using a variety of bifunctional protein coupling agents such as N-succinimidyl(2-pyridyidithio)propionate (SPDP), succinimidyl-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as his (p-azidobenzoyl)hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). Particularly preferred coupling agents include N-succinimidyl (2-pyridyldithio)propionate (SPDP) (Carlsson et al., Biochem. J. 173:723-737 [1978]) and N-succinimidyl(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. Preferably, the linkage is formed at the C-3 position of maytansinol or a maytansinol analogue.

Calicheamicin

Another immunoconjugate of interest comprises an anti-Pro115 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al. Cancer Research 53: 3336 (1993), Lode et al. Cancer Research 5 8: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-Pro115 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used include diphtheria A chain, 1 5 nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *saponaria officinalis* inhibitor, gelonin, mitogellin, restrictocin, phenomycin, enomycin and the tricothecenes. See, for example, WO 93/21232 published Oct. 28, 1993. The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-Pro115 antibodies. Examples include $At^{211}$, $I^{131}$, $I^{125}$, $In^{111}$, $Y^{90}$, $Re^{186}$, $Re^{188}$, $Sm^{153}$, $Bi^{212}$, $P^{32}$, and radioactive isotopes of Lu. When the conjugate is used for diagnosis, it may comprise a radioactive atom for scintigraphic studies, for example $Tc^{99M}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99M}$, $I^{123}$, $In^{111}$, $Re^{186}$, $Re^{188}$, can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl(2-pyridyldithio)propionate (SPDP), succinimidyl(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon labeled 1-isothiocyanatobenzyl methyldiethylene triaminepentaacetic acid (MX-DTPA) is an exemplary chelating agent for conjugation of radionucleotide to the antibody. See WO 94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. Cancer Research 52: 127-131 (1992); U.S. Pat. No. 5,208,020) may be used.

Alternatively, a fusion protein comprising the anti-Pro115 antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In addition, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population. The enzymes of this invention can be covalently bound to the anti-Pro115 antibodies by techniques well known in the art such as the use of the heterobifunctional crosslinking reagents discussed above.

Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-Pro115 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19)1484 (1989).

Vectors, Host Cells, and Recombinant Methods

The invention also provides isolated nucleic acid molecule encoding the humanized anti-Pro115 antibody, vectors and host cells comprising the nucleic acid, and recombinant techniques for the production of the antibody. For recombinant production of the antibody, the nucleic acid molecule encoding it is isolated and inserted into a replicable vector for further cloning (amplification of the DNA) or inserted into a vector in operable linkage with a promoter for expression. DNA encoding the monoclonal antibody is readily isolated and sequenced using conventional procedures (e.g., by using oligonucleotide probes that are capable of binding specifically to nucleic acid molecules encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

The anti-Pro115 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-Pro115 antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, oc factor leader (including *Saccharomyces* and *Kluyveromyces* cc-factor leaders), or acid phosphatase leader, the C albicans glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the anti-Pro115 antibody.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-Pro115 antibody nucleic acid, such as DHFR, thymidine kinase, metallothionein-I and -11, preferably primate metallothionein genes, adenosine deaminase, ornithine decarboxylase, etc. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding anti-Pro115 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4 Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 pm circular plasmid pKDI can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Promoter Component

Expression and cloning vectors usually contain a promoter that is recognized by the host organism and is operably linked to the anti-Pro115 antibody nucleic acid. Promoters suitable for use with prokaryotic hosts include the phoA promoter, P-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-Pro115 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoter sequences for use with yeast hosts include the promoters for 3-phosphoglycerate kinase or other glycolytic enzymes, such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-Pro115 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human P-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding the anti-Pro115 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-Pro115 antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding anti-Pro115 antibody. One useful transcription termination component is the bovine growth hormone polyadenylation region. See WO 94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W31 10 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-Pro115 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated anti-Pro115 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts.

Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells (Mather et al., Annals N.Y Acad. Sci. 383:44-68 (1982)); MRC 5 cells; FS4 cells; and a human hepatoma line (Hep G2).

Host cells are transformed with the above-described expression or cloning vectors for anti-Pro115 antibody production and cultured in conventional nutrient media modified as appropriate for inducing promoters, selecting transformants, or amplifying the genes encoding the desired sequences.

Culturing Host Cells

The host cells used to produce the anti-Pro115 antibody of this invention may be cultured in a variety of media. Commercially available media such as Ham's FIO (Sigma), Minimal Essential Medium (MEM)(Sigma), RPMI-1640 (Sigma), and Dulbecco's Modified Eagle's Medium (DMEM)(Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-Pro115 Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxyapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SIDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Pharmaceutical formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol, and mcresol); low molecular weight (less than about 10 residues) polypeptides; proteins, such as serum albumin, gelatin, or immunoglobulins; hydrophilic polymers such as polyvinylpyrollidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-Pro115 antibody which internalizes, it may be desirable to include in the one formulation, an additional antibody, e.g. a second anti-Pro115 antibody which binds a different epitope on Pro115, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−) hydroxybutyric acid.

The formulations to be used for in vivo administration must be sterile. This is readily accomplished by filtration through sterile filtration membranes.

Methods and Treatment Using Anti-Pro115 Antibodies

According to the present invention, the anti-Pro115 antibody that internalizes upon binding Pro115 on a cell surface is used to treat a subject in need thereof having a cancer characterized by Pro115-expressing cancer cells, in particular, prostate, colon, lung or pancreas cancer, and associated metastases.

The cancer will generally comprise Pro115-expressing cells, such that the anti-Pro115 antibody is able to bind thereto. While the cancer may be characterized by overexpression of the Pro115 molecule, the present application further provides a method for treating cancer which is not considered to be an Pro115-overexpressing cancer.

This invention also relates to methods for detecting cells or tissues which overexpress Pro115 and to diagnostic kits useful in detecting cells or tissues expressing Pro115 or in detecting Pro115 in bodily fluids from a patient. Bodily fluids include blood, serum, plasma, urine, ascites, peritoneal wash, saliva, sputum, seminal fluids, mucous membrane secretions, and other bodily excretions such as stool. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of normal cells of the same type as the test sample or a cell sample known to be free of Pro115 overexpressing cells. A level of Pro115 binding higher than that of such a control sample would be indicative of the test sample containing cells that overexpress Pro115. Alternatively the control may be a sample of cells known to contain cells that overexpress Pro115. In such a case, a level of Pro115 antibody binding in the test sample that is similar to, or in excess of, that of the control sample would be indicative of the test sample containing cells that overexpress Pro115.

Pro115 overexpression may be detected with a various diagnostic assays. For example, over expression of Pro115 may be assayed by immunohistochemistry (IHC). Parrafin embedded tissue sections from a tumor biopsy may be subjected to the IHC assay and accorded an Pro115 protein staining intensity criteria as follows.

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for Pro115 expression may be characterized as not overexpressing Pro115, whereas those tumors with 2+ or 3+ scores may be characterized as overexpressing Pro115.

Alternatively, or additionally, FISH assays such as the INFORM™ (sold by Ventana, Arizona) or PATHVISION™ (VySiS, Illinois) may be carried out on formalin-fixed, paraffin-embedded tumor tissue to determine the extent (if any) of Pro115 overexpression in the tumor. Pro115 overexpression or amplification may be evaluated using an in vivo diagnostic assay, e.g. by administering a molecule (such as an antibody of this invention) which binds Pro115 and which is labeled with a detectable label (e.g. a radioactive isotope or a fluorescent label) and externally scanning the patient for localization of the label.

A sample suspected of containing cells expressing or overexpressing Pro115 is combined with the antibodies of this invention under conditions suitable for the specific binding of the antibodies to Pro115. Binding and/or internalizing the Pro115 antibodies of this invention is indicative of the cells expressing Pro115. The level of binding may be determined and compared to a suitable control, wherein an elevated level of bound Pro115 as compared to the control is indicative of Pro115 overexpression. The sample suspected of containing cells overexpressing Pro115 may be a cancer cell sample, particularly a sample of prostate, colon, lung or pancreas cancer. A serum sample from a subject may also be assayed for levels of Pro115 by combining a serum sample from a subject with an Pro115 antibody of this invention, determining the level of Pro115 bound to the antibody and comparing the level to a control, wherein an elevated level of Pro115 in the serum of the patient as compared to a control is indicative of overexpression of Pro115 by cells in the patient. The subject may have a cancer such as prostate, colon, lung or pancreas cancer.

Currently, depending on the stage of the cancer, prostate, colon, lung or pancreas cancer treatment involves one or a combination of the following therapies: surgery to remove the cancerous tissue, radiation therapy, androgen deprivation (e.g., hormonal therapy), and chemotherapy. Anti-Pro115 antibody therapy may be especially desirable in elderly patients who do not tolerate the toxicity and side effects of chemotherapy well, in metastatic disease where radiation therapy has limited usefulness, and for the management of prostatic carcinoma that is resistant to androgen deprivation treatment. The tumor targeting and internalizing anti-Pro115 antibodies of the invention are useful to alleviate Pro115-expressing cancers, e.g., prostate, colon, lung or pancreas cancers upon initial diagnosis of the disease or during relapse. For therapeutic applications, the anti-Pro115 antibody can be used alone, or in combination therapy with, e.g., hormones, antiangiogens, or radiolabelled compounds, or with surgery, cryotherapy, and/or radiotherapy, notably for prostate, colon, lung or pancreas cancers, also particularly where shed cells cannot be reached. Anti-Pro115 antibody treatment can be administered in conjunction with other forms of conventional therapy, either consecutively with, pre- or post-conventional therapy, Chemotherapeutic drugs such as Taxotere® (docetaxel), Taxol® (paclitaxel), estramustine and mitoxantrone are used in treating metastatic and hormone refractory prostate, colon, lung or pancreas cancer, in particular, in good risk patients. In the present method of the invention for treating or alleviating cancer, in particular, androgen independent and/or metastatic prostate, colon, lung or pancreas cancer, the cancer patient can be administered anti-Pro115 antibody in conjunction with treatment with the one or more of the preceding chemotherapeutic agents. In particular, combination therapy with palictaxel and modified derivatives (see, e.g., EP0600517) is contemplated. The anti-Pro115 antibody will be administered with a therapeutically effective dose of the chemotherapeutic agent. The anti-Pro115 antibody may also be administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Particularly, an immunoconjugate comprising the anti-Pro115 antibody conjugated with a cytotoxic agent may be administered to the patient. Preferably, the immunoconjugate bound to the Pro115 protein is internalized by the cell, resulting in increased therapeutic efficacy of the immunoconjugate in killing the cancer cell to which it binds. Preferably, the cytotoxic agent targets or interferes with the nucleic acid in the cancer cell. Examples of such cytotoxic agents are described above and include maytansin, maytansinoids, saporin, gelonin, ricin, calicheamicin, ribonucleases and DNA endonucleases.

The anti-Pro115 antibodies or immunoconjugates are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies or immunoconjugates may be injected directly into the tumor mass. Intravenous or subcutaneous administration of the antibody is preferred. Other therapeutic regimens may be combined with the administration of the anti-Pro115 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Pro115 antibody or antibodies, with administration of an antibody directed against another tumor antigen associated with the particular cancer. As such, this invention is also directed to an antibody "cocktail" comprising one or more antibodies of this invention and at least one other antibody which binds another tumor antigen associated with the Pro115-expressing tumor cells. The cocktail may also comprise antibodies that are directed to other epitopes of Pro115. Preferably the other antibodies do not interfere with the binding and or internalization of the antibodies of this invention.

The antibody therapeutic treatment method of the present invention may involve the combined administration of an anti-Pro115 antibody (or antibodies) and one or more chemotherapeutic agents or growth inhibitory agents, including co-administration of cocktails of different chemotherapeutic agents. Chemotherapeutic agents include, e.g., estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-Pro115 antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-Pro115 antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Pro115 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et at., Science 256:808-813 (1992). See also WO 93/25673 and the references cited therein.

Articles of Manufacture and Kits

The invention also relates to an article of manufacture containing materials useful for the detection for Pro115 overexpressing cells and/or the treatment of Pro115 expressing cancer, in particular prostate, colon, lung or pancreas cancer. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting Pro115 expressing cells and/or treating a cancer condition and may have a sterile access port (for example the container may be an intravenous solution bag or a vial having a stopper pierceable by a hypodermic injection needle). At least one active agent in the composition is an anti-Pro115 antibody of the invention. The label or package insert indicates that the composition is used for detecting Pro115 expressing cells and/or for treating prostate, colon, lung or pancreas cancer, in a patient in need thereof. The label or package insert may further comprise instructions for administering the antibody composition to a cancer patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g., for Pro115 cell killing assays, for purification or immunoprecipitation of Pro115 from cells or for detecting the presence of Pro115 in a serum sample or detecting the presence of Pro115-expressing cells in a cell sample. For isolation and purification of Pro115, the kit can contain an anti-Pro115 antibody coupled to a solid support, e.g., a tissue culture plate or beads (e.g., sepharose beads). Kits can be provided which contain the antibodies for detection and quantitation of Pro115 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may provide a description of the composition as well as instructions for the intended in vitro or diagnostic use.

EXAMPLES

Example 1

Production and Isolation of Monoclonal Antibody Producing Hybridomas

The following MAb/hybridomas of the present invention are described below: Pro115.A1, Pro115.A2, Pro115.A3, Pro115.A4, Pro115.A5, Pro115.A6, Pro115.A7, Pro115.A8, Pro115.A9, Pro115.A10, Pro115.A11, Pro115.A12, Pro115.A13, Pro115.A14, Pro115.A15, Pro115.A16, Pro115.A17, Pro115.A18, Pro115.A19, Pro115.A20, Pro115.A21, Pro115.A22, Pro115.A23, Pro115.A24, Pro115.A25, Pro115.A101.1, Pro115.A102.1, Pro115.A103.1, Pro115.A104.1, Pro115.A106.1, Pro115.A107.1, Pro115.A108.1, Pro115.B1, Pro115.B2, Pro115.B3, Pro115.B4, Pro115.B5, Pro115.B6, Pro115.B7, Pro115.B8, Pro115.B9, Pro115.B10, Pro115.B11, Pro115.B12, Pro115.B13, Pro115.B14, Pro115.B15, Pro115.B16, Pro115.B17, Pro115.B18, Pro115.B19, Pro115.B20, Pro115.B21, Pro115.B22, Pro115.B23, Pro115.B24, Pro115.B25, Pro115.B26, Pro115.B27, Pro115.B28, Pro115.B29, Pro115.B30, Pro115.B31, Pro115.B32, Pro115.B33, Pro115.B34, Pro115.B35, Pro115.B36, Pro115.B37, Pro115.B38, Pro115.B39, Pro115.B40, Pro115.B41, Pro115.B42, Pro115.B43, Pro115.B44, Pro115.B45, Pro115.B46, Pro115.B47, Pro115.B48, Pro115.B49, Pro115.B50, Pro115.B51, Pro115.B52, Pro115.B53, Pro115.B54, Pro115.B55, Pro115.B56, Pro115.B57, Pro115.B58, Pro115.B59, Pro115.B60, Pro115.B61, Pro115.B62, Pro115.B63, Pro115.B64, Pro115.B65, Pro115.B66, Pro115.B67, Pro115.B68, Pro115.B69, Pro115.D1, Pro115.D2, Pro115.D3, Pro115.D4, Pro115.D5, Pro115.D6, Pro115.D7, Pro115.D8, Pro115.D9, Pro115.D10, Pro115.D11, Pro115.D12, Pro115.D13, Pro115.F2 and Pro115.F3.

If the MAb has been cloned, it will get the nomenclature "X.1," e.g., the first clone of Pro115.B7 will be referred to as B7.1, the second clone of B7 will be referred to as B7.2, etc. For the purposes of this invention, a reference to Pro115.B7 or B7 will include all clones, e.g., B7.1, B7.2, etc.

Immunogens and Antigens (Recombinant Proteins, HA & His Tags & Transfected Cells)

For the Constructs described below, nucleic acid molecules encoding regions of Pro115 were inserted into various expression vectors to produce recombinant proteins.

For purposes of illustration, the amino acid sequence encoded by each construct is also included. However, the constructs may include naturally occurring variants (e.g. allelic variants, SNPs) within the Pro115 region as isolated by the primers. These variant sequences, and antibodies which bind to them are considered part of the invention as described herein.

Pro115 Construct 1 Sequence and Protein Production

A nucleic acid molecule encoding the full length Pro115 protein, amino acids Met1 to Gly492, was inserted into a pCMV5His3 vector at the PmeI/NheI sites. The vector comprises a sequence at the 3' end of the cloning site encoding two transitional amino acids, Ala and Ser, and a 10 His tag. The resulting vector with the inserted Pro115 nucleic acid fragment encodes a recombinant Pro115 fusion protein with the 10 His-tag fused to the C-terminus of the Pro115 protein. This recombinant plasmid encoding the full length Pro115 His-tagged protein is herein referred to as "Pro115 Construct 1". A representative amino acid sequence encoded by Pro115 Construct 1 is presented in SEQ ID NO:1.

```
                                                              (SEQ ID NO: 1)
Pro115 Construct 1 Amino Acid Sequence
  1          11         21         31         41         51
  |          |          |          |          |          |
  1 MALNSGSPPA IGPYYENHGY QPENPYPAQP TVVPTVYEVH PAQYYPSPVP QYAPRVLTQA

61 SNPVVCTQPK SPSGTVCTSK TKKALCITLT LGTFLVGAAL AAGLLWKFMG SKCSNSGIEC

121 DSSGTCINPS NWCDCVSHCP GGEDENRCVR LYGPNFILQV YSSQRKSWHP VCQDDWNENY

181 GRAACRDMGY KNNFYSSQGI VDDSGSTSFM KLNTSAGNVD IYKKLYHSDA CSSKAVVSLR

241 CIACGVNLNS SRQSRIVGGE SALPGAWPWQ VSLHVQNVHV CGGSIITPEW IVTAAHCVEK

301 PLNNPWHWTA FAGILRQSFM FYGAGYQVEK VISHPNYDSK TKNNDIALMK LQKPLTFNDL

361 VKPVCLPNPG MMLQPEQLCW ISGWGATEEK GKTSEVLNAA KVLLIETQRC NSRYVYDNLI

421 TPAMICAGFL QGNVDSCQGD SGGPLVTSKN NIWWLIGDTS WGSGCAKAYR PGVYGNVMVF

481 TDWIYRQMRA DGASHHHHHH HHHH
```

Pro115 protein expressed by Construct 1 was column purified using standard techniques from cell culture of 293F cells transfected with Construct 1. Samples from collected fractions were subjected to SDS-PAGE and Western blot analysis for assessing the purity of the protein. Purified fractions were pooled and dialyzed against PBS, pH 7.4. Pro115 expressed by Construct 1 was enzymatic active.

Pro115 Construct 2 Sequence and Protein Production

A nucleic acid molecule encoding a mutant extra-cellular region of Pro115 protein, amino acids Gly110 to Gly492, was inserted into a modified pTT3 vector at the PmeI/NheI sites. The codon encoding amino acid S441 was modified to encode A441, producing Pro115 mutant without protease activity.

The vector comprises a sequence at the 5' end of the cloning site encoding an amino acid secretion signal sequence from human stanniocalcin 1 (STC) and a sequence at the 3' end of the cloning site encoding two transitional amino acids, Ala and Ser, and a 10 His tag. The resulting vector with the inserted Pro115 nucleic acid fragment encodes a recombinant Pro115 fusion protein with a N-terminus STC secretion signal and a 10 His-tag fused to the C-terminus of the Pro115 protein. This recombinant plasmid encoding the mutant extra-cellular region His-tagged protein is herein referred to as "Pro115 Construct 2". A representative amino acid sequence encoded by Pro115 Construct 2 is presented in SEQ ID NO:2.

Pro115 Construct 2 Amino Acid Sequence
(SEQ ID NO: 2)
MLQNSAVLLVLVISASADIGSKCSNSGIECDSSGTCINPSNWCDGVSHCP

GGEDENRCVRLYGPNFILQVYSSQRKSWHPVCQDDWNENYGRAACRDMGY

KNNFYSSQGIVDDSGSTSFMKLNTSAGNVDIYKKLYHSDACSSKAVVSLR

CIACGVNLNSSRQSRIVGGESALPGAWPWQVSLHVQNVHVCGGSIITPEW

IVTAAHCVEKPLNNPWHWTAFAGILRQSFMFYGAGYQVEKVISHPNYDSK

TKNNDIALMKLQKPLTFNDLVKPVCLPNPGMMLQPEQLCWISGWGATEEK

GKTSEVLNAAKVLLIETQRCNSRYVYDNLITPAMICAGFLQGNVDSCQGD

AGGPLVTSKNNIWWLIGDTSWGSGCAKAYRPGVYGNVMVFTDWIYRQMRA

DGASHHHHHHHHHH

Pro115 protein expressed by Construct 2 was column purified using standard techniques from mammalian cell culture transfected with Construct 2. Samples from collected fractions were subjected to SDS-PAGE and Western blot analysis for assessing the purity of the protein. Purified fractions were pooled and dialyzed against PBS, pH 7.4. Pro115 expressed by Construct 2 was not enzymatic active.

Pro115 Construct 3 Sequence and Protein Production

A nucleic acid molecule encoding the protease domain of Pro115 protein, amino acids Ile236 to Gly492, was inserted into a modified pTT3 vector at the PmeI/NheI sites. The vector comprises a sequence at the 5' end of the cloning site encoding an amino acid secretion signal sequence from human stanniocalcin 1 (STC) and a sequence at the 3' end of the cloning site encoding two transitional amino acids, Ala and Ser, and a 10 His tag. The resulting vector with the inserted Pro115 nucleic acid fragment encodes a recombinant Pro115 fusion protein with a N-terminus STC secretion signal and a 10 His-tag fused to the C-terminus of the Pro115 protein. This recombinant plasmid encoding the His-tagged Pro115 protease domain protein is herein referred to as "Pro115 Construct 3". A representative amino acid sequence encoded by Pro115 Construct 3 is presented in SEQ ID NO:3.

Pro115 Construct 3 Amino Acid Sequence
(SEQ ID NO: 3)
MLQNSAVLLVLVISASADIIVGGESALPGAWPWQVSLHVQNVHVCGGSII

TPEWIVTAAHCVEKPLNNPWHWTAFAGILRQSFMFYGAGYQVEKVISHPN

YDSKTKNNDIALMKLQKPLTFNDLVKPVCLPNPGMMLQPEQLCWISGWGA

TEEKGKTSEVLNAAKVLLIETQRCNSRYVYDNLITPAMICAGFLQGNVDS

CQGDSGGPLVTSKNNIWWLIGDTSWGSGCAKAYRPGVYGNVMVFTDWIYR

QMRADGASHHHHHHHHHH

Pro115 protein expressed by Construct 3 was column purified using standard techniques from mammalian cell culture transfected with Construct 3. Samples from collected fractions were subjected to SDS-PAGE and Western blot analysis for assessing the purity of the protein. Purified fractions were pooled and dialyzed against PBS, pH 7.4. Pro115 expressed by Construct 3 was enzymatic active.

Pro115 Membrane Prep from RK3E-Pro115 Cells

For cell membrane preps, RK3E cells were transfected to express full length Pro115 using standard techniques. Approximately 3 mL packed RK3E-Pro115 cells were homogenized with a Bellco Dounce pestle in sucrose buffer and subjected to discontinuous gradient ultracentrifugation (25000 rpm for 2 hours) in a Beckman SW28 rotor. Membrane pellicules were collected, washed with phosphate-buffered saline, and centrifuged for 5 minutes at 2000 rpm. The pellet containing the membrane fraction was left on ice overnight and was resuspended in 7.5 mL phosphate-buffered saline and frozen prior to content confirmation by western blot analysis.

Pro115v1 Construct 1 Sequence and Protein Production

A splice variant of Pro115 named Pro115v1 has been described in PCT/US2005/035607. A nucleic acid molecule encoding the extra-cellular region of Pro115v1, amino acids Gly110 to Leu257, was inserted into a modified pCMV5His3 vector at the PmeI/NheI sites.

The vector comprises a sequence at the 5' end of the cloning site encoding an amino acid secretion signal sequence from human stanniocalcin 1 (STC) linked to a 10 His tag. The resulting vector with the inserted Pro115v1 nucleic acid fragment encodes a recombinant Pro115v1 fusion protein with a N-terminus STC secretion signal and a 10 His-tag. This recombinant plasmid encoding the His-tagged Pro115v1 extra-cellular domain protein is herein referred to as "Pro115v1 Construct 1". A representative amino acid sequence encoded by Pro115 Construct 3 is presented in SEQ ID NO:4.

Pro115v1 Construct 1 Amino Acid Sequence
(SEQ ID NO: 4)
MLQNSAVLLVLVISASADIHHHHHHHHHHGSKCSNSGIECDSSGTCINPS

NWCDGVSHCPGGEDENRCGESALTLGRDSSAHLGDSSRVQGPLGDWAWRA

SSTLTHDVIESLLQAEPWGSERLCFRPNLTQQVGDDRATEDCVIGTTRAL

NCHRKSVKMSKLFIKLEMQARNGGSCL

Pro115v1 protein expressed by Pro115v1 Construct 1 expressed using standard techniques from mammalian cell culture (293F cells) transfected with Pro115v1 Construct 1. GnHCl denaturing purification, followed by refolding, produced a native or near-native protein. Samples from collected fractions were subjected to SDS-PAGE and Western blot analysis for assessing the purity of the protein. Purified fractions were pooled and dialyzed against PBS, pH 7.4.

Pro104 Construct 1 Sequence and Protein Production

Pro104 has previously been described in WO 99/60162 and WO 00/16805. A nucleic acid molecule encoding a region of Pro104 protein, amino acids Arg19-Trp297 was inserted into a modified pTJR3 vector. The vector comprises a sequence at the 5' end of the cloning site encoding an amino acid secretion signal sequence from human stanniocalcin 1 (STC) and a sequence at the 3' end of the cloning site encoding two transitional amino acids, Ala and Ser, and a 10 His tag. The resulting vector with the inserted Pro104 nucleic acid fragment encodes a recombinant Pro104 fusion protein with a N-terminus STC secretion signal and a 10 His-tag fused to the C-terminus of the Pro104 protein. This recombinant plasmid encoding the protein is herein referred to as "Pro104 Construct 1". A representative amino acid sequence encoded by Pro104 Construct 1 is presented in SEQ ID NO:5.

Pro104 Construct 1 Amino Acid Sequence
(SEQ ID NO: 5)
MLQNSAVLLVLVISASATHEAEQSRKPESQEAAPLSGPCGRRVITSRIVG

GEDAELGRWPWQGSLRLWDSHVCGVSLLSHRWALTAAHCFETYSDLSDPS

GWMVQFGQLTSMPSFWSLQAYYTRYFVSNIYLSPRYLGNSPYDIALVKLS

APVTYTKHIQPICLQASTFEFENRTDCWVTGWGYIKEDEALPSPHTLQEV

-continued

QVAIINNSMCNHLFLKYSFRKDIFGDMVCAGNAQGGKDACFGDSCCPLAC

NKNGLWYQIGVVSWGVGCGRPNRPGVYTNISHHFEWIQKLMAQSGMSQPD

PSWASHHHHHHHHHH

Pro104 protein expressed by Pro104 Construct 1 was column purified using standard techniques from mammalian cell culture transfected with Construct 1. Samples from collected fractions were subjected to SDS-PAGE and Western blot analysis for assessing the purity of the protein. Purified fractions were pooled and dialyzed against PBS, pH 7.4.

Cln101 Construct 1 Sequence and Protein Production

Cln101 has previously been described in WO 05/021709. A nucleic acid molecule encoding a region of Cln101 protein, amino acids Asp23-Pro158 was inserted into a modified pCMV5His2 vector. The vector comprises a sequence at the 5' end of the cloning site encoding an amino acid secretion signal sequence from human stanniocalcin 1 (STC) and a sequence at the 3' end of the cloning site encoding two transitional amino acids, Ala and Ser, and a 10 His tag. The resulting vector with the inserted Cln101 nucleic acid fragment encodes a recombinant Cln101 fusion protein with a N-terminus STC secretion signal and a 10 His-tag fused to the C-terminus of the Cln101 protein. This recombinant plasmid encoding the protein is herein referred to as "Cln101 Construct 1". A representative amino acid sequence encoded by Cln101 Construct 1 is presented in SEQ ID NO:6.

Cln101 Construct 1 Amino Acid Sequence
(SEQ ID NO: 6)
MLQNSAVLLVLVISASATHEAEQDIIMRPSCAPCWFYHKSNCYGYFRKLR

NWSDAELECQSYGNGAHLASILSLKEASTIAEYISCYQRSQPIWIGLHDP

QKRQQWQWIDGAMYLYRSWSGKSMGGNKHCAEMSSNNNFLTWSSNECNKR

QHFLCKYRPASHHHHHHHHHH

Cln101 protein expressed by Cln101 Construct 1 was column purified using standard techniques from mammalian cell culture transfected with Construct 1. Samples from collected fractions were subjected to SDS-PAGE and Western blot analysis for assessing the purity of the protein. Purified fractions were pooled and dialyzed against PBS, pH 7.4.

Cln242 Construct 1 Sequence and Protein Production

Cln242 has previously been described in WO 01/92528 and is also known as Cln165. A nucleic acid molecule encoding a region of Cln242 protein, amino acids Met1-Asp198 was inserted into a modified pCMV5His2 vector. The vector comprises a sequence at the 3' end of the cloning site encoding two transitional amino acids, Ala and Ser, and a 10 His tag. The resulting vector with the inserted Cln242 nucleic acid fragment encodes a recombinant Cln242 fusion protein with a 10 His-tag fused to the C-terminus of the Cln242 protein. This recombinant plasmid encoding the protein is herein referred to as "Cln242 Construct 1". A representative amino acid sequence encoded by Cln242 Construct 1 is presented in SEQ ID NO:7.

Cln242 Construct 1 Amino Acid Sequence
(SEQ ID NO: 7)
MSGGHQLQLAALWPWLLMATLQAGFGRTGLVLAAAVESERSAEQKAIIRV

IPLKMDPTGKLNLTLEGVFAGVAEITPAEGKLMQSHPLYLCNASDDDNLE

PGFISIVKLESPRRAPRPCLSLASKARMAGERGASAVLFDITEDRAAAEQ

LQQPLGLTWPVVLIWGNDAEKLMEFVYKNQKAHVRIELKEPPAWPDYDDI

ASHHHHHHHHHH

Cln242 protein expressed by Cln242 Construct 1 was purified using standard techniques from mammalian cell culture transfected with Construct 1. Samples from collected fractions were subjected to SDS-PAGE and Western blot analysis for assessing the purity of the protein. Purified fractions were pooled and dialyzed against PBS, pH 7.4.

Ovr110 Construct 1 Sequence and Protein Production

A nucleic acid molecule encoding Ovr110 (also known as B7H4) protein was inserted into a vector for expression. The resulting vector with the inserted Ovr110 nucleic acid fragment encodes a recombinant Ovr110 fusion protein with a 10 His-tag fused to the C-terminus of the Ovr110 protein. This recombinant plasmid encoding the protein is herein referred to as "Ovr110 Construct 1". A representative amino acid sequence encoded by Ovr110 Construct 1 is presented in SEQ ID NO:8.

Ovr110 Construct 1 Amino Acid Sequence
(SEQ ID NO: 8)
MASLGQILFWSIISIIIILAGAIALIIGFGISGRHSITVTTVASAGNIGE

DGILSCTFEPDIKLSDIVIQWLKEGVLGLVHEFKEGKDELSEQDEMFRGR

TAVFADQVIVGNASLRLKNVQLTDAGTYKCYIITSKGKGNANLEYKTGAF

SMPEVNVDYNASSETLRCEAPRWFPQPTVVWASQVDQGANFSEVSNTSFE

LNSENVTMKVVSVLYNVTINNTYSCMIENDIAKATGDIKVTESEIKRRSH

LQLLNSKASLCVSSFFAISWALLPLSPYLMLKASHHHHHHHHHH

Ovr110 protein expressed by Ovr110 Construct 1 was purified using standard techniques from mammalian cell culture transfected with Construct 1. Samples from collected fractions were subjected to SDS-PAGE and Western blot analysis for assessing the purity of the protein. Purified fractions were pooled and dialyzed against PBS, pH 7.4.

Immunizations

Mice were immunized with various Pro115 and Pro115v1 constructs to generate anti-Pro115 MAbs capable of binding to Pro115 in bodily fluids and on a cell surface. MAbs are capable of binding to Pro115 expressing cells, killing Pro115 expressing cells, and have utility as in-vivo therapeutic agents, and in-vivo and in-vitro diagnostic agents.

For the A-series MAb fusion, mice were immunized with the protein encoded by Pro115 Construct 1 (described above). The protein was expressed in mammalian cells.

For the B-series MAb fusion, mice were immunized with the protein encoded by Pro115 Construct 2 (described above). The protein was expressed in mammalian cells.

For the D-series MAb fusion, mice were immunized with the protein encoded by Pro115 Construct 3 (described above). The protein was expressed in mammalian cells.

For the F-series MAb fusion, mice were immunized with membranes isolated from Pro115-transfected RK3E cells (described above).

For each series, groups of 8 BALB/c mice were immunized intradermally in both rear footpads. All injections were 25 uL per foot. For the A-, B-, and D-series, the first injection of 10 ug of antigen per mouse was in Dulbecco's phosphate buffered saline (DPBS) mixed in equal volume to volume ratio with Titermax gold adjuvant (Sigma). Subsequently, mice were immunized twice weekly for 5 weeks. For the $2^{nd}$ through $9^{th}$ injection, mice were immunized with 10 ug of antigen in 20 uL of DPBS plus 5 uL of Adju-phos adjuvant (Accurate Chemical & Scientific Corp., Westbury, N.Y.) per mouse. The final immunization consisted of 10 ug antigen diluted in DPBS alone. For the F-series, mice were injected with membranes prepared from RK3E cells stably transfected with Pro115. Mice were immunized twice weekly for five weeks with 10 ug RK3E-Pro115 membranes in 25 uL PBS per foot.

Hybridoma Fusion

Four days after the final immunization, mice were sacrificed and draining lymph node (popliteal and inguinal) tissue was collected by sterile dissection. Lymph node cells were dispersed using a Tenbroeck tissue grinder (Wheaton #347426, VWR, Brisbane, Calif.) followed by pressing through a sterile sieve (VWR) into DMEM and removing T-cells via anti-CD90 (Thy1.2) coated magnetic beads (Miltenyi Biotech, Bergisch-Gladbach, Germany).

These primary B-cell enriched lymph node cells were then immortalized by electro-cell fusion (BTX, San Diego, Calif.) with the continuous myeloma cell line P3x63Ag8.653 (Kearney, J. F. et al., J. Immunology 123: 1548-1550, 1979). The myeloma and B-cells were pooled at a 1:1 ratio for the fusion. These fusion cultures were distributed at 2 million cells per plate into wells of 96 well culture plates (Costar #3585, VWR). Successfully fused cells were selected by culturing in selection medium (DMEM/15% FBS) containing 2.85 µM Azaserine, 50 µM Hypoxanthine (HA) (Sigma) or 50 µM Hypoxanthine, 0.2 µM Aminopterin, 8 µM Thymidine (HAT) (Sigma) supplemented with recombinant human IL-6 (Sigma) at 0.5 ng/mL. Cultures were transitioned into medium (DMEM/10% FBS/IL-6) without selection for continued expansion and antibody production.

Alternatively, fused cells were cultured in bulk in selection medium for 6 days and then plated, 1 cell per well, into 96 well culture plates by cell sorting (Coulter Elite). Cells were cultured and transitioned into medium (DMEM/10% FBS/IL-6) without selection for continued expansion and antibody production. Hybridomas generated by this plating method are designated A101.1 to A122.1 in Table 1.

Supernatants from wells were screened by enzyme linked solid phase immunoassay (ELISA) and flow cytometry for antibodies binding to recombinant Pro115 protein and to Pro115 expressed on cells. Monoclonal cultures, consisting of the genetically uniform progeny from single cells, were established after the screening procedure, by sorting of single viable cells into wells of two 96 well plates, using flow cytometry (Coulter Elite; Beckman-Coulter, Miami, Fla.). The resulting murine B-cell hybridoma cultures were expanded using standard tissue culture techniques. Selected hybridomas were cryopreserved in fetal bovine serum (FBS) with 10% DMSO and stored in Liquid Nitrogen at −196° C. to assure maintenance of viable clone cultures.

ELISA Screening & Selection of Hybridomas Producing Pro115 Specific Antibodies

A Series Antibodies

Hybridoma cell lines were selected for production of Pro115 specific antibodies by direct ELISA. Wells were coated with proteins encoded by Pro115 Construct 1, Pro115v1 Construct 1, Pro104 Construct 1 (negative control) or Cln101 Construct 1 (negative control); all described above. To coat wells one ug/mL protein in PBS (100 uL/well) was incubated overnight in 96 well polystyrene EIA plates (Costar #9018, VWR) at 4° C. The plate wells were washed twice with Tris buffered saline with 0.05% Tween20, pH 7.4 (TBST). Nonspecific binding capacity was blocked by filling the wells (300 ul/well) with TBST/0.5% bovine serum albumin (TBST/BSA) and incubating for >30 minutes at room temperature (RT). The wells were emptied and filled with 50 uL/well TBST/BSA to prevent them from drying out during the sample collection process. Hybridoma culture medium sample was added to the wells (50 uL) and incubated for 1 hour at RT. The wells were washed 3 times with TBST. One hundred uL of alkaline phosphatase conjugated goat anti-mouse IgG (Fc) with minimal cross-reactivity to human Fc (PN115-055-071, Jackson Immunoresearch), diluted 1:5000 in 1BST/BSA, was added to each well and incubated for >1 hour at RT. The wells were washed 3 times with TBST. One hundred uL of alkaline phosphatase substrate para-nitrophenylphosphate (pNPP) (Sigma) at 1 mg/mL in 1 M Diethanolamine buffer pH 8.9 (Pierce) was added to each well and incubated for 20 min at RT. The enzymatic reaction was quantified by measuring the solution's absorbance at 405 nm wavelength.

TABLE 1

ELISA with supernatants of A-series hybridomas.

| Hybridoma | ELISA OD [405 nm] | | | |
| --- | --- | --- | --- | --- |
| | Pro115 | Pro115v1 | Pro104 | Cln101 |
| A1 | 1.3067 | 3.3473 | 0.1028 | 0.1189 |
| A2 | 0.8973 | 0.4626 | 0.0965 | 0.1020 |
| A3 | 1.0153 | 0.1163 | 0.1041 | 0.1032 |
| A4 | 1.7338 | 0.1473 | 0.1305 | 0.1378 |
| A5 | 2.0018 | 4.0000 | 0.1040 | 0.1150 |
| A6 | 1.0826 | 0.0964 | 0.0990 | 0.1052 |
| A7 | 1.3652 | 0.0997 | 0.1102 | 0.1168 |
| A8 | 1.7950 | 1.8729 | 0.1121 | 0.1077 |
| A9 | 1.3678 | 0.9320 | 0.1346 | 0.1012 |
| A10 | 0.9950 | 0.3955 | 0.1055 | 0.1210 |
| A11 | 0.7001 | 0.1144 | 0.1172 | 0.1232 |
| A12 | 0.9987 | 0.1529 | 0.0973 | 0.1152 |
| A13 | 0.9895 | 0.7933 | 0.1024 | 0.1075 |
| A14 | 1.2906 | 0.1014 | 0.1062 | 0.1030 |
| A15 | 1.1788 | 0.0962 | 0.2407 | 0.1038 |
| A16 | 1.4956 | 0.3009 | 0.1048 | 0.1135 |
| A17 | 1.4809 | 3.4570 | 0.1118 | 0.1252 |
| A18 | 1.1674 | 0.0940 | 0.0962 | 0.1177 |
| A19 | 1.2368 | 0.0984 | 0.0959 | 0.1038 |
| A20 | 0.7900 | 0.1078 | 0.0982 | 0.1144 |
| A21 | 0.6521 | 0.1075 | 0.1059 | 0.1111 |
| A22 | 1.0836 | 0.1039 | 0.1171 | 0.1090 |
| A23 | 0.7594 | 0.1016 | 0.1053 | 0.1162 |
| A25 | 2.0331 | 0.1059 | 0.1326 | 0.1051 |
| A24 | 2.2609 | 3.5445 | 0.1013 | 0.1040 |
| A101.1 | 1.0194 | 0.1302 | 0.1057 | 0.1139 |
| A102.1 | 1.2091 | 0.1129 | 0.0998 | 0.1221 |
| A103.1 | 1.0498 | 0.0989 | 0.1065 | 0.1164 |
| A104.1 | 1.2561 | 0.1042 | 0.1062 | 0.1191 |
| A106.1 | 1.1505 | 0.0990 | 0.1012 | 0.1009 |
| A107.1 | 1.5703 | 4.0000 | 0.1194 | 0.1042 |
| A108.1 | 1.0811 | 2.3565 | 0.1053 | 0.1076 |

Supernatants from 32 hybridomas produced an absorbance value of greater than 0.5 in wells coated with Pro115 Construct 1 and less than 0.16 in wells coated with Cln101 Construct 1, indicating preferential antibody binding to Pro115. Antibodies from 19 of the 32 hybridomas did not bind to Pro115v1 Construct1 and Pro104 Construct 1, indicating specific binding to Pro115. These hybridomas are designated A3, A4, A6, A7, A11, A12, A14, A18, A19, A20, A21, A22, A23, A25, A101, A102, A103, A104, and A106. Antibodies from 12 of the 32 hybridomas bound to Pro115 Construct 1 and Pro115v1 Construct 1, indicating binding to the common domain of Pro115 and Pro115v1 (amino acids Met1 to Cys148). These hybridomas are designated A1, A2, A5, A8, A9, A10, A13, A16, A17, A24, A107, and A108. One antibody, named A15, bound to Pro115 Construct 1, and has some cross-reactivity with Pro104 Construct 1. Selected hybridomas were expanded for further analysis.

B Series Antibodies

Hybridoma cell lines were selected for production of Pro115 specific antibody by direct ELISA and Cell ELISA. The direct ELISA, which was performed as described above, binding to proteins encoded by Pro115 Construct 2, and Cln242 Construct1 (negative control) was evaluated.

For the Cell ELISA, the binding of antibodies to RK3E cells stably transduced with either Pro115 (RK3E-Pro115-SA) or alkaline phosphatase (RK3E-AP; negative control) was evaluated. 25,000 cells in 100 ul growth medium were plated per well of a 96-well plate coated with Poly-D-Lysine (#15600, Pierce). Cells were incubated overnight, and 50 ul hybridoma supernatant or purified antibody (1 ug/ml final concentration) were added to each well. Cells were incubated on ice for 30 min. Wells were emptied and washed with TBST/BSA. Cells were then fixed for 10 min on ice by adding 100 ul 4% formaldehyde in TBS. Wells were emptied and washed with TBST/BSA. 300 ul TBST/BSA was added to each well. After incubating cells for 30 min at RT, wells were emptied and washed twice with TBST/BSA. 100 ul biotin-conjugated rabbit(Fab2) anti-mouse IgG (P/N315-066-046; Jackson Immunoresearch, West Grove, Pa.), diluted 1:20,000 in TBST/BS, were added per well to stain the cells. After 30 min incubation at RT, wells were emptied and washed twice with TBST/BSA. 100 ul Streptavidin-HRP conjugate (#21126; Pierce), diluted 1:20,000 in TBST/BSA, were added to each well and cells were incubated for 30 min at RT. Wells were washed twice with TBST/BSA. 100 ul of HRP substrate 3,3',5,5'-tetramethyl benzidine (#S1599; Dako Cytomation, Carpinteria, Calif.) were added. The reaction was stopped by adding 100 ul 1N hydrochloric acid, usually after 20 min or when the desired staining intensity was reached. The enzymatic reaction was quantified by measuring the solution's absorbance at 450 nm wavelength.

Evaluation of supernatants from hybridomas in direct ELISA and cell ELISA cells is shown in Table 2. Values in the last column (column 6) are the ratio of OD values from cells transduced with Pro115 (column 4) to cells transduced with alkaline phosphatase (column 5).

TABLE 2

| Clone # | Direct ELISA OD [405 nm] | | Cell ELISA OD [450 nm] RK3E- | | Pro115:AP ratio |
|---|---|---|---|---|---|
| | Pro115 Construct 2 | Cln242 Construct 1 | Pro115 cells | RK3E-AP cells | |
| B1 | 1.3064 | 0.1508 | 0.9892 | 0.2944 | 3.4 |
| B2 | 0.7695 | 0.1315 | 1.0996 | 0.3332 | 3.3 |
| B3 | 1.0286 | 0.1251 | 0.9038 | 0.3859 | 2.3 |
| B4 | 1.0292 | 0.0908 | 0.6268 | 0.3935 | 1.6 |
| B5 | 0.8952 | 0.0893 | 0.8809 | 0.4520 | 1.9 |
| B6 | 1.1827 | 0.0847 | 1.0687 | 0.4424 | 2.4 |
| B7 | 0.9649 | 0.0903 | 1.0307 | 0.4748 | 2.2 |
| B8 | 0.6000 | 0.0849 | 1.1025 | 0.3132 | 3.5 |
| B9 | 1.3498 | 0.1311 | 0.8373 | 0.3217 | 2.6 |
| B10 | 0.5779 | 0.1131 | 0.3590 | 0.2972 | 1.2 |
| B11 | 0.8952 | 0.1255 | 1.0869 | 0.3686 | 2.9 |
| B12 | 0.7692 | 0.1487 | 0.4794 | 0.4600 | 1.0 |
| B13 | 0.5551 | 0.1328 | 0.5080 | 0.4029 | 1.3 |
| B14 | 1.3539 | 0.1087 | 0.9859 | 0.3770 | 2.6 |
| B15 | 0.7326 | 0.1419 | 0.4957 | 0.3501 | 1.4 |
| 816 | 0.6789 | 0.1089 | 0.4645 | 0.2897 | 1.6 |
| B17 | 1.2082 | 0.0858 | 0.7619 | 0.2888 | 2.6 |
| B18 | 1.1609 | 0.0990 | 0.6447 | 0.3016 | 2.1 |
| B19 | 1.0495 | 1.4265 | 0.3724 | 0.2681 | 1.4 |
| B20 | 0.5922 | 0.0755 | 0.9259 | 0.3893 | 2.4 |
| B21 | 1.0629 | 0.0909 | 0.6376 | 0.3631 | 1.8 |
| B22 | 0.5780 | 0.0901 | 0.4196 | 0.3111 | 1.3 |
| B23 | 0.6406 | 0.0765 | 0.8860 | 0.3273 | 2.7 |
| B24 | 1.0601 | 0.0756 | 0.4474 | 0.3196 | 1.4 |
| B25 | 1.4708 | 0.0788 | 0.9597 | 0.3443 | 2.8 |
| B26 | 0.8612 | 0.0725 | 0.5162 | 0.4455 | 1.2 |
| B27 | 0.6300 | 0.0712 | 0.3933 | 0.3862 | 1.0 |
| B28 | 1.0939 | 0.0707 | 0.6197 | 0.4396 | 1.4 |
| B29 | 0.9180 | 0.0816 | 0.8671 | 0.2934 | 3.0 |
| B30 | 1.0810 | 0.0957 | 0.7064 | 0.6884 | 1.0 |
| B31 | 0.5389 | 0.0792 | 0.8135 | 0.3848 | 2.1 |
| B32 | 0.7776 | 0.0707 | 0.6028 | 0.4344 | 1.4 |
| B33 | 1.0041 | 0.1537 | 0.4214 | 0.2723 | 1.5 |
| B34 | 0.7255 | 0.1361 | 0.9487 | 0.3022 | 3.1 |
| B35 | 0.0897 | 0.1220 | 0.3343 | 0.2767 | 1.2 |
| B36 | 0.2022 | 0.1527 | 0.4554 | 0.4195 | 1.1 |
| B37 | 0.1477 | 0.1679 | 0.3871 | 0.3589 | 1.1 |
| B38 | 0.1586 | 0.1247 | 0.3953 | 0.2979 | 1.3 |
| B39 | 0.4560 | 0.1201 | 0.4370 | 0.3923 | 1.1 |
| B40 | 0.3565 | 0.0943 | 0.3109 | 0.2885 | 1.1 |
| B41 | 0.3313 | 0.0722 | 0.3843 | 0.3030 | 1.3 |
| B42 | 0.2089 | 0.0728 | 0.4389 | 0.4574 | 1.0 |
| B43 | 0.1879 | 0.0738 | 0.4412 | 0.4390 | 1.0 |
| B44 | 0.1416 | 0.0801 | 0.5787 | 0.6334 | 0.9 |
| B45 | 0.0881 | 0.0833 | 0.5593 | 0.5082 | 1.1 |
| B46 | 0.0715 | 0.0780 | 0.4392 | 0.3773 | 1.2 |
| B47 | 0.1023 | 0.0811 | 0.5300 | 0.5252 | 1.0 |
| B48 | 0.4945 | 0.0722 | 0.5469 | 0.4100 | 1.3 |
| B49 | 0.3490 | 0.0764 | 0.4462 | 0.5483 | 0.8 |
| B50 | 0.1172 | 0.0710 | 0.3423 | 0.2479 | 1.4 |
| B51 | 0.4495 | 0.0696 | 1.1329 | 0.5829 | 1.9 |
| B52 | 0.2492 | 0.0670 | 0.3861 | 0.2762 | 1.4 |
| B53 | 0.2704 | 0.0755 | 0.9000 | 0.3024 | 3.0 |
| B54 | 0.0939 | 0.0761 | 0.3913 | 0.3289 | 1.2 |
| B55 | 0.3086 | 0.0889 | 0.4052 | 0.3179 | 1.3 |
| B56 | 0.3672 | 0.0762 | 0.5163 | 0.2300 | 2.2 |
| B57 | 0.2947 | 0.1389 | 0.3990 | 0.3367 | 1.2 |
| B58 | 0.3650 | 0.1274 | 0.3170 | 0.2481 | 1.3 |
| B59 | 0.4041 | 0.1361 | 0.7632 | 0.2126 | 3.6 |
| B60 | 0.0845 | 0.1451 | 0.4519 | 0.3941 | 1.1 |
| B61 | 0.0806 | 0.1198 | 0.4669 | 0.3454 | 1.4 |
| B62 | 0.1221 | 0.1081 | 0.3660 | 0.3019 | 1.2 |
| B63 | 0.4344 | 0.0835 | 0.3918 | 0.3671 | 1.1 |
| B64 | 0.2089 | 0.1211 | 0.3694 | 0.2681 | 1.4 |
| B65 | 0.2957 | 0.1547 | 0.4746 | 0.5397 | 0.9 |
| B66 | 0.2248 | 0.0995 | 0.3960 | 0.3803 | 1.0 |
| B67 | 0.1017 | 0.1376 | 0.3143 | 0.2592 | 1.2 |
| B68 | 0.3047 | 0.0746 | 0.3950 | 0.3117 | 1.3 |
| B69 | 0.2215 | 0.0769 | 0.3823 | 0.3222 | 1.2 |

Selected hybridomas were expanded for further analysis.

D Series Antibodies

Hybridoma cell lines were selected for production of Pro115 specific antibody by direct ELISA as described above. Binding to proteins encoded by Pro115 Construct 2, and Cln242 Construct1 (negative control) was evaluated. Supernatants from hybridomas that produced an absorbance value of greater than 1.50 in wells coated with Pro115 Construct and less than 0.15 in wells coated with Cln242 Construct1 (negative control), indicated specific binding to Pro115. All thirteen specific hybridomas, named Pro115.D1 to Pro115.D13, were expanded and cryopreserved.

F Series Antibodies

Hybridoma cell lines were selected for production of Pro115 specific antibody by direct ELISA as described above. Supernatants from 2 hybridomas produced an absorbance value of greater than 0.5 in wells coated with Pro115

Construct 2 and less than 0.1 in wells coated with an irrelevant protein, indicating preferential antibody binding to Pro115. These hybridomas are designated F2 and F3.

Flow Cytometry Screening for Cell Surface Binding of Pro115 MAbs

Selected hybridoma supernatants were analyzed by flow cytometry for cell surface staining of transfected 293F cells and tumor cell lines.

293F cells were transiently transfected with expression plasmids for Pro115 Construct 1, Pro115v1 Construct 1, Pro104 Construct 1, and Ovr110 Construct 1 using 293fectin (Invitrogen) as transfection reagent. 48 hours post-transfection, cells were washed once with 10 ml $Ca^{+2}/Mg^{+2}$ free DPBS and then 7 ml of warm (37° C.) Cellstripper (Mediatech, Herndon, Va.) was added per 150 $cm^2$ flask. The cells were then incubated for 5 minutes at 37° C. with tapping of the flask to remove tightly attached cells. The cells were removed and pipetted several times to break aggregates, then immediately placed in DMEM/10% FBS/5 mM sodium butyrate. The cells were then centrifuged down for 5 minutes at 1300 rpm and resuspended in DMEM/10% FBS/5 mM sodium butyrate. The cells were incubated at 37° C. for a 30 minute recovery period. Prior to staining, viability of the cells was measured using Guava Viacount (Guava Cytometers, Foster City, Calif.) and cultures with >90% viability were selected for staining with MAbs.

Cells from cultures selected for MAb staining were aliquoted at 0.5-1.0×10⁶ cells/well in 96-well v-bottom plates (VWR) and centrifuged for 2 minutes at 1500 rpm. Supernatants were aspirated and plates briefly shaken on a vortex mixer to resuspend the cells, then 200 ul of DPBS/3% FBS/0.01% Na Azide (FACS buffer) was added to each well. Centrifugation and aspiration was repeated, then 25 uL of sequential dilutions of hybridoma supernatant or purified MAb was added to the cells. Plates were stored on ice for 15 min., then washed and centrifuged as above, in 200 uL of FACS buffer. This washing procedure was repeated twice and then 25 uL of phycoerythrin (PE) conjugated donkey anti-mouse IgG Fc antibody (Jackson Immunoresearch Laboratories) were added to cells. After 15 minutes on ice the cells were washed twice, as above and then resuspended in 250 uL of FACS buffer for analysis on an Elite fluorescent activated cell sorter (FACS) (Beckman-Coulter).

TABLE 3

Cell surface staining of transfected 293F cells with hybridoma supernatants

| | 293-Pro115 | | 293-Pro115v1 | | 293-Pro104 | | 293-Ovr110 | |
|---|---|---|---|---|---|---|---|---|
| | % cells positive | MFI | % cells positive | MFI | % cells positive | MFI | % cells positive | MFI |
| A1 | 96.2 | 7.490 | 64.8 | 0.691 | | | 22.8 | 0.344 |
| A2 | 37.3 | 0.558 | 6.7 | 0.304 | | | 1.9 | 0.233 |
| A3 | 27.8 | 0.455 | 6.4 | 0.315 | | | 1.3 | 0.236 |
| A4 | 48.7 | 0.614 | 1.4 | 0.259 | | | 1.6 | 0.221 |
| A5 | 97.8 | 12.500 | 15.3 | 0.369 | | | 1.0 | 0.216 |
| A6 | 23.9 | 0.435 | 2.3 | 0.266 | | | 0.9 | 0.211 |
| A7 | 37.8 | 0.552 | 93.2 | 2.220 | | | 86.3 | 1.100 |
| A8 | 98.7 | 10.500 | 61.1 | 0.643 | | | 38.5 | 0.406 |
| A9 | 42.1 | 0.627 | 3.2 | 0.269 | | | 1.5 | 0.223 |
| A10 | 45.0 | 0.875 | 1.1 | 0.257 | | | 0.7 | 0.208 |
| A11 | 62.2 | 0.809 | 1.2 | 0.260 | | | 0.9 | 0.216 |
| A12 | 91.2 | 2.060 | 2.1 | 0.264 | | | 1.1 | 0.221 |
| A13 | 39.7 | 0.580 | 3.1 | 0.280 | | | 1.6 | 0.229 |
| A14 | 16.4 | 0.382 | 2.4 | 0.262 | | | 1.7 | 0.219 |
| A15 | 2.1 | 0.275 | 2.0 | 0.271 | | | 0.7 | 0.218 |
| A16 | 11.9 | 0.349 | 1.3 | 0.257 | | | 0.5 | 0.214 |
| A17 | 97.8 | 9.850 | 16.1 | 0.371 | | | 1.4 | 0.237 |
| A18 | 59.0 | 0.721 | 4.8 | 0.298 | | | 1.8 | 0.230 |
| A19 | 19.2 | 0.403 | 0.7 | 0.244 | | | 0.7 | 0.214 |
| A20 | 46.1 | 0.637 | 85.2 | 2.690 | | | 86.5 | 2.530 |
| A21 | 28.5 | 0.503 | 2.6 | 0.270 | | | 0.7 | 0.218 |
| A22 | 64.8 | 0.837 | 8.6 | 0.311 | | | 2.1 | 0.237 |
| A23 | 69.9 | 1.010 | 2.6 | 0.266 | | | 0.9 | 0.219 |
| A24 | 95.7 | 6.840 | 2.7 | 0.267 | | | 0.6 | 0.210 |
| A25 | 50.1 | 0.631 | 2.5 | 0.266 | | | 1.9 | 0.222 |
| A101.1 | 43.5 | 0.653 | 3.2 | 0.279 | | | 1.2 | 0.223 |
| A107.1 | 76.3 | 3.17 | 10.5 | 0.363 | | | 1.3 | 0.302 |
| A108.1 | 41.2 | 0.791 | 5.1 | 0.286 | | | 2.1 | 0.230 |
| B2 | 23.6 | 5.81 | 2.2 | 1.57 | 80.4 | 3.58 | 70.2 | 2.26 |
| B3 | 67.2 | 3.68 | 1.5 | 0.48 | 1.5 | 0.332 | 2.5 | 0.334 |
| B5 | 87.6 | 3.96 | 3.6 | 1.73 | 80.8 | 2.43 | 74.1 | 1.93 |
| B7 | 59.9 | 3.72 | 1.7 | 0.439 | 0.7 | 0.314 | 1.2 | 0.305 |
| B8 | 19.9 | 5.75 | 1.1 | 0.422 | 1 | 0.317 | 1.1 | 0.308 |
| B20 | 22.7 | 5.82 | 1.2 | 0.526 | 10.2 | 0.136 | 8.8 | 0.379 |
| B22 | 97.1 | 12.8 | 63.6 | 7.71 | 97.1 | 5.15 | 91.4 | 3.41 |
| B23 | 22.2 | 5.9 | 1.1 | 0.465 | 1.9 | 0.337 | 2.6 | 0.34 |
| B29 | 22.9 | 5.49 | 1.4 | 0.438 | 0.9 | 0.305 | 1.5 | 0.313 |
| B31 | 33.9 | 4.81 | 1.2 | 0.429 | 0.9 | 0.313 | 1.2 | 0.313 |
| B34 | 36.5 | 4.62 | 1.4 | 0.471 | 1.1 | 0.344 | 1.7 | 0.321 |
| B48 | 76.7 | 4.06 | 1.2 | 0.45 | 1.3 | 0.334 | 1.6 | 0.324 |
| B53 | 22.2 | 6.6 | 1.5 | 0.617 | 16.4 | 1.01 | 12.9 | 0.456 |
| B56 | 92.8 | 5.01 | 1.9 | 1.5 | 80.1 | 1.7 | 68.7 | 1.33 |
| B64 | 98.8 | 23.8 | 97 | 23.6 | 99.7 | 28.1 | 94.9 | 6.01 |
| D1 | 11 | 0.388 | | | | | 4.8 | 0.353 |
| D2 | 34.9 | 0.627 | | | | | 0.6 | 0.326 |
| D3 | 32.9 | 0.575 | | | | | 0.3 | 0.317 |
| D4 | 10.4 | 0.397 | | | | | 2 | 0.35 |
| D5 | 29.4 | 0.585 | | | | | 3.8 | 0.273 |
| D6 | 44 | 0.756 | | | | | 0.3 | 0.315 |
| D7 | 34.8 | 0.591 | | | | | 1.4 | 0.342 |
| D8 | 0.8 | 0.313 | | | | | 0.2 | 0.32 |
| D9 | 5.4 | 0.369 | | | | | 0.3 | 0.331 |
| D10 | 18 | 0.416 | | | | | 0.1 | 0.3 |
| D11 | 1.5 | 0.302 | | | | | 0.4 | 0.312 |
| D12 | 19.5 | 0.436 | | | | | 0.2 | 0.306 |
| D13 | 31.3 | 0.556 | | | | | 0.2 | 0.327 |

Hybridomas producing anti-Pro115 MAbs that bound specifically to cells expressing Pro115 at the cell surface but not to negative control cells with surface protein Ovr110 were further analyzed by flow cytometry for cell surface staining of tumor cell lines LNCaP and HCT116.

Culture and Stimulation of Cancer Cell Lines

LNCaP cells natively express Pro115 and expression levels can be further upregulated by addition of the hormone mibolerone to the culture medium. HCT116 cells do not express Pro115 and served as negative control. Using standard cell culture techniques and methods cancer cell lines LNCaP (CRL-1740; ATCC, Manassas, Va.) and HCT-116 (CCL-247; ATCC) were cultured in RPMI/10% FBS and DMEM/10% FBS, respectively. LNCaP cells were stimulated for 48 hours by adding Mibolerone (Perkin Elmer Life and Analytical Science, Wellesley, Mass.) to the culture medium to a final concentration of 10 nM. Anti-Pro115, anti-Ricin (negative control) and anti-CD71 (positive control) antibodies were evaluated for binding to un-stimulated and stimulated LNCaP cells and HCT-116 cells. Percent positive cells and the MFI for each cell antibody and cell type are listed in Table 4 below.

TABLE 4

Cell surface staining of cancer cell lines with hybridoma supernatants.

| | Stimulated LNCaP | | Unstimulated LNCaP | | HCT116 | |
|---|---|---|---|---|---|---|
| Sample | % Cells Positive | MFI | % Cells Positive | MFI | % Cells Positive | MFI |
| Anti-Ricin | 3.8 | 0.463 | 0.9 | 0.262 | 2.6 | 0.306 |
| Anti-CD71 | 19.7 | 0.958 | 98.1 | 7.17 | 81.8 | 2.58 |
| B3 | 35.5 | 1.65 | 45 | 0.878 | 1.2 | 0.289 |
| B7 | 32.9 | 1.56 | 38.2 | 0.776 | 0.5 | 0.271 |
| B8 | 24.3 | 1.14 | 28.2 | 0.668 | 0.7 | 0.273 |
| B20 | 30.2 | 1.44 | 39.2 | 0.787 | 1.7 | 0.312 |
| B23 | 31.4 | 1.48 | 42.9 | 0.834 | 1.2 | 0.292 |
| B29 | 31.1 | 1.46 | 39.2 | 0.802 | 1.2 | 0.288 |
| B31 | 49.8 | 2.22 | 79.8 | 1.53 | 1 | 0.291 |
| B34 | 55.3 | 2.56 | 84.2 | 1.69 | 1.2 | 0.296 |
| B48 | 44.9 | 2.03 | 70.4 | 1.3 | 4.4 | 0.34 |
| B53 | 38 | 1.79 | 57.2 | 1.05 | 1.2 | 0.295 |
| D1 | 34.4 | 0.766 | 1.6 | 0.377 | 20.8 | 0.494 |
| D2 | 74.6 | 1.9 | 3.4 | 0.351 | 2.7 | 0.285 |
| D3 | 62.7 | 1.3 | 3.6 | 0.328 | 1.2 | 0.218 |
| D4 | 56.3 | 1.1 | 2.8 | 0.355 | 2.9 | 0.289 |
| D5 | 5.3 | 0.461 | 8.2 | 0.335 | 4.6 | 0.266 |
| D6 | 35.4 | 0.797 | 0.3 | 0.306 | 2 | 0.246 |
| D7 | 63.9 | 1.34 | 7.3 | 0.43 | 11.6 | 0.368 |
| D8 | 6.5 | 0.49 | 0.7 | 0.268 | 1.1 | 0.247 |
| D9 | 38.4 | 0.883 | 3.3 | 0.307 | 2.2 | 0.266 |
| D10 | 43.6 | 0.949 | 0.9 | 0.282 | 0.1 | 0.194 |
| D11 | 30.9 | 0.776 | 0.7 | 0.277 | 1 | 0.231 |
| D12 | 43 | 0.927 | 0.6 | 0.289 | 0.5 | 0.251 |
| D13 | 78.6 | 1.82 | 9 | 0.444 | 35.1 | 0.512 |
| F2 | 69.4 | 1.250 | | | 0.1 | 0.275 |
| F3 | 49.9 | 0.766 | | | 0.3 | 0.282 |

The results in Table 4 above demonstrate that all tested B and F series antibodies specifically bind to Pro115-positive LNCaP cells, but not to Pro115-negative HCT116 cells. Cell surface binding can be enhanced by stimulating LNCaP cells with mibolerone, which upregulates Pro115 expression. Antibodies D1 and D15 stained HCT116 cells indicating that these antibodies cross-reacted with a protein other than Pro115. The other D series antibodies specifically bound to stimulated LNCaP cells.

Cloning of Hybridomas Producing Pro115 Specific MAb

Based on data from the ELISA and flow cytometry experiments above, the following hybridomas were selected for single cell cloning into 96 well culture plates by cell sorting (Coulter Elite): A1, A4, A5, A8, A12, A107.1, B3, B7, B20, B23, B29, B31, B34, B53, D2, D3, D5, D7, D9, D10, D11, D12, F2 and F3.

After 2 weeks of culture, supernatants from subcloned hybridomas were tested by direct ELISA on wells coated with Pro115 Construct 1. Up to 3 positive subclones per parent hybridoma were expanded and cryopreserved in liquid nitrogen. MAbs were purified from overgrown hybridoma supernatants and analyzed by flow cytometry for cell surface binding of Pro115-transfected 293F cells as well as binding to tumor cell lines. Flow Cytometry binding results are displayed below in Tables 5 and 6.

TABLE 5

Cell surface staining of Pro115 transfected 293F cells with purified MAbs.

| | Pro115-Transfected 293F Cells | | Control 293F Cells | |
|---|---|---|---|---|
| Sample | % Cells Positive | Mean Fluorescence Intensity | % Cells Positive | Mean Fluorescence Intensity |
| Anti-Ricin | 0.9 | 0.425 | 0.9 | 0.324 |
| Anti-CD71 | 18.6 | 5.6 | 99.7 | 21 |
| A1.1 | 86 | 4.27 | 1.5 | 0.34 |
| A4.1 | 9.2 | 0.695 | 0.7 | 0.316 |
| A5.1 | 88.2 | 4.97 | 1.9 | 0.329 |
| A8.1 | 82.8 | 4.29 | 54.7 | 1.95 |
| A12.1 | 3.7 | 0.569 | 20.6 | 1.05 |
| A17.1 | 85.3 | 7.38 | 23.0 | 0.83 |
| A22.1 | 34.2 | 0.96 | 67.2 | 2.99 |
| A24.1 | 28.4 | 0.83 | 8.4 | 0.52 |
| A107.1.1 | 92.4 | 10.90 | 31.0 | 0.95 |
| B3.1 | 96.6 | 11.20 | 56.3 | 1.96 |
| B7.1 | 93.4 | 9.99 | 2.5 | 0.51 |
| B20.1 | 78.7 | 5.83 | 0.0 | 0.30 |
| B23.1 | 71.3 | 4.70 | 0.0 | 0.25 |
| B29.1 | 77.4 | 5.54 | 0.1 | 0.31 |
| B31.1 | 70.6 | 4.46 | 0.2 | 0.39 |
| B34.1 | 80.0 | 5.67 | 1.3 | 0.45 |
| B53.1 | 68.2 | 4.15 | 0.0 | 0.29 |

TABLE 6

Cell surface staining of cancer cell lines with purified MAbs.

| | Stimulated LNCaP | | Unstimulated LNCaP | | HCT116 | |
|---|---|---|---|---|---|---|
| Sample | % Cells Positive | MFI | % Cells Positive | MFI | % Cells Positive | MFI |
| Anti-Ricin | 3.8 | 0.463 | 0.9 | 0.262 | 2.6 | 0.306 |
| Anti-CD71 | 19.7 | 0.958 | 98.1 | 7.17 | 81.8 | 2.58 |
| A1.1 | 92.0 | 5.160 | 7.6 | 0.386 | 2.3 | 0.295 |
| A4.1 | 15.4 | 0.606 | | | 3.0 | 0.301 |
| A5.1 | 92.0 | 5.170 | 17.6 | 0.534 | 2.6 | 0.300 |
| A8.1 | 89.9 | 4.520 | | | 7.7 | 0.346 |
| A12.1 | 35.1 | 0.947 | | | 4.1 | 0.318 |
| A17.1 | 73.7 | 2.420 | 37.2 | 1.32 | 3.6 | 0.307 |
| A22.1 | 45.4 | 1.220 | 32.0 | 1.21 | 88.8 | 2.110 |
| A24.1 | 69.9 | 2.570 | 24.9 | 1.12 | 5.4 | 0.341 |
| A107.1.1 | 88.9 | 4.490 | 31.7 | 1.26 | 4.1 | 0.312 |
| B3.1 | 99.7 | 27.900 | 86.2 | 3.32 | 1.3 | 0.271 |
| B7.1 | 99.7 | 28.200 | 16.9 | 1.00 | 1.4 | 0.274 |
| B20.1 | 99.3 | 25.800 | 16.2 | 0.95 | 1.7 | 0.278 |
| B23.1 | 99.3 | 25.200 | 7.3 | 0.80 | 1.3 | 0.268 |
| B29.1 | 99.4 | 27.500 | 22.8 | 1.09 | 1.6 | 0.276 |
| B31.1 | 99.2 | 24.100 | 15.8 | 0.97 | 1.7 | 0.275 |
| B34.1 | 99.7 | 26.500 | 30.2 | 1.23 | 1.8 | 0.271 |
| B53.1 | 99.2 | 24.100 | 6.1 | 0.77 | 1.1 | 0.261 |
| D2.1 | 70.8 | 2.710 | 1.9 | 0.351 | 14.8 | 0.425 |
| D3.1 | 70.9 | 2.460 | 4.6 | 0.438 | 25.8 | 0.512 |
| D5.1 | 39.3 | 1.060 | 6.7 | 0.406 | 62.6 | 0.964 |
| D7.1 | 65.8 | 2.010 | 2.4 | 0.331 | 51.9 | 0.744 |
| D9.1 | 71.8 | 2.500 | 0.3 | 0.287 | 36.9 | 0.611 |
| D10.1 | 52.0 | 1.510 | 0 | 0.254 | 2.0 | 0.289 |
| D11.1 | 52.0 | 1.470 | 0 | 0.252 | 2.5 | 0.285 |
| D12.1 | 17.0 | 0.643 | 0 | 0.254 | 2.2 | 0.287 |
| F2.1 | 99.7 | 26.0 | | | 2.6 | 0.312 |
| F3.11 | 99.3 | 32.0 | | | 6.6 | 0.365 |

MAbs A22.1, D2.1, D3.1, D5.1, D7.1 and D9.1 bound nonspecifically to Pro115-negative cells. All other MAbs of the A-, B-, D- and F series listed in Tables 5 and 6 bound specifically to Pro115-expressing cells demonstrating that the subcloned hybridomas robustly produced anti-Pro115 specific MAbs.

Pro115 MAb Checkerboard ELISA

A checkerboard ELISA was ran with Pro115 A and B series Mabs. High binding polystyrene plates (Corning Life Sciences) were coated overnight at 4° C. with 0.2 µg/well of a first anti-Pro115 MAb. The coating solution was aspirated off and free binding sites were blocked with 300 µl/well Superblock-TBS (Pierce Biotechnology, Illinois) on a shaker for 1 hour at room temperature (RT). After washing 4 times with washing buffer (TBS+0.05% Tween20), 100 µl of Pro115 Construct 2 protein at 2 µg/ml (in Assay Buffer (TBS, 1% BSA, 1% Mouse Serum, 1% Calf Serum, and 0.1% ProClin™) was added to each well. The plate was incubated for 60 minutes on a shaker. For detection, 100 µl of a second biotinylated MAb (0.2 µg/ml) was added to each well and incubated for 1 hour at room temperature (RT), while shaking. After washing, 100 µL of Streptavidin-HRP conjugate (Jackson Lab) at 1:80,000 dilution in TBS, was added to each well. Plates were then incubated with shaking at RT for 30 min. After washing the plate, 100 uL/well of TMB-Stable Stop substrate (Moss, Inc.) was added to each well and the plate was incubated at RT, covered and on the shaker for 15 minutes. The reaction was stopped using 100 µl/well 1N HCl, and the plates were read at 450 nm using a Spectramax 190 plate reader (Molecular Devices).

The results of the checkerboard ELISA are shown in Table xxx. Capturing MAbs are listed on the Y-axis with detecting MAbs on the X-axis. Each antibody was tested as both a coating and detecting antibody, in all possible combinations. OD numbers at 450 nm are shown. Similar pairing patterns of antibodies indicate that these antibodies bind to similar epitopes. The anti-Pro115 MAbs shown in Table 7 detect at least six distinct epitopes. Antibodies A1.1, A107.1, A5.3 and A8.1 (group 1) recognize a similar epitope. Antibodies B20.1, B23.1, B29.1, B31.1 and B34.1 (group 2) recognize a similar epitope which is different the epitope recognized by group 1. Antibodies A4.1, A25.1 and A102.1 (group 3) recognize a similar epitope which is distinct from the epitopes recognized by groups 1 and 2. Antibodies B3.1 and B7.1 recognize a similar epitope which is different from the epitope recognized by groups 1, 2, and 3. Antibodies A12.1 and B53.1 are unique. Their pairing patterns do not resemble the pairing pattern of any other antibody indicating that they bind to epitopes distinct from the epitopes recognized by the other antibodies.

For formatting convenience, the antibody nomenclature of Table 7 below has been simplified to show the parent name only (e.g. A4) and not the full clone name (e.g. A4.1).

TABLE 7

Checkerboard ELISA with selected Pro115 MAbs

| coat 1° Mab | detecting 2° MAb | | | | | | | | | | | | | | | |
|---|---|---|---|---|---|---|---|---|---|---|---|---|---|---|---|---|
| | A1 | A107 | A5 | A8 | B23 | B31 | B29 | B34 | B20 | B53 | A4 | A102 | A25 | A12 | B7 | B3 |
| A1 | 0.15 | 0.2 | 0.37 | 0.29 | 3.72 | 2.97 | 4 | 3.99 | 4 | 1.67 | 2.54 | 1.12 | 2.05 | 0.8 | 4 | 4 |
| A5 | 0.09 | 0.14 | 0.18 | 0.16 | 3.95 | 3.05 | 4 | 4 | 4 | 2.52 | 2.44 | 0.92 | 1.89 | 0.78 | 4 | 4 |
| A8 | 0.26 | 0.28 | 0.56 | 0.48 | 3.95 | 3.29 | 4 | 4 | 4 | 2.03 | 4 | 1.54 | 2.68 | 1.14 | 4 | 4 |
| A107 | 0.05 | 0.1 | 0.08 | 0.07 | 2.69 | 1.56 | 3.27 | 3.01 | 3.92 | 1.4 | 1.45 | 0.59 | 1.07 | 0.48 | 3.96 | 4 |
| B53 | 1.23 | 1.36 | 2.37 | 2.65 | 3.82 | 2.99 | 3.92 | 3.34 | 4 | 0.12 | 0.49 | 0.21 | 0.38 | 0.21 | 3.98 | 4 |
| A4 | 3.12 | 2.63 | 3.94 | 4 | 2.39 | 1.89 | 3.76 | 3.49 | 3.86 | 1.14 | 0.37 | 0.16 | 0.37 | 1.09 | 4 | 4 |
| A25 | 3.37 | 3.02 | 3.97 | 4 | 1.83 | 1.19 | 2.76 | 3.06 | 3.62 | 0.89 | 0.62 | 0.24 | 0.36 | 0.99 | 4 | 4 |
| A102 | 1.02 | 0.97 | 2.02 | 1.64 | 0.38 | 0.23 | 0.77 | 0.77 | 0.98 | 0.31 | 0.19 | 0.07 | 0.13 | 0.25 | 2.09 | 2.55 |
| B31 | 2.6 | 2.79 | 3.42 | 4 | 0.27 | 0.17 | 0.77 | 0.98 | 1.04 | 2.39 | 1.03 | 0.42 | 0.85 | 0.42 | 3.83 | 3.99 |
| B29 | 2.87 | 3.13 | 3.71 | 4 | 0.1 | 0.09 | 0.2 | 0.25 | 0.28 | 3.91 | 0.96 | 0.37 | 0.87 | 0.61 | 3.93 | 4 |
| B34 | 3.51 | 3.54 | 3.88 | 4 | 0.1 | 0.12 | 0.22 | 0.26 | 0.28 | 4 | 1.28 | 0.45 | 0.91 | 0.61 | 4 | 4 |
| B20 | 3.96 | 4 | 4 | 4 | 0.14 | 0.13 | 0.37 | 0.46 | 0.56 | 4 | 1.49 | 0.56 | 1.11 | 0.83 | 4 | 4 |
| B23 | 4 | 4 | 4 | 4 | 0.2 | 0.16 | 0.7 | 0.73 | 0.96 | 4 | 3.03 | 0.98 | 2.02 | 1.46 | 4 | 4 |
| A12 | 2 | 1.95 | 2.78 | 2.94 | 1.43 | 0.99 | 2.35 | 2.66 | 2.99 | 0.48 | 1.5 | 0.57 | 0.94 | 0.14 | 2.05 | 2.55 |
| B3 | 3.15 | 3.7 | 4 | 4 | 3.92 | 3.19 | 4 | 4 | 4 | 3.99 | 1.74 | 0.63 | 1.1 | 0.29 | 0.3 | 0.32 |
| B7 | 4 | 3.93 | 4 | 4 | 4 | 4 | 4 | 4 | 4 | 4 | 3.02 | 1.16 | 1.89 | 0.54 | 0.62 | 1.02 |

Pro115 MAb Competition ELISA

A competition ELISA was ran with selected Pro115 Mabs. High binding polystyrene plates (Corning Life Sciences) were coated overnight at 4° C. with 0.2 µg/well monoclonal antibody against a hexa-Histidine tag. The coating solution was aspirated off and free binding sites were blocked with 300 µl/well TBST/BSA for 1 hour. After washing 3 times with TBST buffer, 100 µl of Pro115 Construct 2 protein at 2 µg/ml (in TBST/BSA) was added to each well. The plate was incubated for 60 minutes on a shaker and washed 3 times with TBST buffer. One-hundred µl of a first, unlabeled Pro115 MAb (20 µg/ml in TBST/BSA) was added to each well, followed by incubation for 30 minutes. Forty µl of a second, biotinylated Pro115 MAb (7 µg/ml in TBST/BSA) was added to each well, followed by incubation for 30 minutes. The plate was washed and 100 µl of Streptavidin-AP conjugate (Jackson Lab) at 1:2,000 dilution in TBST/BSA was added to each well. Plates were then incubated for 30 min. After washing the plate, 100 uL/well of pNPP substrate was added to each well, the plate was incubated for 60 minutes and read at 405 nm.

The results of the competition ELISA are shown in Table 8. Unlabeled competition MAbs are listed on the Y-axis with biotinylated detecting MAbs on the X-axis. Each antibody was tested as both a competing and detecting antibody, in all possible combinations. Numbers shown are OD values for a pair of competition and detecting MAbs normalized to the OD value of the same detecting MAb in combination with an irrelevant competition MAb which does not bind to Pro115. A ratio of 1.0 indicates that the competition MAb does not block the binding of the detecting MAb to Pro115; both MAbs bind to different epitopes. A ratio close to 0.0 indicates that the competition MAb blocks the binding of the detecting MAb to Pro115; both MAbs bind to similar or identical epitopes. Antibodies A5.3 and A8.1 block each other and both are blocked by A4.1, indicating that they bind to similar or identical epitopes. Antibodies B34.1 and F2.1 block each other and are not significantly blocked by other antibodies, indicating that they bind to similar or identical epitopes. Antibodies A24.1, B53.1, D11.1, D3.1, A17.1, D2.1, B7.1 and F3.11.1 have unique inhibition patterns suggesting that each antibody binds to a distinct epitope. Binding of F3.11.1 is not inhibited by any other antibody, indicating that its epitope is distant from epitopes recognized by other Pro115 MAbs.

TABLE 8

Competition ELISA with selected Pro115 MAbs.

| comp Mab | detecting Mab | | | | | | | | | | | |
|---|---|---|---|---|---|---|---|---|---|---|---|---|
| | A4.1 | A24.1 | B53.1 | D11.1 | D3.1 | A17.1 | A5.3 | A8.1 | D2.1 | F3.11.1 | F2.1 | B34.1 | B7.1 |
| A4.1 | 0.82 | 0.22 | 0.44 | 0.44 | 0.39 | 0.15 | 0.11 | 0.01 | 0.46 | 0.89 | 0.95 | 0.48 | 0.31 |
| A5.3 | 0.88 | 0.26 | 0.42 | 0.31 | 0.37 | 0.1 | 0.01 | 0 | 0.4 | 0.87 | 0.96 | 0.66 | 0.44 |
| A8.1 | 1.17 | 0.51 | 0.66 | 0.69 | 0.51 | 0.23 | 0.04 | 0 | 0.59 | 0.86 | 0.96 | 0.77 | 0.65 |
| A17.1 | 1.04 | 0.67 | 0.99 | 0.59 | 0.35 | −0.02 | 0.83 | 0.88 | 0.92 | 1.01 | 0.94 | 0.95 | 0.77 |
| D3.1 | 0.71 | 0.57 | 0.45 | 0.06 | 0.03 | 0.45 | 0.71 | 0.71 | 1 | 0.75 | 0.99 | 0.71 | 0.6 |
| D11.1 | 0.91 | 0.65 | 1.2 | 0.1 | 0.74 | 0.82 | 0.82 | 0.84 | 1.26 | 0.94 | 1.08 | 1.15 | 0.91 |
| D2.1 | 0.66 | 0.48 | 0.69 | 1.12 | 0.56 | 0.35 | 0.65 | 0.67 | 0.02 | 0.78 | 0.97 | 0.78 | 0.69 |
| A24.1 | 0.76 | 0.04 | 0.92 | 0.83 | 0.33 | 0.47 | 0.76 | 0.71 | 0.86 | 0.79 | 0.95 | 0.99 | 0.84 |
| B7.1 | 1.26 | 0.8 | 1.64 | 1.35 | 0.53 | 0.66 | 1.01 | 0.7 | 1.06 | 1.33 | 0.96 | 1.01 | 0.02 |
| B3.1 | 0.89 | 0.98 | 2.01 | 1.67 | 1.17 | 0.47 | 0.81 | 0.67 | 1.21 | 1.46 | 0.86 | 0.96 | 0.03 |
| B34.1 | 0.86 | 0.54 | 1.48 | 1.25 | 0.75 | 0.49 | 0.64 | 0.93 | 0.75 | 1.54 | 0.05 | 0.01 | 0.74 |
| F2.1 | 0.93 | 0.91 | 1.94 | 1.74 | 1.07 | 0.97 | 0.92 | 0.95 | 1.24 | 1.77 | 0.14 | 0.04 | 1.06 |
| B53.1 | 0.94 | 0.59 | 0.02 | 1.07 | 0.89 | 0.59 | 0.8 | 0.83 | 0.88 | 1.04 | 0.96 | 0.8 | 0.77 |
| F3.11.1 | 1.12 | 0.74 | 1.77 | 1.07 | 0.83 | 0.79 | 0.86 | 0.82 | 1.11 | 0.1 | 0.98 | 0.98 | 0.97 |

Off-Ranking Analysis of Pro115 mAbs

Dissociation rate constants (kd) were calculated from surface plasmon resonance measurements using a BIACORE 3000 instrument (BiaCore, Piscataway, N.J.). An anti-Mouse Ig surface was used to capture each antibody, followed by an injection of the protein encoded by Pro115 Construct 2 over the captured antibody.

Flow cell 1 of a CM5 sensor chip (BiaCore) was used as a control surface for reference subtractions, and was activated and derivatized with nonspecific rabbit IgG using standard methods. Flow cells 2, 3, and 4 were derivatized with anti-Mouse IgG diluted to 35 ug/mL in 10 mM acetate as suggested. Standard amine coupling (BiaCore) was used to immobilize approximately 12000 RU of ligand per flow cell. Purified antibodies were diluted in HBS-EP running buffer (BiaCore) to 20 ug/mL and passed over flow cells 2, 3, or 4 at 15 uL/min flow rate, 3 minute injection. Following mouse Ig loading, 31 ug/mL Pro115 Construct 2 protein was injected at 10 uL/minute for 3.4 minutes. The dissociation time was 5 minutes. The regeneration of the chip surface, or removal of captured hybridoma supernatants binding to the antigen between cycles, was performed by injecting 10 mM glycine pH 2.0 for 20 seconds and 10 mM glycine pH 1.5 for 10 seconds at 100 uL/minute.

The sensor chip derivatization procedure was performed by using the BiaCore's surface preparation and binding wizard included in the BiaCore control software. The off-ranking results presented in Table 9a below were automatically fitted using the separate ka/kd function included in the BiaCore analysis software, assuming a 1:1 Langmuir binding model.

TABLE 9a

Pro115 mAb kinetics

| Mab | kd | Mab RU | Antigen RU |
|---|---|---|---|
| A1.1 | 2.55E−04 | 625.3 | 124.5 |
| A4.1 | 1.31E−04 | 459.9 | 141.2 |
| A5.1 | 1.96E−04 | 433.4 | 130.6 |
| A8.1 | 3.36E−04 | 957.3 | 157.9 |
| A22.1 | 1.91E−04 | 821.2 | 202.7 |
| A25.1 | 1.31E−04 | 401.3 | 121.9 |
| A107.1.1 | 1.69E−04 | 681.5 | 145.5 |
| A123.1.1 | 6.27E−04 | 378.6 | 117.6 |
| B7.1 | 2.26E−04 | 314.4 | 153.2 |
| B20.1 | 2.39E−04 | 414.6 | 225.4 |
| B23.1 | 7.24E−04 | 312.6 | 164.8 |
| B29.1 | 1.73E−04 | 321.8 | 180 |

TABLE 9a-continued

Pro115 mAb kinetics

| Mab | kd | Mab RU | Antigen RU |
|---|---|---|---|
| B31.1 | 1.16E−03 | 449.5 | 216.2 |
| B34.1 | 3.05E−04 | 414.4 | 242.9 |
| B53.1 | 4.05E−04 | 211.8 | 120.1 |
| D2.1 | 4.07E−04 | 524.8 | 169.9 |
| D3.1 | 2.27E−04 | 601.4 | 152.4 |
| D5.1 | 2.49E−04 | 389.6 | 122.2 |
| F2.1 | 3.24E−04 | 422.5 | 207.9 |
| F3.11.1 | 3.41E−04 | 554.5 | 223.7 |

These results demonstrate that anti-Pro115 antibodies are useful as diagnostic or therapeutic agents. Pro115 MAbs in table 9a have kd values and binding characteristics (described herein) which demonstrate their utility as diagnostic agents.

Affinity Measurements of Pro115 Antibodies

ELISA plates were coated with 0.3 ug anti-His antibody His.A6.1 (in 100 ul PBS) and blocked with 300 ul TBST/BSA. Twenty-five ng of Pro115 Construct2 protein in 100 ul TBST/BSA were added to each well and plates were incubated for 1 hour. Plates were washed 3 times with 300 ul TBST. One-hundred ul of biotinylated Pro115 antibody was added to each well. The concentration of the antibody ranged from 1 uM to 0.5 nM. Plates were incubated for 3 hours and washed 3 times with 300 ul TBST. One-hundred ul Streptavidin-AP conjugate (1:2000 dilution in TBST/BSA; Jackson Immunoresearch) was added to each well. Plates were incubated for 30 min and washed 3 times with 300 ul TBST. The alkaline phosphatase signal was developed by addition of pNPP substrate and quantified by OD measurement at 405 nm. OD signals generated by a negative control antibody were subtracted from OD signals generated by Pro115 antibodies at equivalent antibody concentrations. Binding curves (net OD values plotted against the antibody concentration) were analyzed with the software Prism (GraphPad). The dissociation constant KD was calculated by nonlinear regression assuming a one-site binding model. Table 9b below list the KD in nanomolar concentration of Pro115 antibodies.

TABLE 9b

Pro115 antibody affinities

| mAb | KD [nM] |
|---|---|
| B7.1 | 0.11 |
| B34.1 | 0.23 |
| B53.1 | 1428 |
| F2.1 | 0.19 |
| F3.11.1 | 603 |

These results demonstrate that anti-Pro115 antibodies are useful as diagnostic or therapeutic agents. An antibody with nanomolar range affinity is considered useful as a therapeutic agent. Pro115 MAbs B7.1, B34.1, F2.1 and F3.11.1 have KD values and binding characteristics (live cell binding) which demonstrate their utility as therapeutic agents.

Pro115 MAb Isotypes

The isotypes of the anti-Pro115 MAbs were determined using commercially available mouse monoclonal antibody isotyping immunoassay test kits (IsoStrip, Roche Diagnostic Corp., Indianapolis, Ind.). Results of the isotyping are listed in Table 10.

TABLE 10

Pro115 MAb Isotypes

| Clone | Isotype |
|---|---|
| A4.1 | IgG1 kappa |
| A5.1 | IgG1 kappa |
| A12.1 | IgG2a kappa |
| A107.1 | IgG1 kappa |
| B7.1 | IgG1 kappa |
| B34.1 | IgG1 kappa |

Western Blots

Protein extracts for western blot analysis were prepared from transfected RK3E-Pro115 and control RK3E-AP (alkaline phosphatase) cells as well as from different cancer cell lines Colo-205 (CCL-222, ATCC), T84 (CLL-248; ATCC), LNCaP and HCT-116. Colo-205, T84 and LNCaP are Pro115 positive, and HCT-116 is Pro115 negative as judged by quantitative PCR analysis. Cells were incubated for 10 min in Cell Lysis Buffer (50 mM Tris, pH7.5, 50 mM NaCl, 2 mM EDTA, 1% NP-40; complete protease inhibitors (Roche) were added freshly). The lysate was centrifuged for 10 min at 4° C. at 10,000 g and the protein concentration of the cleared supernatant was determined (BCA Assay, #23227; Pierce). Fifteen ug total proteins were separated by electrophoresis on NuPAGE 4-12% Bis-Tris gels (Invitrogen) under denaturing conditions in Novex-XCell II Minicell gel apparatus (Invitrogen) and subsequently transferred to PVDF membranes using an XCell II Blot Module (Invitrogen Life Technologies). Following the transfer of proteins, the membranes were blocked in TBST with 5% non fat milk at room temperature for at least an hour, followed by incubation overnight at 4° C. with primary antibody (hybridoma supernatant or purified MAb at 2 ug/mL), and then with horseradish-peroxidase conjugated goat anti-mouse IgG secondary antibody (Jackson Immunoresearch Laboratories, Inc.) for one hour. The membranes were visualized by chemiluminescence using an ECL advance western blotting detection kit (Amersham Biosiences, Piscataway, N.J.). The HA antibody was from obtained from Covance (Berkeley, Calif.). Results of western blot experiments with anti-Pro115 A-series MAbs and D-series MAbs are summarized in Tables 11 and 12. Band intensity is categorized as weak (−), intermediate (+/−), strong (+), or not detected (ND). The size of the band(s) detected is also indicated.

TABLE 11

Pro115 A-series MAb Western Blot Results.

| | | Cell line | | | | | | | |
|---|---|---|---|---|---|---|---|---|---|
| | | RK3E-Pro115HA | | RK3E-AP | | Colo-205 | | T84 | |
| MAb | | Bands detected | Intensity | Bands detected | Intensity | Bands Detected | Intensity | Bands detected | Intensity |
| Anti-HA | | 54 kDa | +/− | none | | | | | |
| | | 28 kDa | +/− | | | | | | |
| A1.1 | | 54 kDa | + | none | | 54 kDa | +/− | 54 kDa | +/− |
| | | 38 kDa | − | | | 38 kDa | + | 38 kDa | + |
| A4.1 | | 54 kDa | +/− | none | | 54 kDa | − | 54 kDa | − |
| | | 28 kDa | +/− | | | 28 kDa | − | 28 kDa | − |
| A5.1 | | 54 kDa | + | none | | 54 kDa | +/− | 54 kDa | +/− |
| | | 38 kDa | +/− | | | 38 kDa | + | 38 kDa | + |
| | | 16 kDa | +/− | | | 16 kDa | − | 16 kDa | − |
| A8.1 | | 54 kDa | +/− | none | | 54 kDa | − | 54 kDa | − |
| | | 38 kDa | − | | | 38 kDa | +/− | 38 kDa | +/− |
| | | 16 kDa | − | | | | | | |
| A12.1 | | 54 kDa | + | none | | 54 kDa | +/− | 54 kDa | +/− |
| | | 38 kDa | +/− | | | 38 kDa | + | 38 kDa | + |
| | | 16 kDa | +/− | | | 16 kDa | − | 16 kDa | − |
| A107.1.1 | | 54 kDa | + | none | | | | | |
| | | 38 kDa | +/− | | | | | | |
| | | 16 kDa | +/− | | | | | | |

TABLE 12

Pro115 D-series MAb Western Blot Results.

| MAb | Cell line | | | |
|---|---|---|---|---|
| | LNCaP | | HCT116 | |
| | Bands detected | Intensity | Bands detected | Intensity |
| D2.1 | 54 kDa | + | none | |
| | 38 kDa | +/− | | |
| | 28 kDa | + | | |
| D3.1 | 54 kDa | +/− | none | |
| | 28 kDa | +/− | | |
| D5.1 | 54 kDa | + | none | |
| | 28 kDa | + | | |

Due to proteolytic cleavage of Pro115 three distinct bands are observed. The 54 kDa band represents the full length protein, the 38 kDa band represents the N-terminal product of the cleaved protein which has the LDL and SRCR domains, and the 28 kDa band represents the C-terminal product of the cleaved protein which has the protease domain. The antibodies A1.1, A4.1, A5.1, A8.1, A12.1, A107.1, D2.1, D3.1, and D5.1 specifically recognized Pro115 in western blots. Antibodies A1.1, A5.1, A8.1, A12.1, and A107.1 recognize full-length Pro115 and the N-terminal LDL/SRCR domain. Antibodies A4.1, D2.1, D3.1, and D5.1 recognize full-length Pro115 and the C-terminal protease domain. Some Pro115 antibodies including those from the B-series, F2 and F3 did not bind to Pro115 in western blot experiments, but did bind Pro115 in surface staining ELISAs above indicating these antibodies bind to a non-linear or conformational epitope destroyed in the denaturation of the western blot experiment.

Western Blots of Human Tissue

Western blots were conducted as described above using diseased and normal human tissues. Prostate and colon adenocarcinoma (ACA) tissues samples were evaluated alongside normal (NRM) prostate and colon tissues. Results of these experiments with anti-Pro115 MAb A4.1 are summarized in Tables 13 below. Band intensity is categorized as weak (−), intermediate (+/−), strong (+), or not detected (ND). The size of the band(s) detected is also indicated.

TABLE 13

Western Blot of Pro115 in human cancer tissues
Primary Human Tissue Samples

| Pro ACA #1 | | Pro ACA #2 | | Pro NRM | | CIn ACA | | CIn NRM | |
|---|---|---|---|---|---|---|---|---|---|
| Bands detected | Intensity | Bands detected | Intensity | Bands detected | Intensity | Bands detected | Intensity | Bands detected | Intensity |
| 54 kDa | +/− | 54 kDa | +/− | 54 kDa | − | 54 kDa | ND | 54 kDa | ND |
| 28 kDa | + | 28 kDa | + | 28 kDa | + | 28 kDa | +/− | 28 kDa | +/− |

These results demonstrate that Pro115 is expressed in higher levels in prostate and colon tumors than in normal prostate and colon tissue.

Example 2

Epitope Mapping of Pro115

Pro115 MAb Peptide Mapping

The epitopes recognized by antibodies from the Pro115 A, B, D and F series were determined by screening overlapping peptides for reactivity with the antibodies through an ELISA-based assay. Thirty-nine overlapping peptides were ordered from SynPep (Dublin, Calif.). Peptides 1-38 were 15-mers overlapping 5 amino acids with the adjacent peptides. Peptide 39 contained 7 amino acids. The peptide sequences started at amino acid W106 after the transmembrane domain and ended at G429 at the C-terminus of the Pro115 protein. These peptides span the extracellular region of the mature Pro115 protein. The peptides were provided in solution with a range of 1-3 mg/ml DMSO. A 1:400 dilution was made in PBS of each peptide and 50 µl were added to each well in duplicate on 96-well 4× Costar plates (#3690) (Costar Corporation; Cambridge, Mass.) and left overnight. Pro115 Construct 2 described above was used as a positive control on each 96-well plate. The next day, the plates were flicked dry and blocked with TBST 0.5% BSA for approximately 1 hour. Anti-Pro115 antibodies (50 µl) were added at 20 µg/ml per well and incubated at room temperature for approximately 2 hours. The plates were washed 3 times with TBST wash buffer. The secondary conjugate, goat anti-mouse Ig Fc-AP, (Pierce, Rockford, Ill.) was diluted 1:5000 in a TBST/BSA solution and 50 µl was added to each well. The plates were shaken for 2 hours at room temperature. The plates were washed 3 times before 50 µl of substrate was added to each well and incubated for 15 minutes at room temperature. The substrate used was pNPP in 1×DEA (1 mg/ml). To visualize the assay, plates were read at 405 nm on a SpectraMaxPlus plate reader (Molecular Devices, Sunnyvale, Calif.).

Table 14 below outlines the results of the anti-Pro115 antibody peptide binding experiments described above. Anti-Pro115 A and D series antibodies showed strong specific reactivity with Pro115 peptides. MAbs A1.1, A5.1, A8.1, A17.1, and A107.1 bound to peptides which cover the LDL receptor class A domain (C113-C148; peptides 1, 2, 3, 4 and 5). Anti-Pro115 antibodies which bind to the LDL receptor domain of Pro115 inhibit function of the LDL receptor domain. MAb A12.1 bound to peptide 12, which is in the SRCR domain (V149-N241; peptides 5, 6, 7, 8, 9, 10, 11, 12, 13, 14 and 15). Anti-Pro115 antibodies which bind to the SRCR domain of Pro115 inhibit function of the SRCR domain. MAbs A17.1, A24.1, A102.1, A107.1, D3.1, D5.1, D7.1 and D12.1 bound to peptides which are part of the protease domain (I256-Q487; peptides 23, 24, 25, 26, 27, 28, 29, 30, 31, 32, 33, 34, 35, 36, 37, 38 and 39). Anti-Pro115 antibodies which bind to the protease domain of Pro115 inhibit function of the protease domain. MAb A24.1, bound to peptide 34, which contains amino acid Ser441, the catalytic center of the protease domain. Anti-Pro115 antibodies which bind to peptides or epitopes containing amino acids which are part of the serine protease catalytic triad (His296, Asp345 or Ser441) inhibit protease activity of Pro115.

The following antibodies did not map to any peptide: A4.1, A25.1, A123.1, B3.1, B7.1, B20.1, B23.1, B29.1, B31.1, B34.1, D9.1, D10.1, D11.1, F2.1, F3.11.1. Since these antibodies bind to recombinant Pro115 in an ELISA assay, they recognize either a conformational epitope or a region that includes a post-translational modification. Despite not recognizing a linear epitope of the peptides evaluated, these antibodies have utility in binding Pro115 domains or inhibiting Pro115 biochemical and biological functions.

Anti-Pro115 antibodies which inhibit the function or activity of Pro115 domains inhibit or reduce Pro115 biochemical functions such as LDL receptor binding, scavenger receptor (SRCR domain) binding, protease activity or protease autocleavage and activation.

TABLE 14

Peptide mapping of Abs. Abs which generated an absorbance of 0.4 or higher in an ELISA assay are shown. Absorbance of irrelevant control antibodies was 0.1 OD.

| Peptide Number | Peptide Sequence | SEQ ID NO | Strong Binding OD > 1.0 | Moderate Binding 1.0 > OD > 0.4 |
|---|---|---|---|---|
| 1 | WKFMGSKCSNSGIEC | 9 | A8.1 | |
| 2 | SGIECDSSGTCINPS | 10 | A5.1, A8.1, A107.1 | A1.1, A22.1 |
| 3 | CINPSNWCDGVSHCP | 11 | A17.1 | A22.1 |
| 4 | VSHCPGGEDENRCVR | 12 | A17.1 | A22.1 |
| 5 | NRCVRLYGPNFILQM | 13 | | A22.1 |
| 6 | FILQMYSSQRKSWHP | 14 | | A22.1 |
| 7 | KSWHPVCQDDWNENY | 15 | A22.1 | |
| 8 | WNENYGRAACRDMGY | 16 | | A22.1 |
| 9 | RDMGYKNNFYSSQGI | 17 | A12.1 | A22.1 |
| 10 | SSQGIVDDSGSTSFM | 18 | | |
| 11 | STSFMKLNTSAGNVD | 19 | | |
| 12 | AGNVDIYKKLYHSDA | 20 | | |
| 13 | YHSDACSSKAVVSLR | 21 | | |
| 14 | VVSLRCIACGVNLNS | 22 | | |
| 15 | VNLNSSRQSRIVGGE | 23 | | D3.1 |
| 16 | IVGGESALPGAWPWQ | 24 | | A22.1 |
| 17 | AWPWQVSLHVQNVHV | 25 | | |
| 18 | QNVHVCGGSIITPEW | 26 | | A22.1 |
| 19 | ITPEWIVTAAHCVEK | 27 | | |
| 20 | HCVEKPLNNPWHWTA | 28 | | |
| 21 | WHWTAFAGILRQSFM | 29 | | |
| 22 | RQSFMFYGAGYQVEK | 30 | | |
| 23 | YQVEKVISHPNYDSK | 31 | D3.1 | |
| 24 | NYDSKTKNNDIALMK | 32 | | A22.1 |
| 25 | IALMKLQKPLTFNDL | 33 | A102.1, D5.1 | |
| 26 | IALMKLQKPLTFNDL | 34 | | |
| 27 | LPNPGMMLQPEQLCW | 35 | D12.1 | A22.1 |
| 28 | EQLCWISGWGATEEK | 36 | | A22.1 |
| 29 | ATEEKGKTSEVLNAA | 37 | | A22.1 |
| 30 | VLNAAKVLLIETQRC | 38 | A107.1 | A22.1, D2.1 |
| 31 | ETQRCNSRYVYDNLI | 39 | D3.1, D7.1 | A22.1 |
| 32 | YDNLITPAMICAGFL | 40 | | |
| 33 | CAGFLQGNVDSCQGD | 41 | A17.1 | A22.1 |
| 34 | SCQGDSGGPLVTSKN | 42 | A24.1 | |
| 35 | VTSKNNIWWLIGDTS | 43 | A22.1 | A8.1, B53.1 |
| 36 | IGDTSWGSGCAKAYR | 44 | | |
| 37 | AKAYRPGVYGNVMVF | 45 | A22.1 | A8.1 |
| 38 | NVMVFTDWIYRQMRA | 46 | | |
| 39 | RQMRADG | 47 | D3.1 | |

Pro115 and TMPRSS Family Sequence Alignment

FIG. 1 is an alignment of human Pro115 with other members of the TMPRSS family and with mouse Pro115. The Refseq accession numbers are: NP_005647.2 (TMPRSS2, human Pro115), NP_056590.2 (mouse TMPRSS2, mouse Pro115), NP_002142.1 (TMPRSS1), NP_076927.1 (TMPRSS3), NP_063947.1 (TMPRSS4), NP_110397.1 (TMPRSS5), NP_705837.1 (TMPRSS6), XP_293599.6 (TMPRSS7), NP_892018.1 (TMPRSS9), NP_006578.2 (TMPRSS10), NP_872365.1 (TMPRSS12), NP_114435.1 (TMPRSS13), the disclosures of which are herein incorporated by reference. The alignment was performed using the publicly available ClustalW 1.83 software using the default setting. Identical amino acids in a given position among the aligned proteins are marked with "*", conserved substitutions are marked with ":" and semi-conserved substitutions are marked with ".". The LDL receptor class A domain is underlined by two solid lines ( ══ ) the scavenger receptor cysteine-rich domain is underlined with a broken line ( ▬ ▬ ▬ ▬ ) the serine protease domain is underlined by a single solid line ( ▬▬▬▬ ) The three amino acids comprising the catalytic center are highlighted by a dark background.

Because mouse Pro115 would not be immunogenic in mice, differences between human Pro115 and mouse Pro115 are likely responsible for the immune response in mice immunized with Pro115 polypeptides and generation of the anti-Pro115 antibodies described herein. The overlapping peptides analyzed in conjunction with the cross species Pro115 alignment allowed us to determine with greater accuracy the epitopes and specific residues recognized by anti-Pro115 antibodies. The alignment of human Pro115 with mouse Pro115 and other human members of the TMPRSS family demonstrate immunogenic regions of Pro115 and specific epitopes and residues that antibodies which are specific for Pro115 bind to.

Pro115 MAb Epitope Mapping

Antibody A8.1 was strongly reactive with peptides 1 and 2, indicating that the common amino acid sequence SGIEC is recognized by this antibody. Since this sequence and residues I118 and E119 are specific to Pro115 among the human TMPRSS family members, A8.1 recognizes this epitope or specific residues within it. Antibody A17.1 was strongly reactive with peptides 3, 4 which share the common amino acid sequence VSHCP (SEQ ID NO:48). A17.1 was also reactive to peptide 33 which contains the epitope VDSCQ (SEQ ID NO:49) which has some homology to VSHCP (SEQ ID NO:48). Additionally, residue N433 is unique to Pro115 among the TMPRSS family members. Since sequences VDSCQ (SEQ ID NO:49) and VSHCP (SEQ ID NO:48) share homology and residues H138 and N433 are specific to Pro115 among the human TMPRSS family members, A17.1 recognizes these epitopes or specific residues within them.

Antibody A12.1 was strongly reactive with peptide 9. An amino acid change in peptide 9 between the human and mouse sequences occurs at position 186 where arginine (R) is replaced by lysine (K) (RDMG (SEQ ID NO:50) to KDMG (SEQ ID NO:51)). Additionally, residues D187, K191, N192, N193, F194, Y195 and Q198 are unique to Pro115 among the TMPRSS family members. Since this sequence and residues are specific to Pro115 among the human TMPRSS family members, A12.1 recognizes this epitope or specific residues within it.

Antibody A5.1 was strongly reactive with peptide 2, but not overlapping adjacent peptides 1 and 3, indicating that an amino acid sequence unique to peptide 2 is recognized by this antibody. An amino acid change in this sequence between the human and mouse sequences occurs at position 121 where aspartic acid (D) is replaced by glutamine (G) (DSSG (SEQ ID NO:52) to GSSG (SEQ ID NO:53)). Since this sequence and residues D121 and T125 are specific to Pro115 among the human TMPRSS family members, A5.1 recognizes this epitope or specific residues within it.

Antibody D3.1 was strongly reactive with peptides 23, 31, and 39, and has lower reactivity towards peptide 15, but was not reactive to overlapping adjacent peptides. Amino acid changes in these peptides between the human and mouse sequences occur at positions 247, 248, 250, 251 326, 413, 415, 417, 491 and 492. D3.1 may recognize an epitope generated by sequence YQVE (SEQ ID NO:54), NYDSK (SEQ ID NO:55), VYDNL (SEQ ID NO:56) or NLNSS (SEQ ID NO:57). Since these sequences and residues are specific to Pro115 among the human TMPRSS family members, D3.1 recognizes these epitopes or specific residues within them.

Antibodies A102.1 and D5.1 were strongly reactive with peptide 25 but not overlapping adjacent peptides 24 and 26, indicating that an amino acid sequence unique to peptide 25 is recognized by this antibody. There are 2 amino acid changes in peptide 25 between the human and mouse sequences. Positions 353 and 356 are changed from lysine (K) and threonine (T) to threonine (T) and alanine (A), respectively (KPLT (SEQ ID NO:58) to TPLA (SEQ ID NO:59)). Since this sequence is specific to Pro115 among the human TMPRSS family members, A102.1 and D5.1 recognizes this epitope or specific residues within it.

Antibody D7.1 was strongly reactive with peptide 31 but not overlapping adjacent peptides 30 and 32, indicating that an amino acid sequence unique to peptide 31 is recognized by this antibody. There are 3 amino acid changes in peptide 31 between the human and mouse sequences. Positions 415, 417 and 419 are changed from arginine (R), valine (V) and aspartic acid (D) to lysine (K), isoleucine (I) and aspartagine (N), respectively (RYVYD (SEQ ID NO:60) to KYIYN (SEQ ID NO:61)). Therefore, A5.1 recognizes this epitope or specific residues within it.

Antibody D12.1 was strongly reactive with peptide 27 but not overlapping adjacent peptides 26 and 28, indicating that an amino acid sequence unique to peptide 27 is recognized by this antibody. In peptide 27, the sequence QPEQL (SEQ ID NO:62)(human Pro115) is changed to DLDQE (SEQ ID NO:63) (mouse Pro115). Additionally, residues M371, M372, Q374, E376, Q377 and L378 are unique to Pro115 among the TMPRSS family members. Since this sequence and residues M371, M372, Q374, E376, Q377 and L378 are specific to Pro115 among the human TMPRSS family members, D12.1 recognizes this epitope or specific residues within it.

Antibody A24.1 is strongly reactive with peptide 34 but not overlapping adjacent peptides 33 and 35, indicating that an amino acid sequence unique to peptide 34 is recognized by this antibody. An amino acid change in peptide 34 between the human and mouse sequences occurs at position 448 where serine (S) is replaced by leucine (L) (VTSK (SEQ ID NO:64) to VTLK (SEQ ID NO:65)). Additionally, residues T447 and S448 are unique to Pro115 among the TMPRSS family members. Since this sequence and residues M371, M372, Q374, E376, Q377 and L378 are specific to Pro115 among the human TMPRSS family members, A24.1 recognizes this epitope or specific residues within it. Peptide 34 also contains residue S441 which is part of the catalytic triad. Antibodies which bind to peptide 19, peptide 24 or peptide 34 which respectively contain residues H296, D345 and S441 of the catalytic triad are capable of acting as agonists or antagonists to modulate the enzymatic activity of Pro115.

Antibodies which bind the same epitope of Pro115 as the antibodies of the present invention or compete for binding of the epitope of Pro115 bound by the antibodies of present invention are specific to Pro115. In addition, anti-Pro115 antibodies which bind to a linear or conformational epitope containing one or more of residues W106, M109, S111, N115, I118, E119, D121, T125, N131, W132, H138, G141, N146, Y152, P154, I157, M160, Q164, R165, K166, H169, Q173, N179, R182, A183, D187, K191, N192, N193, F194, Y195, Q198, D202, G205, S206, T207, M210, K211, L212, N213, T214, A216, G217, N218, V219, D220, I221, Y222, D229, A230, S232, K234, A235, I242, V246, N247, N249, R252, Q253, N277, P301, N303, W306, H307, L315, R316, F319, M320, F321, Y322, Y326, Q327, D338, N343, K362, M371, M372, Q374, E376, Q377, L378, K390, E395, A399, K401, L403, E406, L419, A423, N433, T447, S448, I452, W454, I456, D458, K467, Y469, R470, G475, M478, V479, T481, R486, R489, G492 of the Pro115 protein are specific to Pro115. Residues N128, N213 and N249 are N-glycosylation sites on Pro115 and are unique to Pro115 among the TMPRSS family members.

Example 3

Pro115 Cell Surface Expression in LNCaP Cells

LNCaP cells were stimulated for 48 hours by adding Mibolerone (10 nM final concentration) to the culture medium. Cells were either directly harvested for the determination of the total cellular Pro115 expression or the cell surface proteins were biotinylated prior to the harvest for the determination of the cell surface expression of Pro115.

To determine the total cellular Pro115 expression in stimulated and unstimulated LNCaP cells, cells were incubated for 10 min in Cell Lysis Buffer (50 mM Tris, pH7.5, 50 mM NaCl, 2 mM EDTA, 1% NP-40; complete protease inhibitors (Roche) were added freshly). The lysate was centrifuged for 10 min at 4° C. at 10,000 g then the protein concentration of the cleared supernatant was determined (BCA Assay, #23227; Pierce). Fifteen ug total proteins were separated by electrophoresis on NuPAGE 4-12% Bis-Tris gels (Invitrogen) under denaturing conditions in Novex-XCell II Minicell gel apparatus (Invitrogen) and subsequently transferred to PVDF membranes using an XCell II Blot Module (Invitrogen Life Technologies). Following the transfer of proteins, the membranes were blocked in TBST with 5% non fat milk at room temperature for at least an hour, followed by incubation overnight at 4° C. with purified primary MAb Pro115.A12.1 at a concentration of 2 ug/mL, and then with horseradish-peroxidase conjugated goat anti-mouse IgG secondary antibody (Jackson Immunoresearch Laboratories, Inc.) and finally visualized by chemiluminescence using an ECL advance western blotting detection kit (Amersham Biosiences, Piscataway, N.J.).

To determine the Pro115 cell surface expression level, stimulated and unstimulated LNCaP cells from one well of a 6 well plate were washed with ice-cold PBS with 1 mM CaCl$_2$ and 0.5 mM MgCl$_2$ (PBS/MgCa) and incubated in 1 mL ice-cold Sulfo-SS-Biotin (0.5 mg/mL in PBS/MgCa; #21331; Pierce) for 30 min at 4° C. on ice. Cells were washed once with ice cold PBS/25 mM Tris and twice with ice-cold PBS/MgCa and incubated in 0.2 mL Cell Lysis Buffer for 10 min on ice. Seventy-five ug total proteins were incubated with 100 ul Streptavidin-Agarose (#20349, Pierce) for 2 hours at 4° C. The agarose beads were washed three times in Cell Lysis Buffer and retained proteins were eluted from the beads by incubation in 1× NuPage Sample Buffer supplemented with reducing agent (Invitrogen). The eluted proteins were separated by gel electrophoresis and analyzed by western blotting as described above.

Table 15 summarizes the intensities of the bands at 54 kDa (full length Pro115) and 38 kDa (N-terminal LDL/SRCR domain) observed in the western blot experiment. Band intensity is categorized as weak (−), intermediate (+/−), strong (+), or not detected (ND). The size of the band(s) detected is also indicated. The results show that both, total cellular expression and cell surface expression of Pro115, are upregulated in LNCaP cells upon stimulation with mibolerone. The results further demonstrate that the majority of cell surface Pro115 in stimulated LNCaP cells is in its active (cleaved) conformation.

TABLE 15

Total cellular expression and cell surface expression of Pro115 in stimulated and unstimulated LNCaP cells

| Primary MAb | Sample loaded on gel | Unstimulated LNCaP | | Stimulated LNCaP | |
|---|---|---|---|---|---|
| | | Bands detected | Intensity | Bands detected | Intensity |
| A12.1 | Whole cell lysate | 54 kDa | +/− | 54 kDa | + |
| | | 38 kDa | +/− | 38 kDa | + |
| A12.1 | Biotinylated cell surface protein eluted from streptavidin agarose | 54 kDa | − | 54 kDa | +/− |
| | | 38 kDa | − | 38 kDa | + |

Example 4

Immunohistochemical Staining of Human Tissues

To evaluate the expression pattern of Pro115 and the utility of Pro115 mAbs as staining and imaging agents several human tissues were evaluated. OCT embedded blocks of normal organ tissues were obtained from Zoion (Hawthorne, N.Y.). Sections were cut at −20° C. in a cryochamber at a thickness of 5-8 um, and air-dried for 30 minutes at room temperature. Immunohistochemical (IHC) staining was performed using the Immunovision Powervision Kit (Vision Biosystems Inc., Norwell, Mass.). Briefly, slides were rinsed in Tris-Buffered Saline with 0.5% Tween-20 (TBS-T) to remove OCT medium and incubated with a series of primary mAbs for 30 minutes at room temperature. Primary antibodies included 10 anti-Prof 15 mAbs (10 ug/ml), as well as mouse IgG (10 ug/ml) and anti-E-cadherin (BD Biosciences, 1:500 concentration) as negative and positive controls, respectively. The slides were then post-fixed in 4% paraformaldehyde fixative for 10 minutes at room temperature, and rinsed with TBS-T. Endogenous peroxidase activity was quenched by treating the slides with 3% hydrogen peroxide solution for 10 minutes. After washing in TBS-T, slides were incubated with anti-mouse IgG-horseradish peroxidase (HRP) secondary antibody (Vision Biosystems) for 30 minutes at room temperature in the dark. The slides were then washed again in TBS-T, and the sections were treated with 3,3'-diaminobenzidine chromagen for 2~5 minutes (Vision Biosystems). Finally, the slides were counterstained with hematoxylin before mounting with Supermount (Biogenex, San Ramon, Calif.). Staining was then observed using a Zeiss Axioskop 2 microscope, and relative staining intensity was scored. A summary of the staining is in Table 16 below.

TABLE 16

Pro115 expression in various human tissues

| mAb | Heart | Liver | Kidney | Stomach | Bladder | Testis | Colon | Ovary | Prostate | Pancreas | Lung |
|---|---|---|---|---|---|---|---|---|---|---|---|
| B3.1 | − | ++ | tubing 2 + C | − | + | + | + | − | +++ | ++ | ++ |
| B7.1 | − | − | focal tubing 1 + C | − | − | − | + | − | +++ | + | +/− |
| B20.1 | − | − | tubing 1 + C | + | − | − | − | − | +++ | + | − |
| B23.1 | − | − | − | − | − | − | + | − | +++ | − | − |
| B29.1 | − | − | tubing 1 + C | epi 1 + C | + | + | + | − | +++ | + | +/− |
| B31.1 | − | − | − | − | − | − | + | − | +++ | + | +/− |
| B34.1 | − | − | focal tubing 1 + C | − | − | +/− | + | − | +++ | − | − |
| B53.1 | − | − | − | − | − | − | +/− | − | +++ | + | − |

TABLE 16-continued

Pro115 expression in various human tissues

| mAb | Heart | Liver | Kidney | Stomach | Bladder | Testis | Colon | Ovary | Prostate | Pancreas | Lung |
|---|---|---|---|---|---|---|---|---|---|---|---|
| F2.1 | − | − | +/− | − | − | − | − | − | +++ | − | +/− |
| F3.11.1 | − | − | +/− | − | − | +/− | ++ | − | +++ | + | + |
| E-cadherin | − | +++ | +++ | +++ | +++ | − | +++ | − | +++ | +++ | +++ |
| IgG1 | − | − | − | − | − | − | − | − | − | − | − |

As shown in Table 16, all Pro115 MAbs demonstrated the ability to detect Pro115 in human tissues and are useful and staining or imaging agents. Pro115 staining was strongest in prostate tissue. With the exception of B3.1 all Pro115 MAbs exhibited minimal reactivity with the remainder of the organs in the panel, demonstrating the specificity of the mAbs to Pro115 and the restricted expression pattern of Pro115.

Example 5

Killing of Pro115 Expressing Cells

Generation of Stable Pro115-Overexpressing Cells

DU145 cells (ATCC, Manassas, Va.) were transfected with pLPCX retroviral vectors encoding either protease active full length Pro115 (Pro115-WT), protease inactive full length Pro115 (Pro115-SA, containing a mutation at amino acid residue 441 from serine to alanine), or a negative control plasmid encoding alkaline phosphatase (AP). Briefly, Phoenix-Ampho cells (Orbigen, San Diego, Calif.) were transfected with the appropriate vectors using Lipofectamine 2000 transfection reagent (Invitrogen, Carlsbad, Calif.), and incubated at 37° C. in 5% CO2 for 48 hours. Supernatants were then collected from the Phoenix-Ampho cells, filtered through 0.45 uM polysulfonic filters, and diluted 1:1 in DMEM supplemented with 10% fetal bovine serum. Polybrene (Hexadimethrine Bromide; Sigma) was then added to the viral supernatants at a final concentration of 8 ug/ml. The diluted viral supernatants were then added to adherent DU145 cells and incubated at 37° C., 5% $CO_2$ for 5 hours. Fresh medium was added, and the cells were incubated overnight. The medium was then completely aspirated and replaced with fresh DMEM+10% fetal bovine serum and the cells were incubated at 37° C., 5% $CO_2$ for 24 hours. Selection was initiated by adding puromycin (Clontech) to the culture medium at a final concentration of 0.6 ug/ml. Following selection and scale-up of the transfected cells, Pro115 overexpression was confirmed by Western immunoblot, live cell immunofluorescence, and FACS analysis.

Killing of Pro115 Expressing Cells

Experiments were performed by incubating DU145-Pro115 stable transfectants with Pro115 MAbs premixed with MAb-Zap goat anti-mouse Ig saporin conjugate (Advanced Targeting Systems, San Diego, Calif.). Cell viability was measured at day 5 to detect killing effects due to internalization of the Pro115 MAbs.

On the day before MAb treatment, DU145-AP, DU145-Pro115-SA, and DU145-Pro115-WT cells were seeded on 96 well flat bottom sterile cell culture plates (Corning), in triplicate wells, at 5000 cells/100 ul/well in DMEM medium with 10% FBS. Plates were incubated at 37° C. in 5% $CO_2$, overnight. The following day, 25 ul of Pro115 MAbs diluted in DMEM+10% FBS, with or without MAb-Zap reagent was added to the appropriate wells. Final MAb concentrations were 2.0 μg/mL and 0.4 μg/mL, and the final concentration of MAb-Zap reagent was 1 μg/mL. Plain medium with or without MAb-Zap reagent were included as controls. In addition, anti-transferrin receptor (TnfR) and anti-Ricin MAbs were included as positive and negative controls, respectively. Plates were shaken gently for five minutes to mix the reagents and then incubated at 37° C. in 5% $CO_2$. After 4 days, cell viability was determined using Cell Titer Glo reagent (Promega). Cell viability was expressed as a percentage of the control wells with medium alone, as shown in Table 17 below.

TABLE 17

Growth inhibition of Pro115 expressing cells

Percent Growth Inhibition Compared to Wells with Medium Alone

| | DU145-AP | | | DU145-Pro115-SA | | | DU145-Pro115-WT | | |
|---|---|---|---|---|---|---|---|---|---|
| | mAb alone | mAb + mAbZap | | mAb alone | mAb + mAbZap | | mAb alone | mAb + mAbZap | |
| Pro115 mAb | (2 ug/ml) | mAb (2 ug/ml) | mAb (0.4 ug/ml) | (2 ug/ml) | mAb (2 ug/ml) | mAb (0.4 ug/ml) | (2 ug/ml) | mAb (2 ug/ml) | mAb (0.4 ug/ml) |
| A107.1 | −4.5 | −5.4 | 1 | −0.5 | 5.3 | 4.5 | −3.7 | −3.7 | 2.7 |
| A123.1 | −0.8 | −1.1 | 3.6 | 2.7 | 7.3 | 11.3 | 1 | 1 | 0 |
| B3.1 | −0.4 | 21.5 | 10 | 10.3 | 38.5 | 24.5 | 4.5 | 18 | 7.6 |
| B7.1 | −2 | 7.7 | 1.8 | 4.6 | 20.6 | 23 | 2.2 | 8.5 | 8.5 |
| B20.1 | −1.1 | −3.5 | 0 | 0.5 | 12.5 | 19.4 | 0.5 | 0.6 | 7 |
| B23.1 | −1.5 | 4.4 | 6.9 | 9.2 | 20.3 | 21.6 | 3.4 | 7.4 | 5.7 |
| B29.1 | 5.1 | 11.3 | 4.5 | 6.7 | 19.4 | 20.5 | 5.5 | 6.3 | 8.7 |
| B31.1 | 3 | 7 | 2.7 | 3.8 | 17.9 | 9.9 | 4.6 | 6 | 7.3 |
| B34.1 | 0 | −2.3 | 2 | −4.4 | 9.5 | 11.9 | 0 | 4.5 | 5 |
| B53.1 | 2.4 | 4.1 | 4.9 | 2.7 | 12.2 | 18.2 | −2.6 | 1.2 | 6 |
| F2.1 | 3.9 | 17.6 | 11.4 | 10.3 | 12.6 | 13.6 | 0.5 | 16.2 | 14.4 |
| F3.11.1 | 8.6 | 15.5 | 10.4 | 11.1 | 42.5 | 48 | −1.2 | 26.7 | 16.8 |
| Ricin | 1.5 | 6 | 4.5 | 8.1 | 7.1 | 6.3 | 2 | 1.5 | 0 |
| TnfR | 2.7 | 73.2 | 81.4 | 8 | 74.1 | 81.8 | 3.5 | 67.7 | 76.2 |

Anti-transferrin receptor MAb resulted in significant cell killing across all three cell types while anti-Ricin MAb had a minimal effect on cell viability, as expected.

Pro115 mAbs B7.1, B20.1, B23.1, B29.1, B31.1, F2.1 and F3.11.1 exhibited significant cell killing in DU145-Pro115-SA and -Pro115-WT cells, but had a minimal killing effect on the DU145-AP cells, indicating Pro115-specific targeting. In general, cell killing was greater in the DU145-Pro115-SA cells than in the -Pro115-WT cells, which is likely due to higher expression levels of the Pro115-SA mutant as determined by FACS stain. Pro115 mAb F3.11.1 exhibited the highest level of cell killing of all the Pro115 MAbs, with nearly three times the cell killing effect on the Pro115-SA cells compared to the AP cells.

Example 6

Inhibition of Pro115 Protease Activity

Generation of Stable Pro115-Overexpressing Cells

A cell-based protease assay was utilized to screen Pro115 antibodies for inhibition of Pro115 activity. Briefly, DU145-Pro115-WT and DU145-Pro115-SA cells (described above) were seeded on 96-well black tissue culture plates at a density of 50,000 cells per well, and incubated overnight at 37° C. in 5% $CO_2$. The cells were then washed three times with serum-free DMEM, and Pro115 MAbs diluted in serum-free DMEM were added at final concentrations of 50, 10, and 2 ug/ml, in triplicates. Anti-Ricin MAb was added as a negative control MAb, and Serine Protease Inhibitor Cocktail #1 (EMD Biosciences, San Diego, Calif.) at final concentrations of 1×, 0.2×, and 0.04× was added as positive controls. The cells were incubated with the antibodies for 10 minutes at 37° C. Substrate Boc-QAR-AMC (Bachem) diluted in serum-free DMEM was then added to each well at a final concentration of 250 uM. The antibody and substrate solutions were also added to a plate without cells to provide a measurement of background signal. Plates were incubated at 37° C., 5% $CO_2$ in the dark for 2 hours. The plates were then read on a SpectraMAX Gemini EM spectrophotometer (Molecular Devices, Sunnyvale, Calif.) at 370 nm excitation, 450 nm emission, and 435 nm auto-cutoff.

Data generated from the Pro115 inactive DU145-Pro115-SA cells were used to determine the level of background protease activity in the assay. In general, the signal of DU145-Pro115-WT cells was approximately three times higher than that of the DU145-Pro115-SA cells, indicating that Pro115 activity can be specifically measured in the assay.

Data from the DU145-Pro115-WT wells were analyzed by determining the average signal from each set of triplicates. The background signal from the cell-free plates was then subtracted out, and the data was expressed as percent inhibition relative to the untreated DU145-Pro115-WT signal, as shown in Table 18 below.

TABLE 18

Inhibition of Pro115 protease activity by anti-Pro115 antibodies

| Pro115 Mab | % Protease Activity Inhibition Relative to DU145-Pro115-WT Untreated Control | | |
|---|---|---|---|
| | 50 ug/ml | 10 ug/ml | 2 ug/ml |
| B3.1 | 30.7 | 17.4 | 9 |
| B7.1 | 19.1 | 9.1 | −5.9 |

TABLE 18-continued

Inhibition of Pro115 protease activity by anti-Pro115 antibodies

| Pro115 Mab | % Protease Activity Inhibition Relative to DU145-Pro115-WT Untreated Control | | |
|---|---|---|---|
| | 50 ug/ml | 10 ug/ml | 2 ug/ml |
| B20.1 | 33 | 34.7 | 25.4 |
| B23.1 | 24 | 19.8 | 8.4 |
| B29.1 | 35.6 | 27.4 | 13.9 |
| B31.1 | 21.6 | 11.1 | 11.2 |
| B34.1 | 23.5 | 29.3 | 14.9 |
| F2.1 | 16.7 | 21.2 | 17.4 |
| F3.11.1 | 24.9 | 28.7 | 33.6 |
| anti-Ricin | 3.3 | N/D | N/D |
| Serine Protease Inhibitor Cocktail #1 | 1X | 0.2X | 0.04X |
| | 94.7 | 82.2 | 46.9 |

N/D: not determined

At 50 ug/ml, the Pro115 MAbs tested exhibited protease inhibition ranging from 16% to 35%. In addition, most MAbs exhibited a dose dependent effect, as the protease inhibition decreased with decreasing MAb concentration. As expected, the negative control anti-Ricin MAb had an insignificant effect on protease activity. The positive control Serine Protease Inhibitor Cocktail #1 had a profound effect on protease activity, reducing activity by nearly 95% at the highest concentration. However, this result is expected, as the reagent is a broad-spectrum inhibitor that affects many different serine proteases. For example, at 1×, the serine protease inhibitor cocktail showed a nearly 100% inhibition of protease activity in DU145-Pro115-SA cells, which express an inactive form of Pro115. Therefore, it is clear that the inhibitor has an effect on all background serine proteases as well.

Additionally, is noted that while anti-Pro115 mAbs F2.1 and F3.11.1 did not have a clear dose dependent effect on protease activity at the concentrations tested, they did demonstrate high levels of protease inhibition. A dose dependant response to these antibodies at lower concentrations indicates that less antibody is needed to inhibit protease activity and that such potent antibodies have utility as therapeutic agents.

Example 7

Deposits

Deposit of Cell Lines and DNA

The following hybridoma cell lines were deposited with the American Type Culture Collection (ATCC) located at 10801 University Boulevard, Manassas, Va. 20110-2209, U.S.A., and accorded accession numbers.

TABLE 19

ATCC deposits

| Hybridoma | ATCC Accession No. | Deposit Date |
|---|---|---|
| Pro115.B7.1 | PTA-7604 | 19 May 2006 |
| Pro115.B34.1 | PTA-7605 | 19 May 2006 |

Anti-Pro115 antibody hybridomas Pro115.B7.1 and Pro115.B34.1 were shipped to the ATCC via FedEx Overnight on 18 May 2006. A Patent Specialist at the ATCC Patent Depository confirmed receipt of the shipment in good condition via email on 19 May 2006.

The names of the deposited hybridoma cell lines above may be shortened for convenience of reference. E.g. B7.1 corresponds to Pro115.B7.1. These hybridomas correspond to the clones (with their full names) listed in Table 19.

These deposits were made under the provisions of the Budapest Treaty on the International Recognition of the Deposit of Microorganisms for the Purpose of Patent Procedure and the Regulations there under (Budapest Treaty). This assures maintenance of viable cultures for 30 years from the date of deposit. The organisms will be made available by ATCC under the terms of the Budapest Treaty, and subject to an agreement between diaDexus, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 3 7 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws. The making of these deposits is by no means an admission that deposits are required to enable the invention.

We claim:

1. An isolated monoclonal antibody which competes for binding to the same epitope as the epitope bound by the monoclonal antibody produced by a hybridoma selected from the group consisting of American Type Culture Collection accession number PTA-7604 and PTA-7605 or which is produced by a hybridoma selected from the group consisting of American Type Culture Collection accession number PTA-7604 and PTA-7605.

2. The antibody of claim 1 which is an antibody binding fragment, a chimeric antibody, a human antibody or humanized antibody.

3. The antibody of claim 2 which is conjugated to a growth inhibitory agent or a cytotoxic agent.

4. The antibody of claim 3 wherein the cytotoxic agent is selected from the group consisting of toxins, antibiotics, radioactive isotopes and nucleolytic enzymes.

5. The antibody of claim 4, wherein the toxin is selected from the group consisting of ricin, saponin, maytansinoid and calicheamicin.

6. The antibody of claim 3 where the antibody inhibits the growth of Pro115 (SEQ ID NO:66)-expressing cancer cells.

7. The antibody of claim 6, wherein the cancer cells are from a cancer selected from the group consisting of prostate, colon, lung and pancreas cancer.

8. An isolated cell that produces the antibody of claim 1.

9. The cell of claim 8, wherein the cell is a hybridoma selected from the group consisting of American Type Culture Collection accession number PTA-7604 and PTA-7605.

10. A composition comprising the antibody of claim 1 and a carrier.

11. The composition of claim 10, wherein the antibody is an antibody binding fragment, a chimeric antibody, a human antibody or humanized antibody.

12. The composition of claim 11, wherein the humanized antibody is a humanized form of an anti-Pro115 antibody produced by hybridoma selected from the group consisting of American Type Culture Collection accession number PTA-7604 and PTA-7605.

13. An article of manufacture comprising a container and a composition contained therein, wherein the composition comprises an antibody of claim 1.

14. A kit comprising the antibody of claim 1.

15. The kit of claim 14, wherein the antibody is an antibody binding fragment, a chimeric antibody, a human antibody or humanized antibody.

16. The kit of claim 14, wherein the antibody is a monoclonal antibody produced by hybridoma selected from the group consisting of American Type Culture Collection accession number PTA-7604 and PTA-7605.

17. The kit of claim 14 wherein such antibody is labeled.

18. The kit of claim 14 further comprising a label or package insert.

* * * * *

SEQUENCE LISTING

```
<160> NUMBER OF SEQ ID NOS: 77

<210> SEQ ID NO 1
<211> LENGTH: 504
<212> TYPE: PRT
<213> ORGANISM: ARTIFICIAL SEQUENCE
<220> FEATURE:
<223> OTHER INFORMATION: Synthetic

<400> SEQUENCE: 1

Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45

Val Pro Gln Tyr Ala Pro Arg Val Leu Thr Gln Ala Ser Asn Pro Val
    50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
        115                 120                 125

Pro Ser Asn Trp Cys Asp Gly Val Ser His Cys Pro Gly Gly Glu Asp
    130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240
```

```
Cys Ile Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
        275                 280                 285

Glu Trp Ile Val Thr Ala Ala His Cys Val Glu Lys Pro Leu Asn Asn
    290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
        355                 360                 365

Pro Gly Met Met Leu Gln Pro Glu Gln Leu Cys Trp Ile Ser Gly Trp
    370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
            420                 425                 430

Asn Val Asp Ser Cys Gln Gly Asp Ser Gly Gly Pro Leu Val Thr Ser
        435                 440                 445

Lys Asn Asn Ile Trp Trp Leu Ile Gly Asp Thr Ser Trp Gly Ser Gly
    450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Arg Ala Asp Gly Ala Ser His His
                485                 490                 495

His His His His His His
            500

<210> SEQ ID NO 2
<211> LENGTH: 414
<212> TYPE: PRT
<213> ORGANISM: ARTIFICIAL SEQUENCE
<220> FEATURE:
<223> OTHER INFORMATION: Synthetic

<400> SEQUENCE: 2

Met Leu Gln Asn Ser Ala Val Leu Leu Val Leu Val Ile Ser Ala Ser
1               5                   10                  15

Ala Asp Ile Gly Ser Lys Cys Ser Asn Ser Gly Ile Glu Cys Asp Ser
            20                  25                  30

Ser Gly Thr Cys Ile Asn Pro Ser Asn Trp Cys Asp Gly Val Ser His
        35                  40                  45

Cys Pro Gly Gly Glu Asp Glu Asn Arg Cys Val Arg Leu Tyr Gly Pro
    50                  55                  60

Asn Phe Ile Leu Gln Val Tyr Ser Ser Gln Arg Lys Ser Trp His Pro
65                  70                  75                  80

Val Cys Gln Asp Asp Trp Asn Glu Asn Tyr Gly Arg Ala Ala Cys Arg
                85                  90                  95

Asp Met Gly Tyr Lys Asn Asn Phe Tyr Ser Ser Gln Gly Ile Val Asp
```

```
            100                 105                 110
Asp Ser Gly Ser Thr Ser Phe Met Lys Leu Asn Thr Ser Ala Gly Asn
            115                 120                 125

Val Asp Ile Tyr Lys Lys Leu Tyr His Ser Asp Ala Cys Ser Ser Lys
            130                 135                 140

Ala Val Val Ser Leu Arg Cys Ile Ala Cys Gly Val Asn Leu Asn Ser
145                 150                 155                 160

Ser Arg Gln Ser Arg Ile Val Gly Gly Glu Ser Ala Leu Pro Gly Ala
                    165                 170                 175

Trp Pro Trp Gln Val Ser Leu His Val Gln Asn Val His Val Cys Gly
                180                 185                 190

Gly Ser Ile Ile Thr Pro Glu Trp Ile Val Thr Ala Ala His Cys Val
                195                 200                 205

Glu Lys Pro Leu Asn Asn Pro Trp His Trp Thr Ala Phe Ala Gly Ile
            210                 215                 220

Leu Arg Gln Ser Phe Met Phe Tyr Gly Ala Gly Tyr Gln Val Glu Lys
225                 230                 235                 240

Val Ile Ser His Pro Asn Tyr Asp Ser Lys Thr Lys Asn Asn Asp Ile
                    245                 250                 255

Ala Leu Met Lys Leu Gln Lys Pro Leu Thr Phe Asn Asp Leu Val Lys
                260                 265                 270

Pro Val Cys Leu Pro Asn Pro Gly Met Met Leu Gln Pro Glu Gln Leu
                275                 280                 285

Cys Trp Ile Ser Gly Trp Gly Ala Thr Glu Glu Lys Gly Lys Thr Ser
            290                 295                 300

Glu Val Leu Asn Ala Ala Lys Val Leu Leu Ile Glu Thr Gln Arg Cys
305                 310                 315                 320

Asn Ser Arg Tyr Val Tyr Asp Asn Leu Ile Thr Pro Ala Met Ile Cys
                    325                 330                 335

Ala Gly Phe Leu Gln Gly Asn Val Asp Ser Cys Gln Gly Asp Ala Gly
                340                 345                 350

Gly Pro Leu Val Thr Ser Lys Asn Asn Ile Trp Trp Leu Ile Gly Asp
                355                 360                 365

Thr Ser Trp Gly Ser Gly Cys Ala Lys Ala Tyr Arg Pro Gly Val Tyr
            370                 375                 380

Gly Asn Val Met Val Phe Thr Asp Trp Ile Tyr Arg Gln Met Arg Ala
385                 390                 395                 400

Asp Gly Ala Ser His His His His His His His His His
                    405                 410

<210> SEQ ID NO 3
<211> LENGTH: 268
<212> TYPE: PRT
<213> ORGANISM: ARTIFICIAL SEQUENCE
<220> FEATURE:
<223> OTHER INFORMATION: Synthetic

<400> SEQUENCE: 3

Met Leu Gln Asn Ser Ala Val Leu Leu Val Leu Val Ile Ser Ala Ser
1               5                   10                  15

Ala Asp Ile Ile Val Gly Gly Glu Ser Ala Leu Pro Gly Ala Trp Pro
            20                  25                  30

Trp Gln Val Ser Leu His Val Gln Asn Val His Val Cys Gly Gly Ser
        35                  40                  45

Ile Ile Thr Pro Glu Trp Ile Val Thr Ala Ala His Cys Val Glu Lys
    50                  55                  60
```

```
Pro Leu Asn Asn Pro Trp His Trp Thr Ala Phe Ala Gly Ile Leu Arg
 65                  70                  75                  80

Gln Ser Phe Met Phe Tyr Gly Ala Gly Tyr Gln Val Glu Lys Val Ile
                 85                  90                  95

Ser His Pro Asn Tyr Asp Ser Lys Thr Lys Asn Asn Asp Ile Ala Leu
            100                 105                 110

Met Lys Leu Gln Lys Pro Leu Thr Phe Asn Asp Leu Val Lys Pro Val
        115                 120                 125

Cys Leu Pro Asn Pro Gly Met Met Leu Gln Pro Glu Gln Leu Cys Trp
130                 135                 140

Ile Ser Gly Trp Gly Ala Thr Glu Glu Lys Gly Lys Thr Ser Glu Val
145                 150                 155                 160

Leu Asn Ala Ala Lys Val Leu Leu Ile Glu Thr Gln Arg Cys Asn Ser
                165                 170                 175

Arg Tyr Val Tyr Asp Asn Leu Ile Thr Pro Ala Met Ile Cys Ala Gly
            180                 185                 190

Phe Leu Gln Gly Asn Val Asp Ser Cys Gln Gly Asp Ser Gly Gly Pro
        195                 200                 205

Leu Val Thr Ser Lys Asn Asn Ile Trp Trp Leu Ile Gly Asp Thr Ser
210                 215                 220

Trp Gly Ser Gly Cys Ala Lys Ala Tyr Arg Pro Gly Val Tyr Gly Asn
225                 230                 235                 240

Val Met Val Phe Thr Asp Trp Ile Tyr Arg Gln Met Arg Ala Asp Gly
                245                 250                 255

Ala Ser His His His His His His His His His
            260                 265

<210> SEQ ID NO 4
<211> LENGTH: 177
<212> TYPE: PRT
<213> ORGANISM: ARTIFICIAL SEQUENCE
<220> FEATURE:
<223> OTHER INFORMATION: Synthetic

<400> SEQUENCE: 4

Met Leu Gln Asn Ser Ala Val Leu Leu Val Leu Val Ile Ser Ala Ser
 1               5                  10                  15

Ala Asp Ile His His His His His His His His Gly Ser Lys
                20                  25                  30

Cys Ser Asn Ser Gly Ile Glu Cys Asp Ser Ser Gly Thr Cys Ile Asn
            35                  40                  45

Pro Ser Asn Trp Cys Asp Gly Val Ser His Cys Pro Gly Gly Glu Asp
 50                  55                  60

Glu Asn Arg Cys Gly Glu Ser Ala Leu Thr Leu Gly Arg Asp Ser Ser
 65                  70                  75                  80

Ala His Leu Gly Asp Ser Ser Arg Val Gln Gly Pro Leu Gly Asp Trp
                 85                  90                  95

Ala Trp Arg Ala Ser Ser Thr Leu Thr His Asp Val Ile Glu Ser Leu
            100                 105                 110

Leu Gln Ala Glu Pro Trp Gly Ser Glu Arg Leu Cys Phe Arg Pro Asn
        115                 120                 125

Leu Thr Gln Gln Val Gly Asp Asp Arg Ala Thr Glu Asp Cys Val Ile
130                 135                 140

Gly Thr Thr Arg Ala Leu Asn Cys His Arg Lys Ser Val Lys Met Ser
145                 150                 155                 160
```

Lys Leu Phe Ile Lys Leu Glu Met Gln Ala Arg Asn Gly Gly Ser Cys
            165                 170                 175

Leu

<210> SEQ ID NO 5
<211> LENGTH: 315
<212> TYPE: PRT
<213> ORGANISM: ARTIFICIAL SEQUENCE
<220> FEATURE:
<223> OTHER INFORMATION: Synthetic

<400> SEQUENCE: 5

Met Leu Gln Asn Ser Ala Val Leu Leu Val Leu Val Ile Ser Ala Ser
1               5                   10                  15

Ala Thr His Glu Ala Glu Gln Ser Arg Lys Pro Glu Ser Gln Glu Ala
            20                  25                  30

Ala Pro Leu Ser Gly Pro Cys Gly Arg Arg Val Ile Thr Ser Arg Ile
        35                  40                  45

Val Gly Gly Glu Asp Ala Glu Leu Gly Arg Trp Pro Trp Gln Gly Ser
    50                  55                  60

Leu Arg Leu Trp Asp Ser His Val Cys Gly Val Ser Leu Leu Ser His
65                  70                  75                  80

Arg Trp Ala Leu Thr Ala Ala His Cys Phe Glu Thr Tyr Ser Asp Leu
                85                  90                  95

Ser Asp Pro Ser Gly Trp Met Val Gln Phe Gly Gln Leu Thr Ser Met
            100                 105                 110

Pro Ser Phe Trp Ser Leu Gln Ala Tyr Tyr Thr Arg Tyr Phe Val Ser
        115                 120                 125

Asn Ile Tyr Leu Ser Pro Arg Tyr Leu Gly Asn Ser Pro Tyr Asp Ile
130                 135                 140

Ala Leu Val Lys Leu Ser Ala Pro Val Thr Tyr Thr Lys His Ile Gln
145                 150                 155                 160

Pro Ile Cys Leu Gln Ala Ser Thr Phe Glu Phe Glu Asn Arg Thr Asp
                165                 170                 175

Cys Trp Val Thr Gly Trp Gly Tyr Ile Lys Glu Asp Glu Ala Leu Pro
            180                 185                 190

Ser Pro His Thr Leu Gln Glu Val Gln Val Ala Ile Ile Asn Asn Ser
        195                 200                 205

Met Cys Asn His Leu Phe Leu Lys Tyr Ser Phe Arg Lys Asp Ile Phe
210                 215                 220

Gly Asp Met Val Cys Ala Gly Asn Ala Gln Gly Gly Lys Asp Ala Cys
225                 230                 235                 240

Phe Gly Asp Ser Gly Gly Pro Leu Ala Cys Asn Lys Asn Gly Leu Trp
                245                 250                 255

Tyr Gln Ile Gly Val Val Ser Trp Gly Val Gly Cys Gly Arg Pro Asn
            260                 265                 270

Arg Pro Gly Val Tyr Thr Asn Ile Ser His His Phe Glu Trp Ile Gln
        275                 280                 285

Lys Leu Met Ala Gln Ser Gly Met Ser Gln Pro Asp Pro Ser Trp Ala
    290                 295                 300

Ser His His His His His His His His
305                 310                 315

<210> SEQ ID NO 6
<211> LENGTH: 171
<212> TYPE: PRT
<213> ORGANISM: ARTIFICIAL SEQUENCE

-continued

```
<220> FEATURE:
<223> OTHER INFORMATION: Synthetic

<400> SEQUENCE: 6

Met Leu Gln Asn Ser Ala Val Leu Leu Val Leu Val Ile Ser Ala Ser
1               5                   10                  15

Ala Thr His Glu Ala Glu Gln Asp Ile Ile Met Arg Pro Ser Cys Ala
            20                  25                  30

Pro Gly Trp Phe Tyr His Lys Ser Asn Cys Tyr Gly Tyr Phe Arg Lys
        35                  40                  45

Leu Arg Asn Trp Ser Asp Ala Glu Leu Glu Cys Gln Ser Tyr Gly Asn
    50                  55                  60

Gly Ala His Leu Ala Ser Ile Leu Ser Leu Lys Glu Ala Ser Thr Ile
65                  70                  75                  80

Ala Glu Tyr Ile Ser Gly Tyr Gln Arg Ser Gln Pro Ile Trp Ile Gly
                85                  90                  95

Leu His Asp Pro Gln Lys Arg Gln Gln Trp Gln Trp Ile Asp Gly Ala
            100                 105                 110

Met Tyr Leu Tyr Arg Ser Trp Ser Gly Lys Ser Met Gly Gly Asn Lys
        115                 120                 125

His Cys Ala Glu Met Ser Ser Asn Asn Asn Phe Leu Thr Trp Ser Ser
    130                 135                 140

Asn Glu Cys Asn Lys Arg Gln His Phe Leu Cys Lys Tyr Arg Pro Ala
145                 150                 155                 160

Ser His His His His His His His His
                165                 170

<210> SEQ ID NO 7
<211> LENGTH: 212
<212> TYPE: PRT
<213> ORGANISM: ARTIFICIAL SEQUENCE
<220> FEATURE:
<223> OTHER INFORMATION: Synthetic

<400> SEQUENCE: 7

Met Ser Gly Gly His Gln Leu Gln Leu Ala Ala Leu Trp Pro Trp Leu
1               5                   10                  15

Leu Met Ala Thr Leu Gln Ala Gly Phe Gly Arg Thr Gly Leu Val Leu
            20                  25                  30

Ala Ala Ala Val Glu Ser Glu Arg Ser Ala Glu Gln Lys Ala Ile Ile
        35                  40                  45

Arg Val Ile Pro Leu Lys Met Asp Pro Thr Gly Lys Leu Asn Leu Thr
    50                  55                  60

Leu Glu Gly Val Phe Ala Gly Val Ala Glu Ile Thr Pro Ala Glu Gly
65                  70                  75                  80

Lys Leu Met Gln Ser His Pro Leu Tyr Leu Cys Asn Ala Ser Asp Asp
                85                  90                  95

Asp Asn Leu Glu Pro Gly Phe Ile Ser Ile Val Lys Leu Glu Ser Pro
            100                 105                 110

Arg Arg Ala Pro Arg Pro Cys Leu Ser Leu Ala Ser Lys Ala Arg Met
        115                 120                 125

Ala Gly Glu Arg Gly Ala Ser Ala Val Leu Phe Asp Ile Thr Glu Asp
    130                 135                 140

Arg Ala Ala Ala Glu Gln Leu Gln Gln Pro Leu Gly Leu Thr Trp Pro
145                 150                 155                 160

Val Val Leu Ile Trp Gly Asn Asp Ala Glu Lys Leu Met Glu Phe Val
                165                 170                 175
```

Tyr Lys Asn Gln Lys Ala His Val Arg Ile Glu Leu Lys Glu Pro Pro
                180                 185                 190

Ala Trp Pro Asp Tyr Asp Ile Ala Ser His His His His His
            195                 200                 205

His His His His
        210

<210> SEQ ID NO 8
<211> LENGTH: 294
<212> TYPE: PRT
<213> ORGANISM: ARTIFICIAL SEQUENCE
<220> FEATURE:
<223> OTHER INFORMATION: Synthetic

<400> SEQUENCE: 8

Met Ala Ser Leu Gly Gln Ile Leu Phe Trp Ser Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys Ala Ser His His His
            275                 280                 285

His His His His His
        290

<210> SEQ ID NO 9
<211> LENGTH: 15

```
<212> TYPE: PRT
<213> ORGANISM: ARTIFICIAL SEQUENCE
<220> FEATURE:
<223> OTHER INFORMATION: Synthetic

<400> SEQUENCE: 9

Trp Lys Phe Met Gly Ser Lys Cys Ser Asn Ser Gly Ile Glu Cys
 1               5                  10                  15

<210> SEQ ID NO 10
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 10

Ser Gly Ile Glu Cys Asp Ser Ser Gly Thr Cys Ile Asn Pro Ser
 1               5                  10                  15

<210> SEQ ID NO 11
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 11

Cys Ile Asn Pro Ser Asn Trp Cys Asp Gly Val Ser His Cys Pro
 1               5                  10                  15

<210> SEQ ID NO 12
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 12

Val Ser His Cys Pro Gly Gly Glu Asp Glu Asn Arg Cys Val Arg
 1               5                  10                  15

<210> SEQ ID NO 13
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 13

Asn Arg Cys Val Arg Leu Tyr Gly Pro Asn Phe Ile Leu Gln Met
 1               5                  10                  15

<210> SEQ ID NO 14
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 14

Phe Ile Leu Gln Met Tyr Ser Ser Gln Arg Lys Ser Trp His Pro
 1               5                  10                  15

<210> SEQ ID NO 15
<211> LENGTH: 15
<212> TYPE: PRT
<213> ORGANISM: ARTIFICIAL SEQUENCE
```

```
<220> FEATURE:
<223> OTHER INFORMATION: Synthetic

<400> SEQUENCE: 15

Lys Ser Trp His Pro Val Cys Gln Asp Asp Trp Asn Glu Asn Tyr
1               5                   10                  15

<210> SEQ ID NO 16
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 16

Trp Asn Glu Asn Tyr Gly Arg Ala Ala Cys Arg Asp Met Gly Tyr
1               5                   10                  15

<210> SEQ ID NO 17
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 17

Arg Asp Met Gly Tyr Lys Asn Asn Phe Tyr Ser Ser Gln Gly Ile
1               5                   10                  15

<210> SEQ ID NO 18
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 18

Ser Ser Gln Gly Ile Val Asp Asp Ser Gly Ser Thr Ser Phe Met
1               5                   10                  15

<210> SEQ ID NO 19
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 19

Ser Thr Ser Phe Met Lys Leu Asn Thr Ser Ala Gly Asn Val Asp
1               5                   10                  15

<210> SEQ ID NO 20
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 20

Ala Gly Asn Val Asp Ile Tyr Lys Lys Leu Tyr His Ser Asp Ala
1               5                   10                  15

<210> SEQ ID NO 21
<211> LENGTH: 15
<212> TYPE: PRT
<213> ORGANISM: ARTIFICIAL SEQUENCE
<220> FEATURE:
<223> OTHER INFORMATION: Synthetic
```

-continued

<400> SEQUENCE: 21

Tyr His Ser Asp Ala Cys Ser Ser Lys Ala Val Val Ser Leu Arg
1               5                   10                  15

<210> SEQ ID NO 22
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 22

Val Val Ser Leu Arg Cys Ile Ala Cys Gly Val Asn Leu Asn Ser
1               5                   10                  15

<210> SEQ ID NO 23
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 23

Val Asn Leu Asn Ser Ser Arg Gln Ser Arg Ile Val Gly Gly Glu
1               5                   10                  15

<210> SEQ ID NO 24
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 24

Ile Val Gly Gly Glu Ser Ala Leu Pro Gly Ala Trp Pro Trp Gln
1               5                   10                  15

<210> SEQ ID NO 25
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 25

Ala Trp Pro Trp Gln Val Ser Leu His Val Gln Asn Val His Val
1               5                   10                  15

<210> SEQ ID NO 26
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 26

Gln Asn Val His Val Cys Gly Gly Ser Ile Ile Thr Pro Glu Trp
1               5                   10                  15

<210> SEQ ID NO 27
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 27

Ile Thr Pro Glu Trp Ile Val Thr Ala Ala His Cys Val Glu Lys
1               5                   10                  15

<210> SEQ ID NO 28
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 28

His Cys Val Glu Lys Pro Leu Asn Asn Pro Trp His Trp Thr Ala
1               5                   10                  15

<210> SEQ ID NO 29
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 29

Trp His Trp Thr Ala Phe Ala Gly Ile Leu Arg Gln Ser Phe Met
1               5                   10                  15

<210> SEQ ID NO 30
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 30

Arg Gln Ser Phe Met Phe Tyr Gly Ala Gly Tyr Gln Val Glu Lys
1               5                   10                  15

<210> SEQ ID NO 31
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 31

Tyr Gln Val Glu Lys Val Ile Ser His Pro Asn Tyr Asp Ser Lys
1               5                   10                  15

<210> SEQ ID NO 32
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 32

Asn Tyr Asp Ser Lys Thr Lys Asn Asn Asp Ile Ala Leu Met Lys
1               5                   10                  15

<210> SEQ ID NO 33
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 33

Ile Ala Leu Met Lys Leu Gln Lys Pro Leu Thr Phe Asn Asp Leu

-continued

<210> SEQ ID NO 34
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 34

Ile Ala Leu Met Lys Leu Gln Lys Pro Leu Thr Phe Asn Asp Leu
1               5                   10                  15

<210> SEQ ID NO 35
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 35

Leu Pro Asn Pro Gly Met Met Leu Gln Pro Glu Gln Leu Cys Trp
1               5                   10                  15

<210> SEQ ID NO 36
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 36

Glu Gln Leu Cys Trp Ile Ser Gly Trp Gly Ala Thr Glu Glu Lys
1               5                   10                  15

<210> SEQ ID NO 37
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 37

Ala Thr Glu Glu Lys Gly Lys Thr Ser Glu Val Leu Asn Ala Ala
1               5                   10                  15

<210> SEQ ID NO 38
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 38

Val Leu Asn Ala Ala Lys Val Leu Leu Ile Glu Thr Gln Arg Cys
1               5                   10                  15

<210> SEQ ID NO 39
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 39

Glu Thr Gln Arg Cys Asn Ser Arg Tyr Val Tyr Asp Asn Leu Ile
1               5                   10                  15

<210> SEQ ID NO 40
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 40

Tyr Asp Asn Leu Ile Thr Pro Ala Met Ile Cys Ala Gly Phe Leu
1               5                   10                  15

<210> SEQ ID NO 41
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 41

Cys Ala Gly Phe Leu Gln Gly Asn Val Asp Ser Cys Gln Gly Asp
1               5                   10                  15

<210> SEQ ID NO 42
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 42

Ser Cys Gln Gly Asp Ser Gly Gly Pro Leu Val Thr Ser Lys Asn
1               5                   10                  15

<210> SEQ ID NO 43
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 43

Val Thr Ser Lys Asn Asn Ile Trp Trp Leu Ile Gly Asp Thr Ser
1               5                   10                  15

<210> SEQ ID NO 44
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 44

Ile Gly Asp Thr Ser Trp Gly Ser Gly Cys Ala Lys Ala Tyr Arg
1               5                   10                  15

<210> SEQ ID NO 45
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 45

Ala Lys Ala Tyr Arg Pro Gly Val Tyr Gly Asn Val Met Val Phe
1               5                   10                  15

<210> SEQ ID NO 46

```
<211> LENGTH: 15
<212> TYPE: PRT
<213> ORGANISM: ARTIFICIAL SEQUENCE
<220> FEATURE:
<223> OTHER INFORMATION: Synthetic

<400> SEQUENCE: 46

Asn Val Met Val Phe Thr Asp Trp Ile Tyr Arg Gln Met Arg Ala
1               5                   10                  15

<210> SEQ ID NO 47
<211> LENGTH: 7
<212> TYPE: PRT
<213> ORGANISM: ARTIFICIAL SEQUENCE
<220> FEATURE:
<223> OTHER INFORMATION: Synthetic

<400> SEQUENCE: 47

Arg Gln Met Arg Ala Asp Gly
1               5

<210> SEQ ID NO 48
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 48

Val Ser His Cys Pro
1               5

<210> SEQ ID NO 49
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 49

Val Asp Ser Cys Gln
1               5

<210> SEQ ID NO 50
<211> LENGTH: 4
<212> TYPE: PRT
<213> ORGANISM: ARTIFICIAL SEQUENCE
<220> FEATURE:
<223> OTHER INFORMATION: Synthetic

<400> SEQUENCE: 50

Arg Asp Met Gly
1

<210> SEQ ID NO 51
<211> LENGTH: 4
<212> TYPE: PRT
<213> ORGANISM: ARTIFICIAL SEQUENCE
<220> FEATURE:
<223> OTHER INFORMATION: Synthetic

<400> SEQUENCE: 51

Lys Asp Met Gly
1

<210> SEQ ID NO 52
<211> LENGTH: 4
<212> TYPE: PRT
```

```
<213> ORGANISM: ARTIFICIAL SEQUENCE
<220> FEATURE:
<223> OTHER INFORMATION: Synthetic

<400> SEQUENCE: 52

Asp Ser Ser Gly
1

<210> SEQ ID NO 53
<211> LENGTH: 4
<212> TYPE: PRT
<213> ORGANISM: ARTIFICIAL SEQUENCE
<220> FEATURE:
<223> OTHER INFORMATION: Synthetic

<400> SEQUENCE: 53

Gly Ser Ser Gly
1

<210> SEQ ID NO 54
<211> LENGTH: 4
<212> TYPE: PRT
<213> ORGANISM: ARTIFICIAL SEQUENCE
<220> FEATURE:
<223> OTHER INFORMATION: Synthetic

<400> SEQUENCE: 54

Tyr Gln Val Glu
1

<210> SEQ ID NO 55
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 55

Asn Tyr Asp Ser Lys
1               5

<210> SEQ ID NO 56
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 56

Val Tyr Asp Asn Leu
1               5

<210> SEQ ID NO 57
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 57

Asn Leu Asn Ser Ser
1               5

<210> SEQ ID NO 58
<211> LENGTH: 4
<212> TYPE: PRT
<213> ORGANISM: ARTIFICIAL SEQUENCE
<220> FEATURE:
```

<223> OTHER INFORMATION: Synthetic

<400> SEQUENCE: 58

Lys Pro Leu Thr
1

<210> SEQ ID NO 59
<211> LENGTH: 4
<212> TYPE: PRT
<213> ORGANISM: ARTIFICIAL SEQUENCE
<220> FEATURE:
<223> OTHER INFORMATION: Synthetic

<400> SEQUENCE: 59

Thr Pro Leu Ala
1

<210> SEQ ID NO 60
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 60

Arg Tyr Val Tyr Asp
1               5

<210> SEQ ID NO 61
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 61

Lys Tyr Ile Tyr Asn
1               5

<210> SEQ ID NO 62
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 62

Gln Pro Glu Gln Leu
1               5

<210> SEQ ID NO 63
<211> LENGTH: 5
<212> TYPE: PRT
<213> ORGANISM: ARTIFICIAL SEQUENCE
<220> FEATURE:
<223> OTHER INFORMATION: Synthetic

<400> SEQUENCE: 63

Asp Leu Asp Gln Glu
1               5

<210> SEQ ID NO 64
<211> LENGTH: 4
<212> TYPE: PRT
<213> ORGANISM: ARTIFICIAL SEQUENCE
<220> FEATURE:
<223> OTHER INFORMATION: Synthetic

```
<400> SEQUENCE: 64

Val Thr Ser Lys
1

<210> SEQ ID NO 65
<211> LENGTH: 4
<212> TYPE: PRT
<213> ORGANISM: ARTIFICIAL SEQUENCE
<220> FEATURE:
<223> OTHER INFORMATION: Synthetic

<400> SEQUENCE: 65

Val Thr Leu Lys
1

<210> SEQ ID NO 66
<211> LENGTH: 492
<212> TYPE: PRT
<213> ORGANISM: Homo sapien
<220> FEATURE:
<221> NAME/KEY: VARIANT
<222> LOCATION: (12)..(12)
<223> OTHER INFORMATION: glycine or glutamic acid
<220> FEATURE:
<221> NAME/KEY: VARIANT
<222> LOCATION: (160)..(160)
<223> OTHER INFORMATION: methionine or valine
<220> FEATURE:
<221> NAME/KEY: VARIANT
<222> LOCATION: (449)..(449)
<223> OTHER INFORMATION: lysine or asparagine

<400> SEQUENCE: 66

Met Ala Leu Asn Ser Gly Ser Pro Pro Ala Ile Xaa Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45

Val Pro Gln Tyr Ala Pro Arg Val Leu Thr Gln Ala Ser Asn Pro Val
    50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
        115                 120                 125

Pro Ser Asn Trp Cys Asp Gly Val Ser His Cys Pro Gly Gly Glu Asp
    130                 135                 140

Glu Asn Arg Cys Val Arg Leu Tyr Gly Pro Asn Phe Ile Leu Gln Xaa
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220
```

```
Leu Tyr His Ser Asp Ala Cys Ser Ser Lys Ala Val Val Ser Leu Arg
225                 230                 235                 240

Cys Ile Ala Cys Gly Val Asn Leu Asn Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
                275                 280                 285

Glu Trp Ile Val Thr Ala Ala His Cys Val Glu Lys Pro Leu Asn Asn
            290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
                355                 360                 365

Pro Gly Met Met Leu Gln Pro Glu Gln Leu Cys Trp Ile Ser Gly Trp
370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
            420                 425                 430

Asn Val Asp Ser Cys Gln Gly Asp Ser Gly Gly Pro Leu Val Thr Ser
            435                 440                 445

Xaa Asn Asn Ile Trp Trp Leu Ile Gly Asp Thr Ser Trp Gly Ser Gly
450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Arg Ala Asp Gly
                485                 490

<210> SEQ ID NO 67
<211> LENGTH: 490
<212> TYPE: PRT
<213> ORGANISM: Mus musculus

<400> SEQUENCE: 67

Met Ala Leu Asn Ser Gly Ser Pro Pro Gly Ile Gly Pro Cys Tyr Glu
1               5                   10                  15

Asn His Gly Tyr Gln Ser Glu His Ile Cys Pro Pro Arg Pro Pro Val
                20                  25                  30

Ala Pro Asn Gly Tyr Asn Leu Tyr Pro Ala Gln Tyr Tyr Pro Ser Pro
            35                  40                  45

Val Pro Gln Tyr Ala Pro Arg Ile Thr Thr Gln Ala Ser Thr Ser Val
50                  55                  60

Ile His Thr His Pro Lys Ser Ser Gly Ala Leu Cys Thr Ser Lys Ser
65                  70                  75                  80

Lys Lys Ser Leu Cys Leu Ala Leu Ala Leu Gly Thr Val Leu Thr Gly
                85                  90                  95

Ala Ala Val Ala Ala Val Leu Leu Trp Arg Phe Trp Asp Ser Asn Cys
            100                 105                 110
```

-continued

```
Ser Thr Ser Glu Met Glu Cys Gly Ser Ser Gly Thr Cys Ile Ser Ser
            115                 120                 125

Ser Leu Trp Cys Asp Gly Val Ala His Cys Pro Asn Gly Glu Asp Glu
    130                 135                 140

Asn Arg Cys Val Arg Leu Tyr Gly Gln Ser Phe Ile Leu Gln Val Tyr
145                 150                 155                 160

Ser Ser Gln Arg Lys Ala Trp Tyr Pro Val Cys Gln Asp Asp Trp Ser
                165                 170                 175

Glu Ser Tyr Gly Arg Ala Ala Cys Lys Asp Met Gly Tyr Lys Asn Asn
                180                 185                 190

Phe Tyr Ser Ser Gln Gly Ile Pro Asp Gln Ser Gly Ala Thr Ser Phe
                195                 200                 205

Met Lys Leu Asn Val Ser Ser Gly Asn Val Asp Leu Tyr Lys Lys Leu
    210                 215                 220

Tyr His Ser Asp Ser Cys Ser Ser Arg Met Val Val Ser Leu Arg Cys
225                 230                 235                 240

Ile Glu Cys Gly Val Arg Ser Val Lys Arg Gln Ser Arg Ile Val Gly
                245                 250                 255

Gly Leu Asn Ala Ser Pro Gly Asp Trp Pro Trp Gln Val Ser Leu His
            260                 265                 270

Val Gln Gly Val His Val Cys Gly Gly Ser Ile Ile Thr Pro Glu Trp
    275                 280                 285

Ile Val Thr Ala Ala His Cys Val Glu Glu Pro Leu Ser Ser Pro Arg
290                 295                 300

Tyr Trp Thr Ala Phe Ala Gly Ile Leu Arg Gln Ser Leu Met Phe Tyr
305                 310                 315                 320

Gly Ser Arg His Gln Val Glu Lys Val Ile Ser His Pro Asn Tyr Asp
                325                 330                 335

Ser Lys Thr Lys Asn Asn Asp Ile Ala Leu Met Lys Leu Gln Thr Pro
                340                 345                 350

Leu Ala Phe Asn Asp Leu Val Lys Pro Val Cys Leu Pro Asn Pro Gly
                355                 360                 365

Met Met Leu Asp Leu Asp Gln Glu Cys Trp Ile Ser Gly Trp Gly Ala
    370                 375                 380

Thr Tyr Glu Lys Gly Lys Thr Ser Asp Val Leu Asn Ala Ala Met Val
385                 390                 395                 400

Pro Leu Ile Glu Pro Ser Lys Cys Asn Ser Lys Tyr Ile Tyr Asn Asn
                405                 410                 415

Leu Ile Thr Pro Ala Met Ile Cys Ala Gly Phe Leu Gln Gly Ser Val
                420                 425                 430

Asp Ser Cys Gln Gly Asp Ser Gly Gly Pro Leu Val Thr Leu Lys Asn
                435                 440                 445

Gly Ile Trp Trp Leu Ile Gly Asp Thr Ser Trp Gly Ser Gly Cys Ala
    450                 455                 460

Lys Ala Leu Arg Pro Gly Val Tyr Gly Asn Val Thr Val Phe Thr Asp
465                 470                 475                 480

Trp Ile Tyr Gln Gln Met Arg Ala Asn Ser
                485                 490

<210> SEQ ID NO 68
<211> LENGTH: 417
<212> TYPE: PRT
<213> ORGANISM: Homo sapien

<400> SEQUENCE: 68
```

```
Met Ala Gln Lys Glu Gly Gly Arg Thr Val Pro Cys Cys Ser Arg Pro
1               5                   10                  15

Lys Val Ala Ala Leu Thr Ala Gly Thr Leu Leu Leu Thr Ala Ile
            20                  25                  30

Gly Ala Ala Ser Trp Ala Ile Val Ala Val Leu Leu Arg Ser Asp Gln
                35                  40                  45

Glu Pro Leu Tyr Pro Val Gln Val Ser Ser Ala Asp Ala Arg Leu Met
50                  55                  60

Val Phe Asp Lys Thr Glu Gly Thr Trp Arg Leu Leu Cys Ser Ser Arg
65                  70                  75                  80

Ser Asn Ala Arg Val Ala Gly Leu Ser Cys Glu Glu Met Gly Phe Leu
                85                  90                  95

Arg Ala Leu Thr His Ser Glu Leu Asp Val Arg Thr Ala Gly Ala Asn
            100                 105                 110

Gly Thr Ser Gly Phe Phe Cys Val Asp Glu Gly Arg Leu Pro His Thr
                115                 120                 125

Gln Arg Leu Leu Glu Val Ile Ser Val Cys Asp Cys Pro Arg Gly Arg
    130                 135                 140

Phe Leu Ala Ala Ile Cys Gln Asp Cys Gly Arg Arg Lys Leu Pro Val
145                 150                 155                 160

Asp Arg Ile Val Gly Gly Arg Asp Thr Ser Leu Gly Arg Trp Pro Trp
                165                 170                 175

Gln Val Ser Leu Arg Tyr Asp Gly Ala His Leu Cys Gly Gly Ser Leu
                180                 185                 190

Leu Ser Gly Asp Trp Val Leu Thr Ala Ala His Cys Phe Pro Glu Arg
    195                 200                 205

Asn Arg Val Leu Ser Arg Trp Arg Val Phe Ala Gly Ala Val Ala Gln
210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
                245                 250                 255

Asp Ile Ala Leu Val His Leu Ser Ser Pro Leu Pro Leu Thr Glu Tyr
                260                 265                 270

Ile Gln Pro Val Cys Leu Pro Ala Ala Gly Gln Ala Leu Val Asp Gly
                275                 280                 285

Lys Ile Cys Thr Val Thr Gly Trp Gly Asn Thr Gln Tyr Tyr Gly Gln
290                 295                 300

Gln Ala Gly Val Leu Gln Glu Ala Arg Val Pro Ile Ile Ser Asn Asp
305                 310                 315                 320

Val Cys Asn Gly Ala Asp Phe Tyr Gly Asn Gln Ile Lys Pro Lys Met
                325                 330                 335

Phe Cys Ala Gly Tyr Pro Glu Gly Gly Ile Asp Ala Cys Gln Gly Asp
                340                 345                 350

Ser Gly Gly Pro Phe Val Cys Glu Asp Ser Ile Ser Arg Thr Pro Arg
            355                 360                 365

Trp Arg Leu Cys Gly Ile Val Ser Trp Gly Thr Gly Cys Ala Leu Ala
            370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
                405                 410                 415

Leu
```

<210> SEQ ID NO 69
<211> LENGTH: 454
<212> TYPE: PRT
<213> ORGANISM: Homo sapien

<400> SEQUENCE: 69

```
Met Gly Glu Asn Asp Pro Pro Ala Val Glu Ala Pro Phe Ser Phe Arg
1               5                   10                  15

Ser Leu Phe Gly Leu Asp Asp Leu Lys Ile Ser Pro Val Ala Pro Asp
            20                  25                  30

Ala Asp Ala Val Ala Ala Gln Ile Leu Ser Leu Leu Pro Leu Lys Phe
        35                  40                  45

Phe Pro Ile Ile Val Ile Gly Ile Ile Ala Leu Ile Leu Ala Leu Ala
    50                  55                  60

Ile Gly Leu Gly Ile His Phe Asp Cys Ser Gly Lys Tyr Arg Cys Arg
65                  70                  75                  80

Ser Ser Phe Lys Cys Ile Glu Leu Ile Ala Arg Cys Asp Gly Val Ser
                85                  90                  95

Asp Cys Lys Asp Gly Glu Asp Glu Tyr Arg Cys Val Arg Val Gly Gly
            100                 105                 110

Gln Asn Ala Val Leu Gln Val Phe Thr Ala Ala Ser Trp Lys Thr Met
        115                 120                 125

Cys Ser Asp Asp Trp Lys Gly His Tyr Ala Asn Val Ala Cys Ala Gln
    130                 135                 140

Leu Gly Phe Pro Ser Tyr Val Ser Ser Asp Asn Leu Arg Val Ser Ser
145                 150                 155                 160

Leu Glu Gly Gln Phe Arg Glu Glu Phe Val Ser Ile Asp His Leu Leu
                165                 170                 175

Pro Asp Asp Lys Val Thr Ala Leu His His Ser Val Tyr Val Arg Glu
            180                 185                 190

Gly Cys Ala Ser Gly His Val Val Thr Leu Gln Cys Thr Ala Cys Gly
        195                 200                 205

His Arg Arg Gly Tyr Ser Ser Arg Ile Val Gly Gly Asn Met Ser Leu
    210                 215                 220

Leu Ser Gln Trp Pro Trp Gln Ala Ser Leu Gln Phe Gln Gly Tyr His
225                 230                 235                 240

Leu Cys Gly Gly Ser Val Ile Thr Pro Leu Trp Ile Ile Thr Ala Ala
                245                 250                 255

His Cys Val Tyr Asp Leu Tyr Leu Pro Lys Ser Trp Thr Ile Gln Val
            260                 265                 270

Gly Leu Val Ser Leu Leu Asp Asn Pro Ala Pro Ser His Leu Val Glu
        275                 280                 285

Lys Ile Val Tyr His Ser Lys Tyr Lys Pro Lys Arg Leu Gly Asn Asp
    290                 295                 300

Ile Ala Leu Met Lys Leu Ala Gly Pro Leu Thr Phe Asn Glu Met Ile
305                 310                 315                 320

Gln Pro Val Cys Leu Pro Asn Ser Glu Glu Asn Phe Pro Asp Gly Lys
                325                 330                 335

Val Cys Trp Thr Ser Gly Trp Gly Ala Thr Glu Asp Gly Ala Gly Asp
            340                 345                 350

Ala Ser Pro Val Leu Asn His Ala Ala Val Pro Leu Ile Ser Asn Lys
        355                 360                 365

Ile Cys Asn His Arg Asp Val Tyr Gly Gly Ile Ile Ser Pro Ser Met
    370                 375                 380
```

```
Leu Cys Ala Gly Tyr Leu Thr Gly Gly Val Asp Ser Cys Gln Gly Asp
385                 390                 395                 400

Ser Gly Gly Pro Leu Val Cys Gln Glu Arg Arg Leu Trp Lys Leu Val
            405                 410                 415

Gly Ala Thr Ser Phe Gly Ile Gly Cys Ala Glu Val Asn Lys Pro Gly
        420                 425                 430

Val Tyr Thr Arg Val Thr Ser Phe Leu Asp Trp Ile His Glu Gln Met
            435                 440                 445

Glu Arg Asp Leu Lys Thr
            450
```

<210> SEQ ID NO 70
<211> LENGTH: 437
<212> TYPE: PRT
<213> ORGANISM: Homo sapien

<400> SEQUENCE: 70

```
Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
            20                  25                  30

Gly Ile Pro Ile Ile Ile Ala Leu Leu Ser Leu Ala Ser Ile Ile Ile
        35                  40                  45

Val Val Val Leu Ile Lys Val Ile Leu Asp Lys Tyr Tyr Phe Leu Cys
    50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu His Cys Val Lys Ser Phe
                85                  90                  95

Pro Glu Gly Pro Ala Val Ala Val Arg Leu Ser Lys Asp Arg Ser Thr
            100                 105                 110

Leu Gln Val Leu Asp Ser Ala Thr Gly Asn Trp Phe Ser Ala Cys Phe
        115                 120                 125

Asp Asn Phe Thr Glu Ala Leu Ala Glu Thr Ala Cys Arg Gln Met Gly
130                 135                 140

Tyr Ser Ser Lys Pro Thr Phe Arg Ala Val Glu Ile Gly Pro Asp Gln
145                 150                 155                 160

Asp Leu Asp Val Val Glu Ile Thr Glu Asn Ser Gln Glu Leu Arg Met
            165                 170                 175

Arg Asn Ser Ser Gly Pro Cys Leu Ser Gly Ser Leu Val Ser Leu His
        180                 185                 190

Cys Leu Ala Cys Gly Lys Ser Leu Lys Thr Pro Arg Val Val Gly Gly
    195                 200                 205

Glu Glu Ala Ser Val Asp Ser Trp Pro Trp Gln Val Ser Ile Gln Tyr
210                 215                 220

Asp Lys Gln His Val Cys Gly Gly Ser Ile Leu Asp Pro His Trp Val
225                 230                 235                 240

Leu Thr Ala Ala His Cys Phe Arg Lys His Thr Asp Val Phe Asn Trp
            245                 250                 255

Lys Val Arg Ala Gly Ser Asp Lys Leu Gly Ser Phe Pro Ser Leu Ala
        260                 265                 270

Val Ala Lys Ile Ile Ile Ile Glu Phe Asn Pro Met Tyr Pro Lys Asp
    275                 280                 285

Asn Asp Ile Ala Leu Met Lys Leu Gln Phe Pro Leu Thr Phe Ser Gly
290                 295                 300
```

```
Thr Val Arg Pro Ile Cys Leu Pro Phe Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335

Gly Lys Met Ser Asp Ile Leu Leu Gln Ala Ser Val Gln Val Ile Asp
                340                 345                 350

Ser Thr Arg Cys Asn Ala Asp Ala Tyr Gln Gly Glu Val Thr Glu
                355                 360                 365

Lys Met Met Cys Ala Gly Ile Pro Glu Gly Gly Val Asp Thr Cys Gln
370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
                420                 425                 430

Trp Lys Ala Glu Leu
                435

<210> SEQ ID NO 71
<211> LENGTH: 457
<212> TYPE: PRT
<213> ORGANISM: Homo sapien

<400> SEQUENCE: 71

Met Ser Leu Met Leu Asp Asp Gln Pro Pro Met Glu Ala Gln Tyr Ala
1               5                   10                  15

Glu Glu Gly Pro Gly Pro Gly Ile Phe Arg Ala Glu Pro Gly Asp Gln
                20                  25                  30

Gln His Pro Ile Ser Gln Ala Val Cys Trp Arg Ser Met Arg Arg Gly
            35                  40                  45

Cys Ala Val Leu Gly Ala Leu Gly Leu Leu Ala Gly Ala Gly Val Gly
        50                  55                  60

Ser Trp Leu Leu Val Leu Tyr Leu Cys Pro Ala Ala Ser Gln Pro Ile
65                  70                  75                  80

Ser Gly Thr Leu Gln Asp Glu Glu Ile Thr Leu Ser Cys Ser Glu Ala
                85                  90                  95

Ser Ala Glu Glu Ala Leu Leu Pro Ala Leu Pro Lys Thr Val Ser Phe
                100                 105                 110

Arg Ile Asn Ser Glu Asp Phe Leu Leu Glu Ala Gln Val Arg Asp Gln
                115                 120                 125

Pro Arg Trp Leu Leu Val Cys His Glu Gly Trp Ser Pro Ala Leu Gly
            130                 135                 140

Leu Gln Ile Cys Trp Ser Leu Gly His Leu Arg Leu Thr His His Lys
145                 150                 155                 160

Gly Val Asn Leu Thr Asp Ile Lys Leu Asn Ser Ser Gln Glu Phe Ala
                165                 170                 175

Gln Leu Ser Pro Arg Leu Gly Gly Phe Leu Glu Glu Ala Trp Gln Pro
                180                 185                 190

Arg Asn Asn Cys Thr Ser Gly Gln Val Val Ser Leu Arg Cys Ser Glu
                195                 200                 205

Cys Gly Ala Arg Pro Leu Ala Ser Arg Ile Val Gly Gly Gln Ser Val
            210                 215                 220

Ala Pro Gly Arg Trp Pro Trp Gln Ala Ser Val Ala Leu Gly Phe Arg
225                 230                 235                 240
```

```
His Thr Cys Gly Gly Ser Val Leu Ala Pro Arg Trp Val Thr Ala
                245                 250                 255
Ala His Cys Met His Ser Phe Arg Leu Ala Arg Leu Ser Ser Trp Arg
                260                 265                 270
Val His Ala Gly Leu Val Ser His Ser Ala Val Arg Pro His Gln Gly
                275                 280                 285
Ala Leu Val Glu Arg Ile Ile Pro His Pro Leu Tyr Ser Ala Gln Asn
                290                 295                 300
His Asp Tyr Asp Val Ala Leu Leu Arg Leu Gln Thr Ala Leu Asn Phe
305                 310                 315                 320
Ser Asp Thr Val Gly Ala Val Cys Leu Pro Ala Lys Glu Gln His Phe
                325                 330                 335
Pro Lys Gly Ser Arg Cys Trp Val Ser Gly Trp Gly His Thr His Pro
                340                 345                 350
Ser His Thr Tyr Ser Ser Asp Met Leu Gln Asp Thr Val Val Pro Leu
                355                 360                 365
Phe Ser Thr Gln Leu Cys Asn Ser Ser Cys Val Tyr Ser Gly Ala Leu
                370                 375                 380
Thr Pro Arg Met Leu Cys Ala Gly Tyr Leu Asp Gly Arg Ala Asp Ala
385                 390                 395                 400
Cys Gln Gly Asp Ser Gly Gly Pro Leu Val Cys Pro Asp Gly Asp Thr
                405                 410                 415
Trp Arg Leu Val Gly Val Val Ser Trp Gly Arg Ala Cys Ala Glu Pro
                420                 425                 430
Asn His Pro Gly Val Tyr Ala Lys Val Ala Glu Phe Leu Asp Trp Ile
                435                 440                 445
His Asp Thr Ala Gln Asp Ser Leu Leu
    450                 455

<210> SEQ ID NO 72
<211> LENGTH: 811
<212> TYPE: PRT
<213> ORGANISM: Homo sapien

<400> SEQUENCE: 72

Met Leu Leu Leu Phe His Ser Lys Arg Met Pro Val Ala Glu Ala Pro
1               5                   10                  15
Gln Val Ala Gly Gly Gln Asp Gly Asp Gly Glu Glu Ala Glu
                20                  25                  30
Pro Glu Gly Met Phe Lys Ala Cys Glu Asp Ser Lys Arg Lys Ala Arg
                35                  40                  45
Gly Tyr Leu Arg Leu Val Pro Leu Phe Val Leu Leu Ala Leu Leu Val
                50                  55                  60
Leu Ala Ser Ala Gly Val Leu Leu Trp Tyr Phe Leu Gly Tyr Lys Ala
65                  70                  75                  80
Glu Val Met Val Ser Gln Val Tyr Ser Gly Ser Leu Arg Val Leu Asn
                85                  90                  95
Arg His Phe Ser Gln Asp Leu Thr Arg Arg Glu Ser Ser Ala Phe Arg
                100                 105                 110
Ser Glu Thr Ala Lys Ala Gln Lys Met Leu Lys Glu Leu Ile Thr Ser
                115                 120                 125
Thr Arg Leu Gly Thr Tyr Tyr Asn Ser Ser Ser Val Tyr Ser Phe Gly
                130                 135                 140
Glu Gly Pro Leu Thr Cys Phe Phe Trp Phe Ile Leu Gln Ile Pro Glu
145                 150                 155                 160
```

-continued

His Arg Arg Leu Met Leu Ser Pro Glu Val Gln Ala Leu Leu Val
            165                 170                 175

Glu Glu Leu Leu Ser Thr Val Asn Ser Ala Ala Val Pro Tyr Arg
        180                 185                 190

Ala Glu Tyr Glu Val Asp Pro Glu Gly Leu Val Ile Leu Glu Ala Ser
        195                 200                 205

Val Lys Asp Ile Ala Ala Leu Asn Ser Thr Leu Gly Cys Arg Tyr
210                 215                 220

Ser Tyr Val Gly Gln Gly Gln Val Leu Arg Leu Lys Gly Pro Asp His
225                 230                 235                 240

Leu Ala Ser Ser Cys Leu Trp His Leu Gln Gly Pro Lys Asp Leu Met
                245                 250                 255

Leu Lys Leu Arg Leu Glu Trp Thr Leu Ala Glu Cys Arg Asp Arg Leu
                260                 265                 270

Ala Met Tyr Asp Val Ala Gly Pro Leu Glu Lys Arg Leu Ile Thr Ser
            275                 280                 285

Val Tyr Gly Cys Ser Arg Gln Glu Pro Val Val Glu Val Leu Ala Ser
        290                 295                 300

Gly Ala Ile Met Ala Val Val Trp Lys Lys Gly Leu His Ser Tyr Tyr
305                 310                 315                 320

Asp Pro Phe Val Leu Ser Val Gln Pro Val Phe Gln Ala Cys Glu
                325                 330                 335

Val Asn Leu Thr Leu Asp Asn Arg Leu Asp Ser Gln Gly Val Leu Ser
                340                 345                 350

Thr Pro Tyr Phe Pro Ser Tyr Tyr Ser Pro Gln Thr His Cys Ser Trp
            355                 360                 365

His Leu Thr Val Pro Ser Leu Asp Tyr Gly Leu Ala Leu Trp Phe Asp
    370                 375                 380

Ala Tyr Ala Leu Arg Arg Gln Lys Tyr Asp Leu Pro Cys Thr Gln Gly
385                 390                 395                 400

Gln Trp Thr Ile Gln Asn Arg Arg Leu Cys Gly Leu Arg Ile Leu Gln
                405                 410                 415

Pro Tyr Ala Glu Arg Ile Pro Val Ala Thr Ala Gly Ile Thr Ile
            420                 425                 430

Asn Phe Thr Ser Gln Ile Ser Leu Thr Gly Pro Gly Val Arg Val His
        435                 440                 445

Tyr Gly Leu Tyr Asn Gln Ser Asp Pro Cys Pro Gly Glu Phe Leu Cys
    450                 455                 460

Ser Val Asn Gly Leu Cys Val Pro Ala Cys Asp Gly Val Lys Asp Cys
465                 470                 475                 480

Pro Asn Gly Leu Asp Glu Arg Asn Cys Val Cys Arg Ala Thr Phe Gln
                485                 490                 495

Cys Lys Glu Asp Ser Thr Cys Ile Ser Leu Pro Lys Val Cys Asp Gly
            500                 505                 510

Gln Pro Asp Cys Leu Asn Gly Ser Asp Glu Glu Cys Gln Glu Gly
        515                 520                 525

Val Pro Cys Gly Thr Phe Thr Phe Gln Cys Glu Asp Arg Ser Cys Val
    530                 535                 540

Lys Lys Pro Asn Pro Gln Cys Asp Gly Arg Pro Asp Cys Arg Asp Gly
545                 550                 555                 560

Ser Asp Glu Glu His Cys Asp Cys Gly Leu Gln Gly Pro Ser Ser Arg
                565                 570                 575

Ile Val Gly Gly Ala Val Ser Ser Glu Gly Glu Trp Pro Trp Gln Ala
            580                 585                 590

```
Ser Leu Gln Val Arg Gly Arg His Ile Cys Gly Gly Ala Leu Ile Ala
        595                 600                 605

Asp Arg Trp Val Ile Thr Ala Ala His Cys Phe Gln Glu Asp Ser Met
610                 615                 620

Ala Ser Thr Val Leu Trp Thr Val Phe Leu Gly Lys Val Trp Gln Asn
625                 630                 635                 640

Ser Arg Trp Pro Gly Glu Val Ser Phe Lys Val Ser Arg Leu Leu Leu
                645                 650                 655

His Pro Tyr His Glu Glu Asp Ser His Asp Tyr Asp Val Ala Leu Leu
            660                 665                 670

Gln Leu Asp His Pro Val Val Arg Ser Ala Ala Val Arg Pro Val Cys
        675                 680                 685

Leu Pro Ala Arg Ser His Phe Phe Glu Pro Gly Leu His Cys Trp Ile
    690                 695                 700

Thr Gly Trp Gly Ala Leu Arg Glu Gly Gly Pro Ile Ser Asn Ala Leu
705                 710                 715                 720

Gln Lys Val Asp Val Gln Leu Ile Pro Gln Asp Leu Cys Ser Glu Val
                725                 730                 735

Tyr Arg Tyr Gln Val Thr Pro Arg Met Leu Cys Ala Gly Tyr Arg Lys
            740                 745                 750

Gly Lys Lys Asp Ala Cys Gln Gly Asp Ser Gly Gly Pro Leu Val Cys
        755                 760                 765

Lys Ala Leu Ser Gly Arg Trp Phe Leu Ala Gly Leu Val Ser Trp Gly
    770                 775                 780

Leu Gly Cys Gly Arg Pro Asn Tyr Phe Gly Val Tyr Thr Arg Ile Thr
785                 790                 795                 800

Gly Val Ile Ser Trp Ile Gln Gln Val Val Thr
                805                 810

<210> SEQ ID NO 73
<211> LENGTH: 572
<212> TYPE: PRT
<213> ORGANISM: Homo sapien

<400> SEQUENCE: 73

Met Cys His Phe Lys Leu Val Ala Ile Val Gly Tyr Leu Ile Arg Leu
1               5                   10                  15

Ser Ile Lys Ser Ile Gln Ile Glu Ala Asp Asn Cys Val Thr Asp Ser
                20                  25                  30

Leu Thr Ile Tyr Asp Ser Leu Leu Pro Ile Arg Ser Ser Ile Leu Tyr
            35                  40                  45

Arg Ile Cys Glu Pro Thr Arg Thr Leu Met Ser Phe Val Ser Thr Asn
        50                  55                  60

Asn Leu Met Leu Val Thr Phe Lys Ser Pro His Ile Arg Arg Leu Ser
65                  70                  75                  80

Gly Ile Arg Ala Tyr Phe Glu Val Ile Pro Glu Gln Lys Cys Glu Asn
                85                  90                  95

Thr Val Leu Val Lys Asp Ile Thr Gly Phe Glu Gly Lys Ile Ser Ser
            100                 105                 110

Pro Tyr Tyr Pro Ser Tyr Tyr Pro Pro Lys Cys Lys Cys Thr Trp Lys
        115                 120                 125

Phe Gln Thr Ser Leu Ser Thr Leu Gly Ile Ala Leu Lys Phe Tyr Asn
    130                 135                 140

Tyr Ser Ile Thr Lys Lys Ser Met Lys Gly Cys Glu His Gly Trp Trp
145                 150                 155                 160
```

```
Glu Ile Asn Glu His Met Tyr Cys Gly Ser Tyr Met Asp His Gln Thr
                165                 170                 175
Ile Phe Arg Val Pro Ser Pro Leu Val His Ile Gln Leu Gln Cys Ser
            180                 185                 190
Ser Arg Leu Ser Asp Lys Pro Leu Leu Ala Glu Tyr Gly Ser Tyr Asn
        195                 200                 205
Ile Ser Gln Pro Cys Pro Val Gly Ser Phe Arg Cys Ser Ser Gly Leu
    210                 215                 220
Cys Val Pro Gln Ala Gln Arg Cys Asp Gly Val Asn Asp Cys Phe Asp
225                 230                 235                 240
Glu Ser Asp Glu Leu Phe Cys Val Ser Pro Gln Pro Ala Cys Asn Thr
                245                 250                 255
Ser Ser Phe Arg Gln His Gly Pro Leu Ile Cys Asp Gly Phe Arg Asp
            260                 265                 270
Cys Glu Asn Gly Arg Asp Glu Gln Asn Cys Thr Gln Ser Ile Pro Cys
        275                 280                 285
Asn Asn Arg Thr Phe Lys Cys Gly Asn Asp Ile Cys Phe Arg Lys Gln
    290                 295                 300
Asn Ala Lys Cys Asp Gly Thr Val Asp Cys Pro Asp Gly Ser Asp Glu
305                 310                 315                 320
Glu Gly Cys Thr Cys Ser Arg Ser Ser Ala Leu His Arg Ile Ile
                325                 330                 335
Gly Gly Thr Asp Thr Leu Glu Gly Gly Trp Pro Trp Gln Val Ser Leu
            340                 345                 350
His Phe Val Gly Ser Ala Tyr Cys Gly Ala Ser Val Ile Ser Arg Glu
        355                 360                 365
Trp Leu Leu Ser Ala Ala His Cys Phe His Gly Asn Arg Leu Ser Asp
    370                 375                 380
Pro Thr Pro Trp Thr Ala His Leu Gly Met Tyr Val Gln Gly Asn Ala
385                 390                 395                 400
Lys Phe Val Ser Pro Val Arg Arg Ile Val His Glu Tyr Tyr Asn
                405                 410                 415
Ser Gln Thr Phe Asp Tyr Asp Ile Ala Leu Leu Gln Leu Ser Ile Ala
            420                 425                 430
Trp Pro Glu Thr Leu Lys Gln Leu Ile Gln Pro Ile Cys Ile Pro Pro
        435                 440                 445
Thr Gly Gln Arg Val Arg Ser Gly Glu Lys Cys Trp Val Thr Gly Trp
    450                 455                 460
Gly Arg Arg His Glu Ala Asp Asn Lys Gly Ser Leu Val Leu Gln Gln
465                 470                 475                 480
Ala Glu Val Glu Leu Ile Asp Gln Thr Leu Cys Val Ser Thr Tyr Gly
                485                 490                 495
Ile Ile Thr Ser Arg Met Leu Cys Ala Gly Ile Met Ser Gly Lys Arg
            500                 505                 510
Asp Ala Cys Lys Gly Asp Ser Gly Gly Pro Leu Ser Cys Arg Arg Lys
        515                 520                 525
Ser Asp Gly Lys Trp Ile Leu Thr Gly Ile Val Ser Trp Gly His Gly
    530                 535                 540
Ser Gly Arg Pro Asn Phe Pro Gly Val Tyr Thr Arg Val Ser Asn Phe
545                 550                 555                 560
Val Pro Trp Ile His Lys Tyr Val Pro Ser Leu Leu
                565                 570
```

-continued

```
<210> SEQ ID NO 74
<211> LENGTH: 1059
<212> TYPE: PRT
<213> ORGANISM: Homo sapien

<400> SEQUENCE: 74

Met Glu Pro Thr Val Ala Asp Val His Leu Val Pro Arg Thr Thr Lys
1               5                   10                  15

Glu Val Pro Ala Leu Asp Ala Ala Cys Cys Arg Ala Ala Ser Ile Gly
            20                  25                  30

Val Val Ala Thr Ser Leu Val Val Leu Thr Leu Gly Val Leu Leu Ala
        35                  40                  45

Phe Leu Ser Thr Gln Gly Phe His Val Asp His Thr Ala Glu Leu Arg
    50                  55                  60

Gly Ile Arg Trp Thr Ser Ser Leu Arg Arg Glu Thr Ser Asp Tyr His
65                  70                  75                  80

Arg Thr Leu Thr Pro Thr Leu Glu Ala Leu Leu His Phe Leu Leu Arg
                85                  90                  95

Pro Leu Gln Thr Leu Ser Leu Gly Leu Glu Glu Leu Leu Gln Arg
            100                 105                 110

Gly Ile Arg Ala Arg Leu Arg Glu His Gly Ile Ser Leu Ala Ala Tyr
            115                 120                 125

Gly Thr Ile Val Ser Ala Glu Leu Thr Gly Arg His Lys Gly Pro Leu
130                 135                 140

Ala Glu Arg Asp Phe Lys Ser Gly Arg Cys Pro Gly Asn Ser Phe Ser
145                 150                 155                 160

Cys Gly Asn Ser Gln Cys Val Thr Lys Val Asn Pro Glu Cys Asp Asp
                165                 170                 175

Gln Glu Asp Cys Ser Asp Gly Ser Asp Glu Ala His Cys Glu Cys Gly
            180                 185                 190

Leu Gln Pro Ala Trp Arg Met Ala Gly Arg Ile Val Gly Gly Met Glu
        195                 200                 205

Ala Ser Pro Gly Glu Phe Pro Trp Gln Ala Ser Leu Arg Glu Asn Lys
    210                 215                 220

Glu His Phe Cys Gly Ala Ala Ile Ile Asn Ala Arg Trp Leu Val Ser
225                 230                 235                 240

Ala Ala His Cys Phe Asn Glu Phe Gln Asp Pro Thr Lys Trp Val Ala
                245                 250                 255

Tyr Val Gly Ala Thr Tyr Leu Ser Gly Ser Glu Ala Ser Thr Val Arg
            260                 265                 270

Ala Gln Val Val Gln Ile Val Lys His Pro Leu Tyr Asn Ala Asp Thr
        275                 280                 285

Ala Asp Phe Asp Val Ala Val Leu Glu Leu Thr Ser Pro Leu Pro Phe
    290                 295                 300

Gly Arg His Ile Gln Pro Val Cys Leu Pro Ala Ala Thr His Ile Phe
305                 310                 315                 320

Pro Pro Ser Lys Lys Cys Leu Ile Ser Gly Trp Gly Tyr Leu Lys Glu
                325                 330                 335

Asp Phe Leu Val Lys Pro Glu Val Leu Gln Lys Ala Thr Val Glu Leu
            340                 345                 350

Leu Asp Gln Ala Leu Cys Ala Ser Leu Tyr Gly His Ser Leu Thr Asp
        355                 360                 365

Arg Met Val Cys Ala Gly Tyr Leu Asp Gly Lys Val Asp Ser Cys Gln
    370                 375                 380

Gly Asp Ser Gly Gly Pro Leu Val Cys Glu Glu Pro Ser Gly Arg Phe
```

-continued

```
                385                 390                 395                 400
Phe Leu Ala Gly Ile Val Ser Trp Gly Ile Gly Cys Ala Glu Ala Arg
                    405                 410                 415
Arg Pro Gly Val Tyr Ala Arg Val Thr Arg Leu Arg Asp Trp Ile Leu
                420                 425                 430
Glu Ala Thr Thr Lys Ala Ser Met Pro Leu Ala Pro Thr Met Ala Pro
            435                 440                 445
Ala Pro Ala Ala Pro Ser Thr Ala Trp Pro Thr Ser Pro Glu Ser Pro
450                 455                 460
Val Val Ser Thr Pro Thr Lys Ser Met Gln Ala Leu Ser Thr Val Pro
465                 470                 475                 480
Leu Asp Trp Val Thr Val Pro Lys Leu Gln Glu Cys Gly Ala Arg Pro
                485                 490                 495
Ala Met Glu Lys Pro Thr Arg Val Val Gly Gly Phe Gly Ala Ala Ser
                500                 505                 510
Gly Glu Val Pro Trp Gln Val Ser Leu Lys Gly Ser Arg His Phe
            515                 520                 525
Cys Gly Ala Thr Val Val Gly Asp Arg Trp Leu Leu Ser Ala Ala His
            530                 535                 540
Cys Phe Asn His Thr Lys Val Glu Gln Val Arg Ala His Leu Gly Thr
545                 550                 555                 560
Ala Ser Leu Leu Gly Leu Gly Gly Ser Pro Val Lys Ile Gly Leu Arg
                565                 570                 575
Arg Val Val Leu His Pro Leu Tyr Asn Pro Gly Ile Leu Asp Phe Asp
                580                 585                 590
Leu Ala Val Leu Glu Leu Ala Ser Pro Leu Ala Phe Asn Lys Tyr Ile
                595                 600                 605
Gln Pro Val Cys Leu Pro Leu Ala Ile Gln Lys Phe Pro Val Gly Arg
            610                 615                 620
Lys Cys Met Ile Ser Gly Trp Gly Asn Thr Gln Glu Gly Asn Ala Thr
625                 630                 635                 640
Lys Pro Glu Leu Leu Gln Lys Ala Ser Val Gly Ile Ile Asp Gln Lys
                645                 650                 655
Thr Cys Ser Val Leu Tyr Asn Phe Ser Leu Thr Asp Arg Met Ile Cys
                660                 665                 670
Ala Gly Phe Leu Glu Gly Lys Val Asp Ser Cys Gln Gly Asp Ser Gly
            675                 680                 685
Gly Pro Leu Ala Cys Glu Glu Ala Pro Gly Val Phe Tyr Leu Ala Gly
            690                 695                 700
Ile Val Ser Trp Gly Ile Gly Cys Ala Gln Val Lys Lys Pro Gly Val
705                 710                 715                 720
Tyr Thr Arg Ile Thr Arg Leu Lys Gly Trp Ile Leu Glu Ile Met Ser
                725                 730                 735
Ser Gln Pro Leu Pro Met Ser Pro Ser Thr Thr Arg Met Leu Ala
            740                 745                 750
Thr Thr Ser Pro Arg Thr Thr Ala Gly Leu Thr Val Pro Gly Ala Thr
            755                 760                 765
Pro Ser Arg Pro Thr Pro Gly Ala Ala Ser Arg Val Thr Gly Gln Pro
            770                 775                 780
Ala Asn Ser Thr Leu Ser Ala Val Ser Thr Thr Ala Arg Gly Gln Thr
785                 790                 795                 800
Pro Phe Pro Asp Ala Pro Glu Ala Thr Thr His Thr Gln Leu Pro Asp
                    805                 810                 815
```

```
Cys Gly Leu Ala Pro Ala Ala Leu Thr Arg Ile Val Gly Gly Ser Ala
            820                 825                 830

Ala Gly Arg Gly Glu Trp Pro Trp Gln Val Ser Leu Trp Leu Arg Arg
        835                 840                 845

Arg Glu His Arg Cys Gly Ala Val Leu Val Ala Glu Arg Trp Leu Leu
    850                 855                 860

Ser Ala Ala His Cys Phe Asp Val Tyr Gly Asp Pro Lys Gln Trp Ala
865                 870                 875                 880

Ala Phe Leu Gly Thr Pro Phe Leu Ser Gly Ala Glu Gly Gln Leu Glu
                885                 890                 895

Arg Val Ala Arg Ile Tyr Lys His Pro Phe Tyr Asn Leu Tyr Thr Leu
            900                 905                 910

Asp Tyr Asp Val Ala Leu Leu Glu Leu Ala Gly Pro Val Arg Arg Ser
        915                 920                 925

Arg Leu Val Arg Pro Ile Cys Leu Pro Glu Pro Ala Pro Arg Pro Pro
    930                 935                 940

Asp Gly Thr Arg Cys Val Ile Thr Gly Trp Gly Ser Val Arg Glu Gly
945                 950                 955                 960

Gly Ser Met Ala Arg Gln Leu Gln Lys Ala Ala Val Arg Leu Leu Ser
                965                 970                 975

Glu Gln Thr Cys Arg Arg Phe Tyr Pro Val Gln Ile Ser Ser Arg Met
            980                 985                 990

Leu Cys Ala Gly Phe Pro Gln Gly Gly Val Asp Ser Cys Ser Gly Asp
        995                 1000                1005

Ala Gly Gly Pro Leu Ala Cys Arg Glu Pro Ser Gly Arg Trp Val
    1010                1015                1020

Leu Thr Gly Val Thr Ser Trp Gly Tyr Gly Cys Gly Arg Pro His
    1025                1030                1035

Phe Pro Gly Val Tyr Thr Arg Val Ala Ala Val Arg Gly Trp Ile
    1040                1045                1050

Gly Gln His Ile Gln Glu
    1055

<210> SEQ ID NO 75
<211> LENGTH: 1042
<212> TYPE: PRT
<213> ORGANISM: Homo sapien

<400> SEQUENCE: 75

Met Lys Gln Ser Pro Ala Leu Ala Pro Glu Glu Arg Cys Arg Arg Ala
1               5                   10                  15

Gly Ser Pro Lys Pro Val Leu Arg Ala Asp Asp Asn Met Gly Asn
            20                  25                  30

Gly Cys Ser Gln Lys Leu Ala Thr Ala Asn Leu Leu Arg Phe Leu Leu
        35                  40                  45

Leu Val Leu Ile Pro Cys Ile Cys Ala Leu Val Leu Leu Leu Val Ile
    50                  55                  60

Leu Leu Ser Tyr Val Gly Thr Leu Gln Lys Val Tyr Phe Lys Ser Asn
65                  70                  75                  80

Gly Ser Glu Pro Leu Val Thr Asp Gly Glu Ile Gln Gly Ser Asp Val
                85                  90                  95

Ile Leu Thr Asn Thr Ile Tyr Asn Gln Ser Thr Val Val Ser Thr Ala
            100                 105                 110

His Pro Asp Gln His Val Pro Ala Trp Thr Asp Ala Ser Leu Pro
    115                 120                 125
```

```
Gly Asp Gln Ser His Arg Asn Thr Ser Ala Cys Met Asn Ile Thr His
130                 135                 140

Ser Gln Cys Gln Met Leu Pro Tyr His Ala Thr Leu Thr Pro Leu Leu
145                 150                 155                 160

Ser Val Val Arg Asn Met Glu Met Glu Lys Phe Leu Lys Phe Phe Thr
                165                 170                 175

Tyr Leu His Arg Leu Ser Cys Tyr Gln His Ile Met Leu Phe Gly Cys
                180                 185                 190

Thr Leu Ala Phe Pro Glu Cys Ile Ile Asp Gly Asp Ser His Gly
                195                 200                 205

Leu Leu Pro Cys Arg Ser Phe Cys Glu Ala Ala Lys Glu Gly Cys Glu
210                 215                 220

Ser Val Leu Gly Met Val Asn Tyr Ser Trp Pro Asp Phe Leu Arg Cys
225                 230                 235                 240

Ser Gln Phe Arg Asn Gln Thr Glu Ser Ser Asn Val Ser Arg Ile Cys
                245                 250                 255

Phe Ser Pro Gln Gln Glu Asn Gly Lys Gln Leu Leu Cys Gly Arg Gly
                260                 265                 270

Glu Asn Phe Leu Cys Ala Ser Gly Ile Cys Ile Pro Gly Lys Leu Gln
                275                 280                 285

Cys Asn Gly Tyr Asn Asp Cys Asp Asp Trp Ser Asp Glu Ala His Cys
290                 295                 300

Asn Cys Ser Glu Asn Leu Phe His Cys His Thr Gly Lys Cys Leu Asn
305                 310                 315                 320

Tyr Ser Leu Val Cys Asp Gly Tyr Asp Asp Cys Gly Asp Leu Ser Asp
                325                 330                 335

Glu Gln Asn Cys Asp Cys Asn Pro Thr Thr Glu His Arg Cys Gly Asp
                340                 345                 350

Gly Arg Cys Ile Ala Met Glu Trp Val Cys Asp Gly Asp His Asp Cys
                355                 360                 365

Val Asp Lys Ser Asp Glu Val Asn Cys Ser Cys His Ser Gln Gly Leu
                370                 375                 380

Val Glu Cys Arg Asn Gly Gln Cys Ile Pro Ser Thr Phe Gln Cys Asp
385                 390                 395                 400

Gly Asp Glu Asp Cys Lys Asp Gly Ser Asp Glu Glu Asn Cys Ser Val
                405                 410                 415

Ile Gln Thr Ser Cys Gln Glu Gly Asp Gln Arg Cys Leu Tyr Asn Pro
                420                 425                 430

Cys Leu Asp Ser Cys Gly Gly Ser Leu Cys Asp Pro Asn Asn Ser
                435                 440                 445

Leu Asn Asn Cys Ser Gln Cys Glu Pro Ile Thr Leu Glu Leu Cys Met
450                 455                 460

Asn Leu Pro Tyr Asn Ser Thr Ser Tyr Pro Asn Tyr Phe Gly His Arg
465                 470                 475                 480

Thr Gln Lys Glu Ala Ser Ile Ser Trp Glu Ser Ser Leu Phe Pro Ala
                485                 490                 495

Leu Val Gln Thr Asn Cys Tyr Lys Tyr Leu Met Phe Phe Ser Cys Thr
                500                 505                 510

Ile Leu Val Pro Lys Cys Asp Val Asn Thr Gly Glu His Ile Pro Pro
                515                 520                 525

Cys Arg Ala Leu Cys Glu His Ser Lys Glu Arg Cys Glu Ser Val Leu
530                 535                 540

Gly Ile Val Gly Leu Gln Trp Pro Glu Asp Thr Asp Cys Ser Gln Phe
545                 550                 555                 560
```

```
Pro Glu Glu Asn Ser Asp Asn Gln Thr Cys Leu Met Pro Asp Glu Tyr
            565                 570                 575

Val Glu Glu Cys Ser Pro Ser His Phe Lys Cys Arg Ser Gly Gln Cys
        580                 585                 590

Val Leu Ala Ser Arg Arg Cys Asp Gly Gln Ala Asp Cys Asp Asp
            595                 600                 605

Ser Asp Glu Glu Asn Cys Gly Cys Lys Glu Arg Asp Leu Trp Glu Cys
    610                 615                 620

Pro Ser Asn Lys Gln Cys Leu Lys His Thr Val Ile Cys Asp Gly Phe
625                 630                 635                 640

Pro Asp Cys Pro Asp Tyr Met Asp Glu Lys Asn Cys Ser Phe Cys Gln
                645                 650                 655

Asp Asp Glu Leu Glu Cys Ala Asn His Ala Cys Val Ser Arg Asp Leu
            660                 665                 670

Trp Cys Asp Gly Glu Ala Asp Cys Ser Asp Ser Ser Asp Glu Trp Asp
        675                 680                 685

Cys Val Thr Leu Ser Ile Asn Val Asn Ser Ser Ser Phe Leu Met Val
            690                 695                 700

His Arg Ala Ala Thr Glu His His Val Cys Ala Asp Gly Trp Gln Glu
705                 710                 715                 720

Ile Leu Ser Gln Leu Ala Cys Lys Gln Met Gly Leu Gly Glu Pro Ser
                725                 730                 735

Val Thr Lys Leu Ile Gln Glu Gln Glu Lys Glu Pro Arg Trp Leu Thr
            740                 745                 750

Leu His Ser Asn Trp Glu Ser Leu Asn Gly Thr Thr Leu His Glu Leu
        755                 760                 765

Leu Val Asn Gly Gln Ser Cys Glu Ser Arg Ser Lys Ile Ser Leu Leu
    770                 775                 780

Cys Thr Lys Gln Asp Cys Gly Arg Arg Pro Ala Ala Arg Met Asn Lys
785                 790                 795                 800

Arg Ile Leu Gly Gly Arg Thr Ser Arg Pro Gly Arg Trp Pro Trp Gln
                805                 810                 815

Cys Ser Leu Gln Ser Glu Pro Ser Gly His Ile Cys Gly Cys Val Leu
            820                 825                 830

Ile Ala Lys Lys Trp Val Leu Thr Val Ala His Cys Phe Glu Gly Arg
        835                 840                 845

Glu Asn Ala Ala Val Trp Lys Val Val Leu Gly Ile Asn Asn Leu Asp
    850                 855                 860

His Pro Ser Val Phe Met Gln Thr Arg Phe Val Lys Thr Ile Ile Leu
865                 870                 875                 880

His Pro Arg Tyr Ser Arg Ala Val Val Asp Tyr Asp Ile Ser Ile Val
                885                 890                 895

Glu Leu Ser Glu Asp Ile Ser Glu Thr Gly Tyr Val Arg Pro Val Cys
            900                 905                 910

Leu Pro Asn Pro Glu Gln Trp Leu Glu Pro Asp Thr Tyr Cys Tyr Ile
        915                 920                 925

Thr Gly Trp Gly His Met Gly Asn Lys Met Pro Phe Lys Leu Gln Glu
    930                 935                 940

Gly Glu Val Arg Ile Ile Ser Leu Glu His Cys Gln Ser Tyr Phe Asp
945                 950                 955                 960

Met Lys Thr Ile Thr Thr Arg Met Ile Cys Ala Gly Tyr Glu Ser Gly
                965                 970                 975

Thr Val Asp Ser Cys Met Gly Asp Ser Gly Gly Pro Leu Val Cys Glu
```

-continued

```
                980                 985                 990
Lys Pro Gly Gly Arg Trp Thr Leu Phe Gly Leu Thr Ser Trp Gly Ser
            995                 1000                1005

Val Cys Phe Ser Lys Val Leu Gly Pro Gly Val Tyr Ser Asn Val
    1010                1015                1020

Ser Tyr Phe Val Glu Trp Ile Lys Arg Gln Ile Tyr Ile Gln Thr
    1025                1030                1035

Phe Leu Leu Asn
    1040

<210> SEQ ID NO 76
<211> LENGTH: 537
<212> TYPE: PRT
<213> ORGANISM: Homo sapien

<400> SEQUENCE: 76

Met Glu Arg Asp Ser His Gly Asn Ala Ser Pro Ala Arg Thr Pro Ser
1               5                   10                  15

Ala Gly Ala Ser Pro Ala Gln Ala Ser Pro Ala Gly Thr Pro Pro Gly
            20                  25                  30

Arg Ala Ser Pro Ala Gln Ala Ser Pro Ala Gln Ala Ser Pro Ala Gly
        35                  40                  45

Thr Pro Pro Gly Arg Ala Ser Pro Ala Gln Ala Ser Pro Ala Gly Thr
    50                  55                  60

Pro Pro Gly Arg Ala Ser Pro Gly Arg Ala Ser Pro Ala Gln Ala Ser
65                  70                  75                  80

Pro Ala Gln Ala Ser Pro Ala Gln Ala Ser Pro Ala Arg Ala Ser Pro
                85                  90                  95

Ala Leu Ala Ser Leu Ser Arg Ser Ser Gly Arg Ser Ser Ser Ala
            100                 105                 110

Arg Ser Ala Ser Val Thr Thr Ser Pro Thr Arg Val Tyr Leu Val Arg
        115                 120                 125

Ala Thr Pro Val Gly Ala Val Pro Ile Arg Ser Ser Pro Ala Arg Ser
    130                 135                 140

Ala Pro Ala Thr Arg Ala Thr Arg Glu Ser Pro Val Gln Phe Trp Gln
145                 150                 155                 160

Gly His Thr Gly Ile Arg Tyr Lys Glu Gln Arg Glu Ser Cys Pro Lys
                165                 170                 175

His Ala Val Arg Cys Asp Gly Val Val Asp Cys Lys Leu Lys Ser Asp
            180                 185                 190

Glu Leu Gly Cys Val Arg Phe Asp Trp Asp Lys Ser Leu Leu Lys Ile
        195                 200                 205

Tyr Ser Gly Ser Ser His Gln Trp Leu Pro Ile Cys Ser Ser Asn Trp
    210                 215                 220

Asn Asp Ser Tyr Ser Glu Lys Thr Cys Arg Gln Leu Gly Phe Glu Ser
225                 230                 235                 240

Ala His Arg Thr Thr Glu Val Ala His Arg Asp Phe Ala Asn Ser Phe
                245                 250                 255

Ser Ile Leu Arg Tyr Asn Ser Thr Ile Gln Glu Ser Leu His Arg Ser
            260                 265                 270

His Cys Pro Ser Gln Arg Tyr Ile Ser Leu Gln Cys Ser His Cys Gly
        275                 280                 285

Leu Arg Ala Met Thr Gly Arg Ile Val Gly Gly Ala Leu Ala Ser Asp
    290                 295                 300

Ser Lys Trp Pro Trp Gln Val Ser Leu His Phe Gly Thr Thr His Ile
```

```
            305                 310                 315                 320

Cys Gly Gly Thr Leu Ile Asp Ala Gln Trp Val Leu Thr Ala Ala His
                        325                 330                 335

Cys Phe Phe Val Thr Arg Glu Lys Val Leu Glu Gly Trp Lys Val Tyr
                        340                 345                 350

Ala Gly Thr Ser Asn Leu His Gln Leu Pro Glu Ala Ala Ser Ile Ala
                        355                 360                 365

Glu Ile Ile Ile Asn Ser Asn Tyr Thr Asp Glu Asp Asp Tyr Asp
        370                 375                 380

Ile Ala Leu Met Arg Leu Ser Lys Pro Leu Thr Leu Ser Ala His Ile
        385                 390                 395                 400

His Pro Ala Cys Leu Pro Met His Gly Gln Thr Phe Ser Leu Asn Glu
                        405                 410                 415

Thr Cys Trp Ile Thr Gly Phe Gly Lys Thr Arg Glu Thr Asp Asp Lys
                        420                 425                 430

Thr Ser Pro Phe Leu Arg Glu Val Gln Val Asn Leu Ile Asp Phe Lys
                        435                 440                 445

Lys Cys Asn Asp Tyr Leu Val Tyr Asp Ser Tyr Leu Thr Pro Arg Met
                        450                 455                 460

Met Cys Ala Gly Asp Leu His Gly Gly Arg Asp Ser Cys Gln Gly Asp
        465                 470                 475                 480

Ser Gly Gly Pro Leu Val Cys Glu Gln Asn Asn Arg Trp Tyr Leu Ala
                        485                 490                 495

Gly Val Thr Ser Trp Gly Thr Gly Cys Gly Gln Arg Asn Lys Pro Gly
                        500                 505                 510

Val Tyr Thr Lys Val Thr Glu Val Leu Pro Trp Ile Tyr Ser Lys Met
                        515                 520                 525

Glu Ser Glu Val Arg Phe Arg Lys Ser
                        530                 535

<210> SEQ ID NO 77
<211> LENGTH: 348
<212> TYPE: PRT
<213> ORGANISM: Homo sapien

<400> SEQUENCE: 77

Met Arg Leu Gly Leu Leu Ser Val Ala Leu Leu Phe Val Gly Ser Ser
        1               5                   10                  15

His Leu Tyr Ser Asp His Tyr Ser Pro Ser Gly Arg His Arg Leu Gly
                        20                  25                  30

Pro Ser Pro Glu Pro Ala Ala Ser Ser Gln Gln Ala Glu Ala Val Arg
                        35                  40                  45

Lys Arg Leu Arg Arg Arg Glu Gly Gly Ala His Ala Lys Asp Cys
                        50                  55                  60

Gly Thr Ala Pro Leu Lys Asp Val Leu Gln Gly Ser Arg Ile Ile Gly
        65                  70                  75                  80

Gly Thr Glu Ala Gln Ala Gly Ala Trp Pro Trp Val Val Ser Leu Gln
                        85                  90                  95

Ile Lys Tyr Gly Arg Val Leu Val His Val Cys Gly Gly Thr Leu Val
                        100                 105                 110

Arg Glu Arg Trp Val Leu Thr Ala Ala His Cys Thr Lys Asp Ala Ser
                        115                 120                 125

Asp Pro Leu Met Trp Thr Ala Val Ile Gly Thr Asn Asn Ile His Gly
                        130                 135                 140

Arg Tyr Pro His Thr Lys Lys Ile Lys Ile Lys Ala Ile Ile Ile His
```

```
145                 150                 155                 160
Pro Asn Phe Ile Leu Glu Ser Tyr Val Asn Asp Ile Ala Leu Phe His
                165                 170                 175

Leu Lys Lys Ala Val Arg Tyr Asn Asp Tyr Ile Gln Pro Ile Cys Leu
            180                 185                 190

Pro Phe Asp Val Phe Gln Ile Leu Asp Gly Asn Thr Lys Cys Phe Ile
        195                 200                 205

Ser Gly Trp Gly Arg Thr Lys Glu Glu Gly Asn Ala Thr Asn Ile Leu
    210                 215                 220

Gln Asp Ala Glu Val His Tyr Ile Ser Arg Glu Met Cys Asn Ser Glu
225                 230                 235                 240

Arg Ser Tyr Gly Gly Ile Ile Pro Asn Thr Ser Phe Cys Ala Gly Asp
                245                 250                 255

Glu Asp Gly Ala Phe Asp Thr Cys Arg Gly Asp Ser Gly Gly Pro Leu
            260                 265                 270

Met Cys Tyr Leu Pro Glu Tyr Lys Arg Phe Phe Val Met Gly Ile Thr
        275                 280                 285

Ser Tyr Gly His Gly Cys Gly Arg Arg Gly Phe Pro Gly Val Tyr Ile
    290                 295                 300

Gly Pro Ser Phe Tyr Gln Lys Trp Leu Thr Glu His Phe His Ala
305                 310                 315                 320

Ser Thr Gln Gly Ile Leu Thr Ile Asn Ile Leu Arg Gly Gln Ile Leu
                325                 330                 335

Ile Ala Leu Cys Phe Val Ile Leu Leu Ala Thr Thr
            340                 345
```